(12) United States Patent
Behan

(10) Patent No.: US 8,876,800 B2
(45) Date of Patent: Nov. 4, 2014

(54) UROLOGICAL DEVICE

(75) Inventor: Niall Behan, Kilcolgan (IE)

(73) Assignee: Vysera Biomedical Limited, Galway (IE)

( * ) Notice: Subject to any disclaimer, the term of this patent is extended or adjusted under 35 U.S.C. 154(b) by 123 days.

(21) Appl. No.: 12/971,451

(22) Filed: Dec. 17, 2010

(65) Prior Publication Data

US 2011/0160706 A1   Jun. 30, 2011

Related U.S. Application Data

(60) Provisional application No. 61/409,741, filed on Nov. 3, 2010, provisional application No. 61/287,838, filed on Dec. 18, 2009.

(51) Int. Cl.
*A61M 27/00* (2006.01)
*A61M 25/00* (2006.01)
*A61F 2/00* (2006.01)
*A61M 39/06* (2006.01)
*A61M 39/24* (2006.01)

(52) U.S. Cl.
CPC .... *A61M 25/0017* (2013.01); *A61M 2039/0646* (2013.01); *A61M 2039/2433* (2013.01); *A61M 39/06* (2013.01); *A61M 2039/2426* (2013.01); *A61M 25/0075* (2013.01); *A61M 2039/242* (2013.01); *A61F 2/0022* (2013.01); *A61F 2/0009* (2013.01); *A61M 2039/0633* (2013.01); *A61M 39/0606* (2013.01)
USPC ......................................... 604/544; 604/540

(58) Field of Classification Search
USPC .......................................................... 604/34
See application file for complete search history.

(56) References Cited

U.S. PATENT DOCUMENTS

| 3,503,400 | A | * | 3/1970 | Osthagen et al. ............. 604/249 |
| 3,841,304 | A | * | 10/1974 | Jones ............................... 600/29 |
| 4,265,694 | A | | 5/1981 | Boretos et al. |
| 4,271,827 | A | | 6/1981 | Angelchik |
| 4,553,533 | A | | 11/1985 | Leighton |
| 4,603,152 | A | | 7/1986 | Laurin et al. |
| 4,747,849 | A | | 5/1988 | Galtier |
| 4,846,836 | A | | 7/1989 | Reich |

(Continued)

FOREIGN PATENT DOCUMENTS

| GB | 1354691 A | 5/1974 |
| WO | WO-91/01117 A1 | 2/1991 |

(Continued)

OTHER PUBLICATIONS

International Search Report for PCT/IE2010/000075 (Apr. 26, 2011).
International Search Report for PCT/IE2010/000076 (May 31, 2011).
International Search Report and Written Opinion for PCT/IE2011/000060, mailed Dec. 23, 2011 (12 pages).

(Continued)

*Primary Examiner* — Loan H Thanh
*Assistant Examiner* — Andrew S Lo
(74) *Attorney, Agent, or Firm* — Studebaker & Brackett PC

(57) ABSTRACT

A urological device comprises a urological valve having a plurality of valve leaflets with a region of co-aption between the valve leaflets. The valve has a normally closed configuration in which the valve leaflets are engaged at the region of co-aption and an open configuration in which the leaflets are separated at the co-aption region for fluid flow through the valve. The valve is automatically movable from the closed configuration to the open configuration in response to applied urological pressure.

46 Claims, 47 Drawing Sheets

(56) References Cited

U.S. PATENT DOCUMENTS

| | | | |
|---|---|---|---|
| 4,932,938 A | 6/1990 | Goldberg et al. | |
| 4,932,948 A | 6/1990 | Kernes et al. | |
| 4,968,294 A * | 11/1990 | Salama | 600/30 |
| 5,131,906 A | 7/1992 | Ghen | |
| 5,140,999 A | 8/1992 | Ardito | |
| 5,314,473 A | 5/1994 | Godin | |
| 5,484,418 A | 1/1996 | Quiachon et al. | |
| 5,549,657 A | 8/1996 | Stern et al. | |
| 5,653,747 A | 8/1997 | Dereume | |
| 5,782,808 A | 7/1998 | Folden | |
| 5,782,916 A * | 7/1998 | Pintauro et al. | 623/23.66 |
| 5,800,339 A | 9/1998 | Salama | |
| 5,887,594 A | 3/1999 | LoCicero, III | |
| 5,989,288 A | 11/1999 | Pintauro et al. | |
| 6,027,442 A | 2/2000 | Von Iderstein | |
| 6,050,934 A | 4/2000 | Mikhail et al. | |
| 6,066,088 A | 5/2000 | Davis | |
| 6,096,070 A | 8/2000 | Ragheb et al. | |
| 6,234,956 B1 | 5/2001 | He et al. | |
| 6,254,642 B1 | 7/2001 | Taylor | |
| 6,264,700 B1 | 7/2001 | Kilcoyne et al. | |
| 6,302,917 B1 | 10/2001 | Dua et al. | |
| 6,432,040 B1 | 8/2002 | Meah | |
| 6,544,291 B2 | 4/2003 | Taylor | |
| 6,558,429 B2 | 5/2003 | Taylor | |
| 6,669,713 B2 | 12/2003 | Adams | |
| 6,726,696 B1 | 4/2004 | Houser et al. | |
| 6,746,489 B2 | 6/2004 | Dua et al. | |
| 6,790,237 B2 | 9/2004 | Stinson | |
| 6,908,447 B2 | 6/2005 | McWeeney et al. | |
| 6,921,361 B2 | 7/2005 | Suzuki et al. | |
| 6,921,378 B2 | 7/2005 | O'Keefe et al. | |
| 6,958,079 B1 | 10/2005 | Taylor et al. | |
| 6,960,233 B1 | 11/2005 | Berg et al. | |
| 6,976,950 B2 | 12/2005 | Connors et al. | |
| 7,087,088 B2 | 8/2006 | Berg et al. | |
| 7,182,788 B2 | 2/2007 | Jung et al. | |
| 7,470,247 B2 | 12/2008 | Aliski et al. | |
| 7,524,331 B2 | 4/2009 | Birdsall | |
| 7,601,361 B2 | 10/2009 | Lu et al. | |
| 7,678,144 B2 | 3/2010 | Bailey et al. | |
| 7,806,921 B2 | 10/2010 | Hoffman | |
| 7,819,836 B2 | 10/2010 | Levine et al. | |
| 2001/0020189 A1 | 9/2001 | Taylor | |
| 2001/0020190 A1 | 9/2001 | Taylor | |
| 2003/0018309 A1 | 1/2003 | Breznock | |
| 2003/0060894 A1 | 3/2003 | Dua et al. | |
| 2003/0069635 A1 | 4/2003 | Cartledge et al. | |
| 2003/0188755 A1 | 10/2003 | Milbocker | |
| 2003/0199730 A1 | 10/2003 | Silverman et al. | |
| 2003/0199986 A1 | 10/2003 | McWeeney et al. | |
| 2003/0220621 A1 | 11/2003 | Arkinstall | |
| 2004/0044357 A1 | 3/2004 | Gannoe et al. | |
| 2004/0060563 A1 | 4/2004 | Rapacki et al. | |
| 2004/0087905 A1 | 5/2004 | Breznock et al. | |
| 2004/0199262 A1 | 10/2004 | Dua et al. | |
| 2004/0225247 A1 | 11/2004 | Pugsley et al. | |
| 2004/0225373 A1 | 11/2004 | Pugsley et al. | |
| 2005/0125075 A1 | 6/2005 | Meade et al. | |
| 2005/0149201 A1 | 7/2005 | McWeeney et al. | |
| 2005/0228505 A1 | 10/2005 | Cornet et al. | |
| 2005/0267499 A1 | 12/2005 | Stack et al. | |
| 2006/0041189 A1 | 2/2006 | Vancaillie | |
| 2006/0041319 A1 | 2/2006 | Taylor et al. | |
| 2006/0106205 A1 | 5/2006 | Gehant | |
| 2006/0135971 A1 | 6/2006 | Swanstrom et al. | |
| 2006/0142789 A1 | 6/2006 | Lehman et al. | |
| 2006/0206097 A1 | 9/2006 | Breznock et al. | |
| 2006/0264983 A1 | 11/2006 | Holsten et al. | |
| 2006/0265056 A1 | 11/2006 | Nguyen et al. | |
| 2007/0198048 A1 | 8/2007 | Behan et al. | |
| 2008/0036113 A1 | 2/2008 | Chun et al. | |
| 2008/0051879 A1 | 2/2008 | Case et al. | |
| 2008/0091261 A1 | 4/2008 | Long et al. | |
| 2008/0109087 A1 | 5/2008 | Durgin | |
| 2008/0121409 A1 | 5/2008 | King | |
| 2008/0269879 A1 | 10/2008 | Sathe et al. | |
| 2009/0125104 A1 | 5/2009 | Hoffman | |
| 2009/0177270 A1 | 7/2009 | Agnew et al. | |
| 2010/0023114 A1 | 1/2010 | Chambers et al. | |
| 2010/0036504 A1 | 2/2010 | Sobrino-Serrano et al. | |
| 2010/0049306 A1 | 2/2010 | House et al. | |
| 2010/0094209 A1 | 4/2010 | Drasler et al. | |
| 2010/0121461 A1 * | 5/2010 | Sobrino-Serrano et al. | 623/23.68 |
| 2010/0130949 A1 | 5/2010 | Garcia | |
| 2010/0131049 A1 | 5/2010 | Perkins et al. | |
| 2010/0298628 A1 | 11/2010 | Taylor et al. | |
| 2010/0312225 A1 | 12/2010 | Armistead | |
| 2011/0015758 A1 | 1/2011 | Lennox et al. | |
| 2011/0106060 A1 | 5/2011 | Atkinson et al. | |

FOREIGN PATENT DOCUMENTS

| | | |
|---|---|---|
| WO | WO-91/18557 A1 | 12/1991 |
| WO | WO-97/06758 A1 | 2/1997 |
| WO | WO-00/12027 A1 | 3/2000 |
| WO | WO-02/094132 A2 | 11/2002 |
| WO | WO-03003949 A2 | 1/2003 |
| WO | WO-03/011179 A2 | 2/2003 |
| WO | WO-03/017882 A2 | 3/2003 |
| WO | WO-03/030782 A1 | 4/2003 |
| WO | WO-2004/043296 A1 | 5/2004 |
| WO | WO-2005/032422 A1 | 4/2005 |
| WO | WO-2005/058210 A1 | 6/2005 |
| WO | WO-2005/060869 A1 | 7/2005 |
| WO | WO-2006106205 A2 | 10/2006 |
| WO | WO-2007/107990 A2 | 9/2007 |
| WO | WO-2007/136468 A2 | 11/2007 |
| WO | WO-2009/126268 A1 | 10/2009 |
| WO | WO-2009/126331 A1 | 10/2009 |
| WO | WO-2009/139878 A1 | 11/2009 |
| WO | WO-2010/115011 A1 | 10/2010 |
| WO | WO-2011/006098 A2 | 3/2011 |

OTHER PUBLICATIONS

International Search Report for PCT/IE2009/000037 (Sep. 3, 2009).
International Search Report for PCT/IE2009/000039 (Sep. 3, 2009).
International Search Report for PCT/IE2009/000040 (Sep. 3, 2009).
International Search Report for PCT/IE2006/000145 (Jun. 19, 2007).
Catalona W.J.et al.; "Potency, Continence and Complication Rates in 1,870 Consecutive Radical Retropubic Prostatectomies"; The Journal of Urology; Aug. 1999; pp. 433-438; vol. 162(2); American Urological Association Inc.
Demeester T.R. et al.; "Patterns of Gastroesophageal Reflux in Health and Disease"; The Annual Meeting of the American Surgical Association; Oct. 1976; pp. 459-469.
Filipi C.J. et al.; "Transoral, flexible endoscopic suturing for treatment of GERD: a multicenter trial"; Gastrointestinal Endoscopy; 2001; pp. 416-422; vol. 53, No. 4.
Arts J. et al.; "Endoluminal Gastroplication (Endocinch) in GERD Patient's Refractory to PPI Therapy"; Gastroenterology; 2002; 122; p. A-47; AGA Abstracts.
Mahmood Z. et al.; "Endocinch therapy for gastro-oesophageal reflux disease: a one year prospective follow up"; 2003; vol. 52; pp. 34-39; group.bmj.com.
Ismail T. et al.; "Yield pressure, anatomy of the cardia and gastro-oesophageal reflux"; British Journal of Surgery; 1995; vol. 82; pp. 943-947; Blackwell Science Ltd.
Lee W.R. et al.; "Urinary Incontinence Following External-Beam Radiotherapy for Clinically Localized Prostate Cancer"; Jul. 1996; vol. 48(1); pp. 95-99; Elsevier Science Inc.
Pandolfino J.E. et al.; "Ambulatory Esophageal pH Monitoring Using a Wireless System"; The American Journal of Gastroenterology; 2003; vol. 98, No. 4; Elsevier Science Inc.
Park P.O. et al.; "Results of Endoscopic Gastroplasty for Gastroesophageal Reflux Disease"; Gastrointestinal Endoscopy; 2001; vol. 53, No. 5; p. AB115.

* cited by examiner

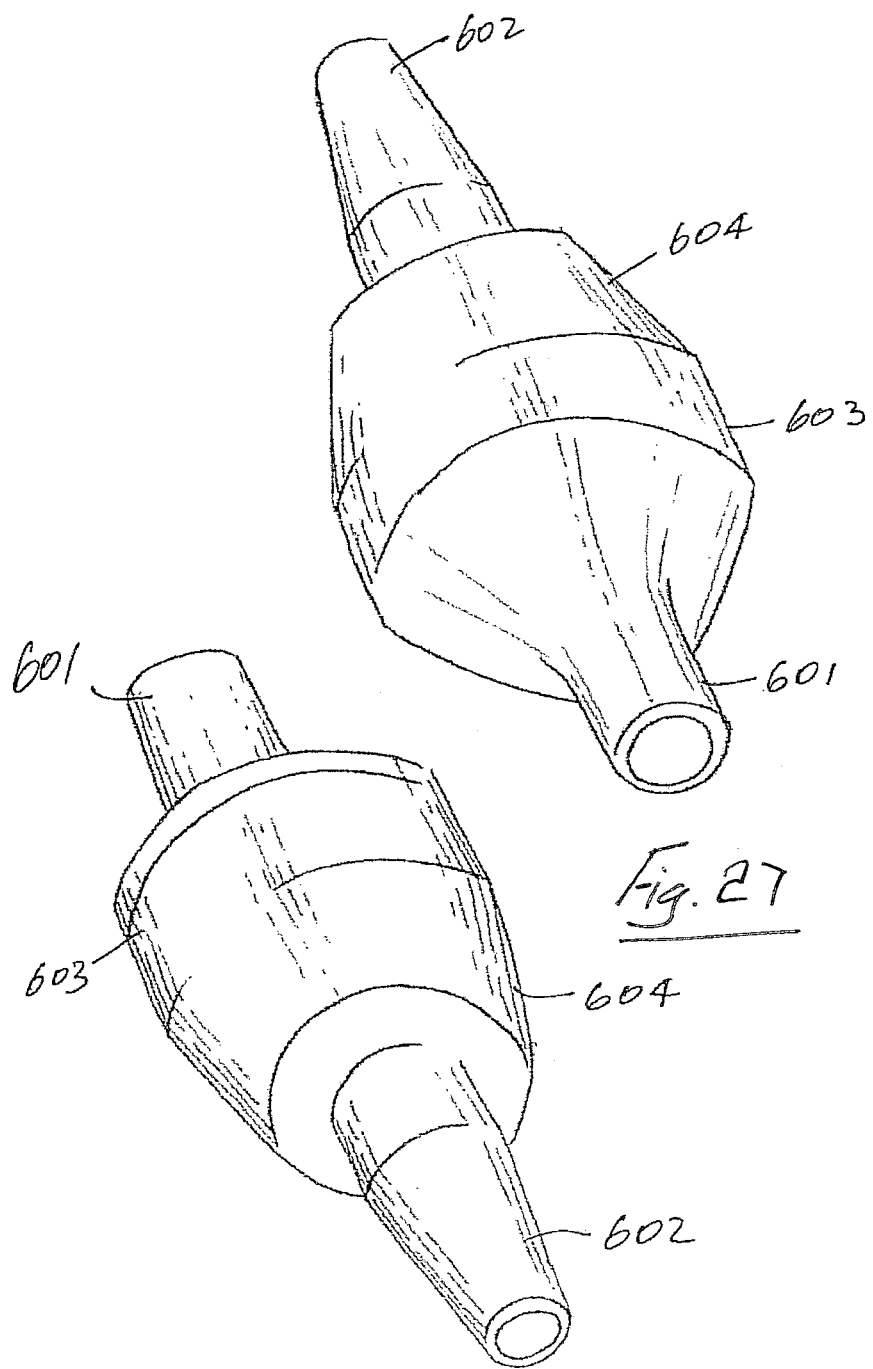

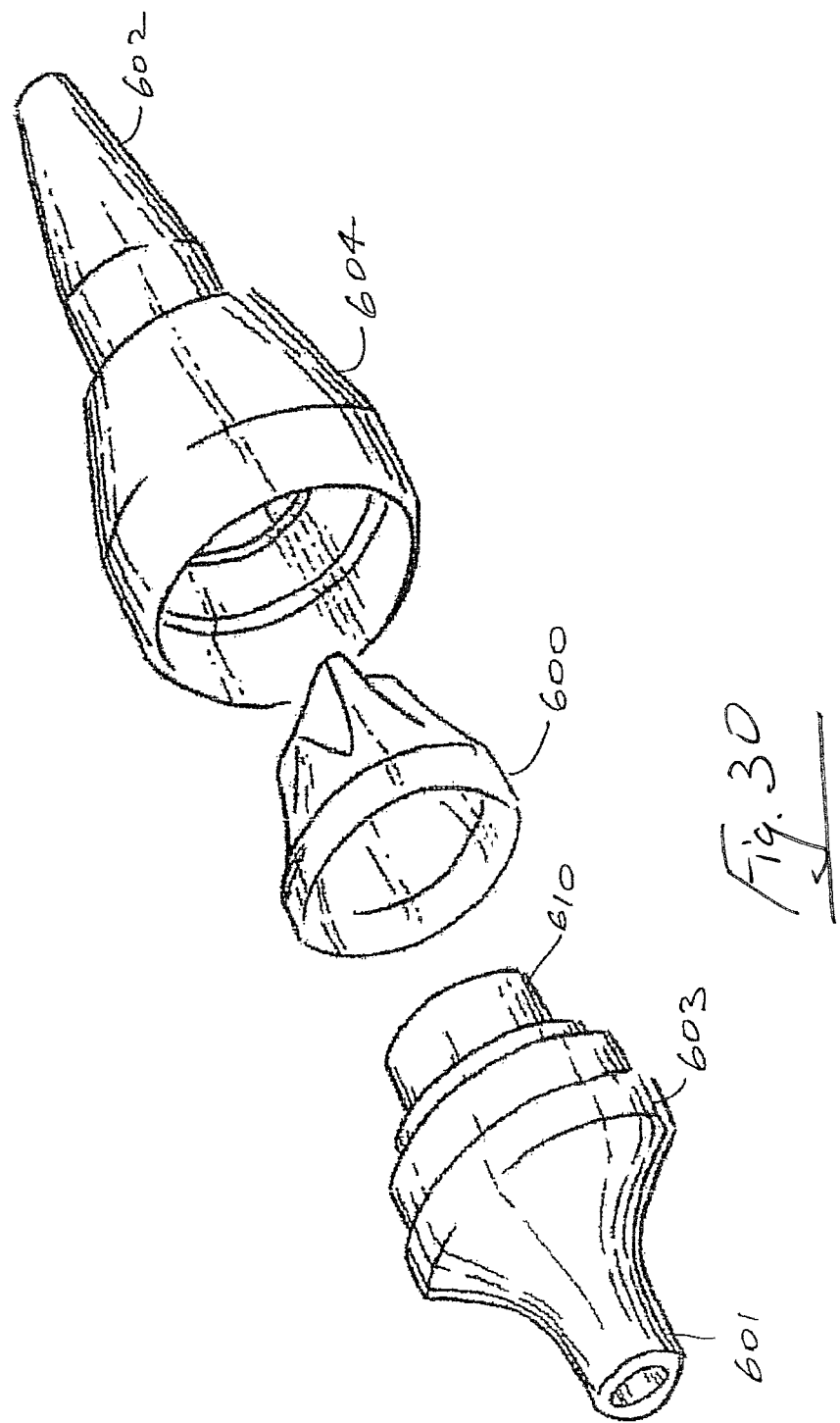

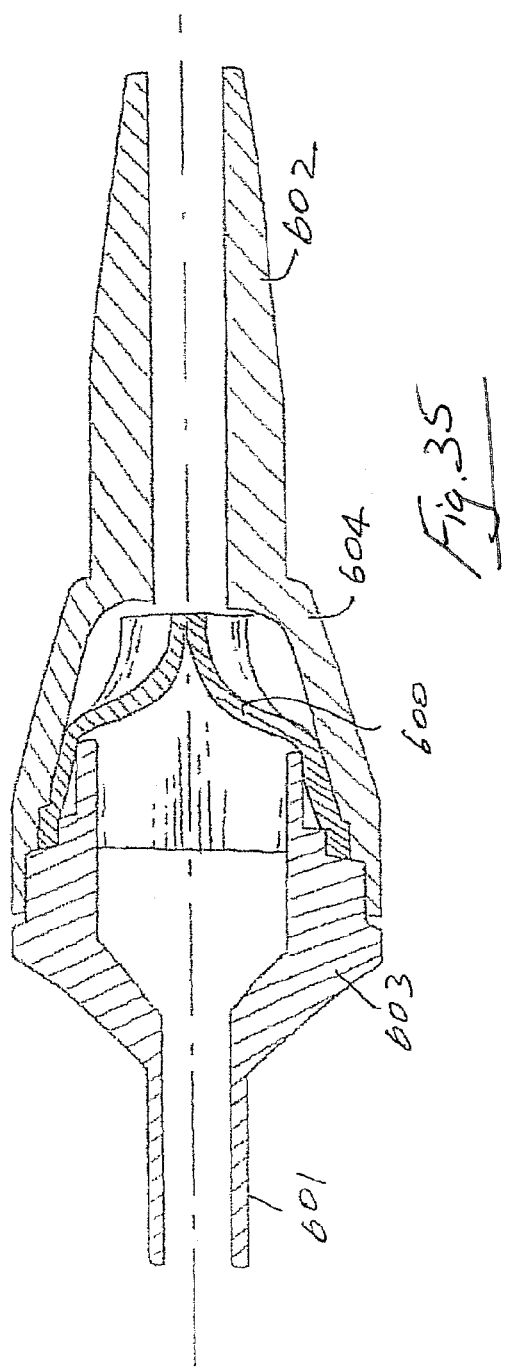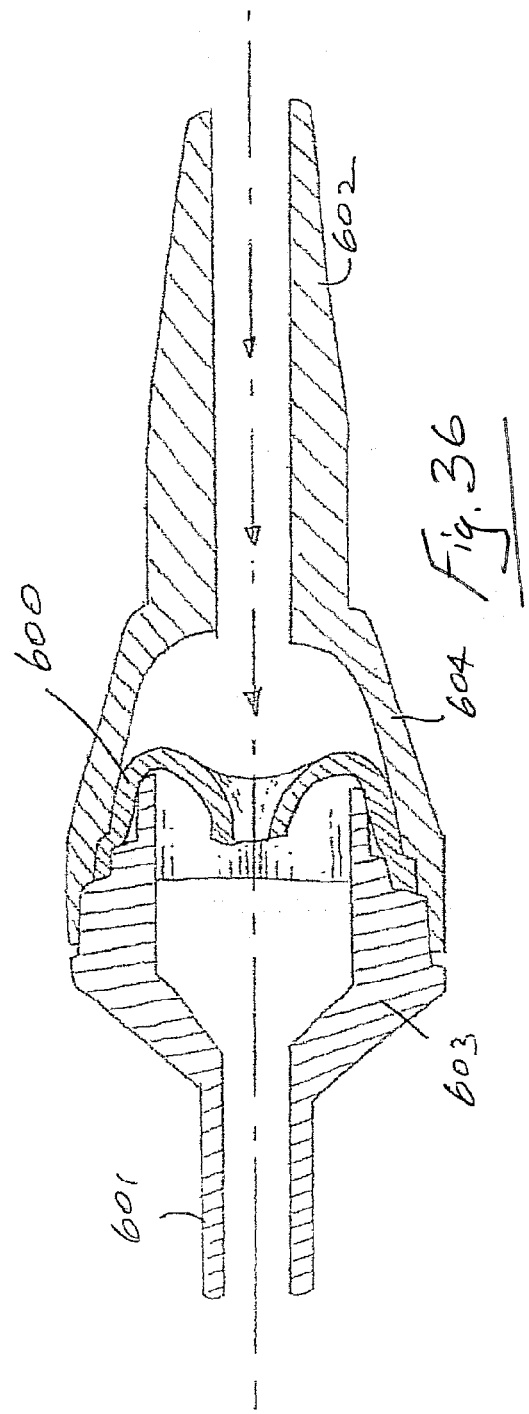

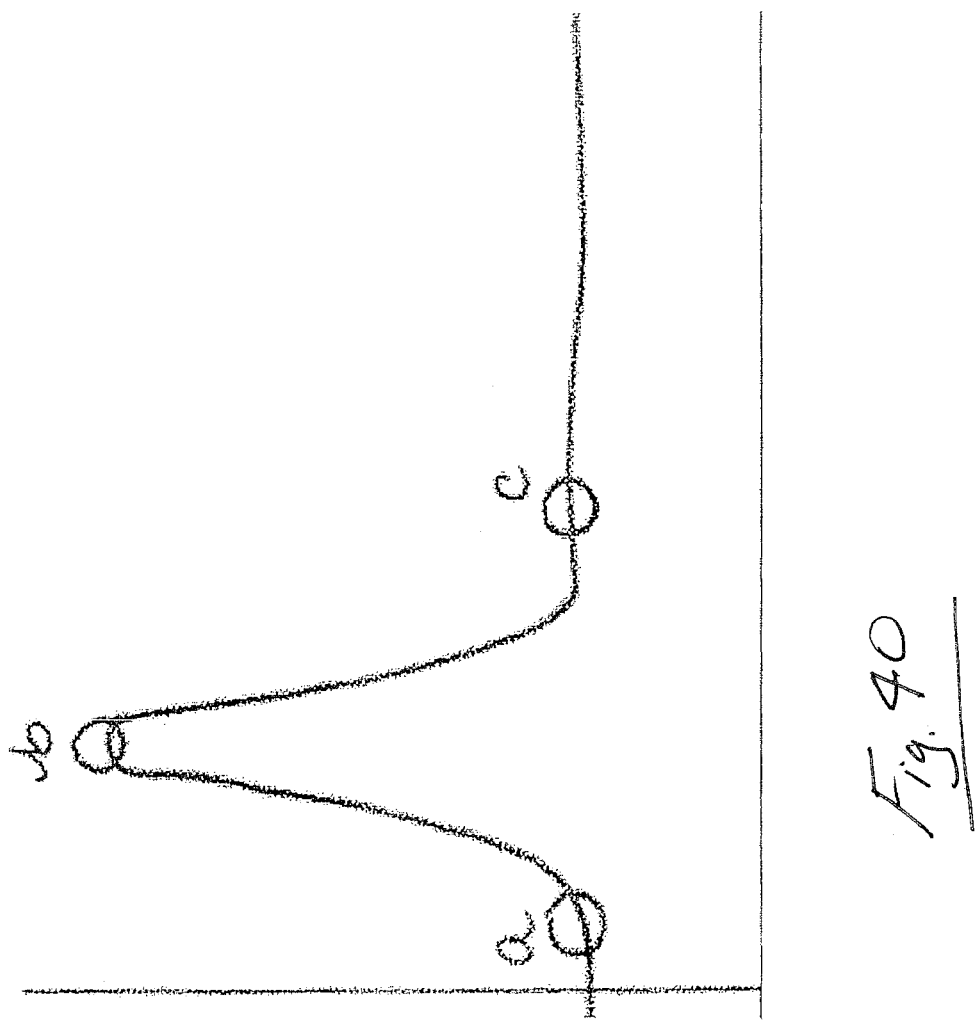

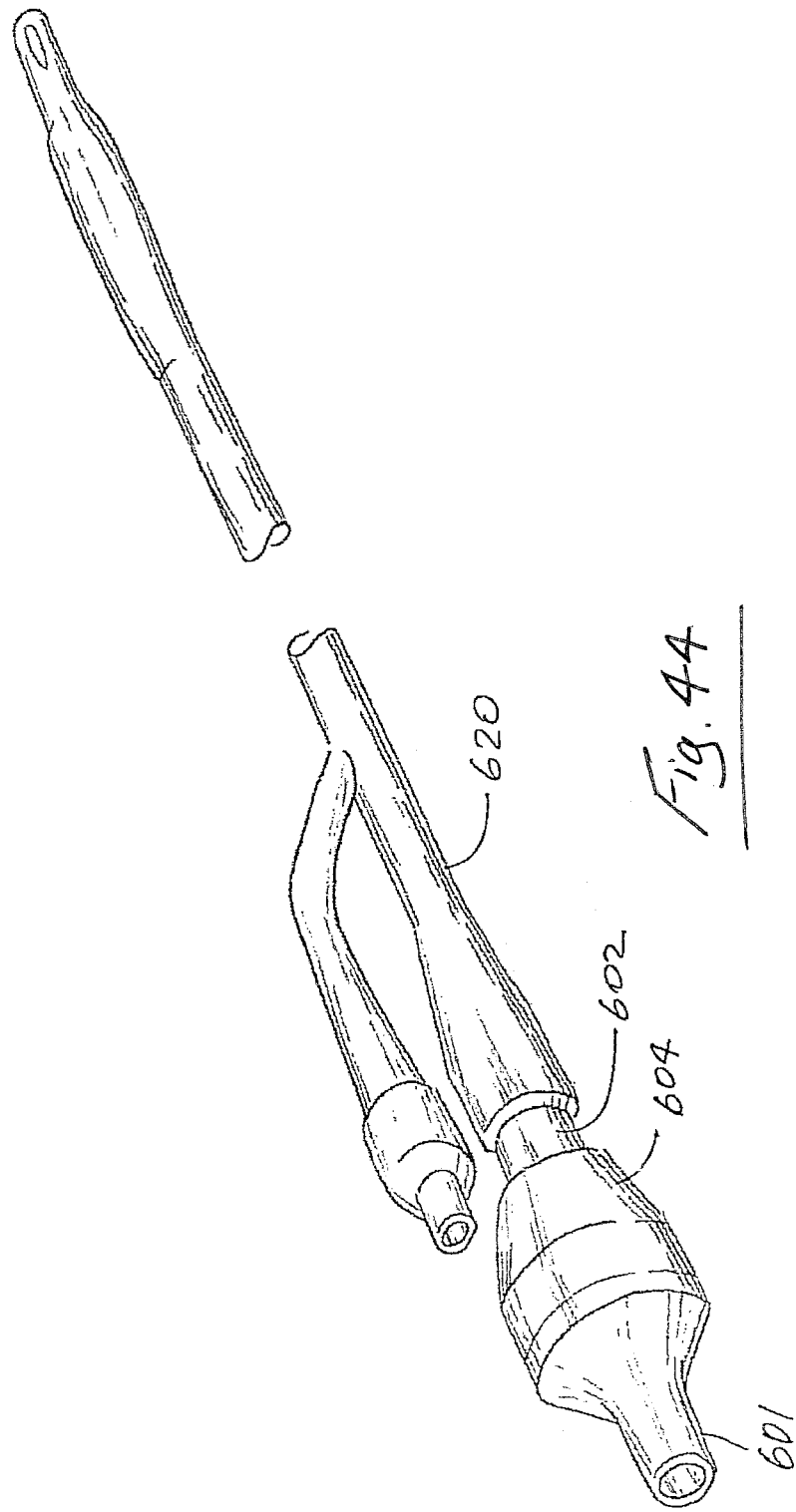

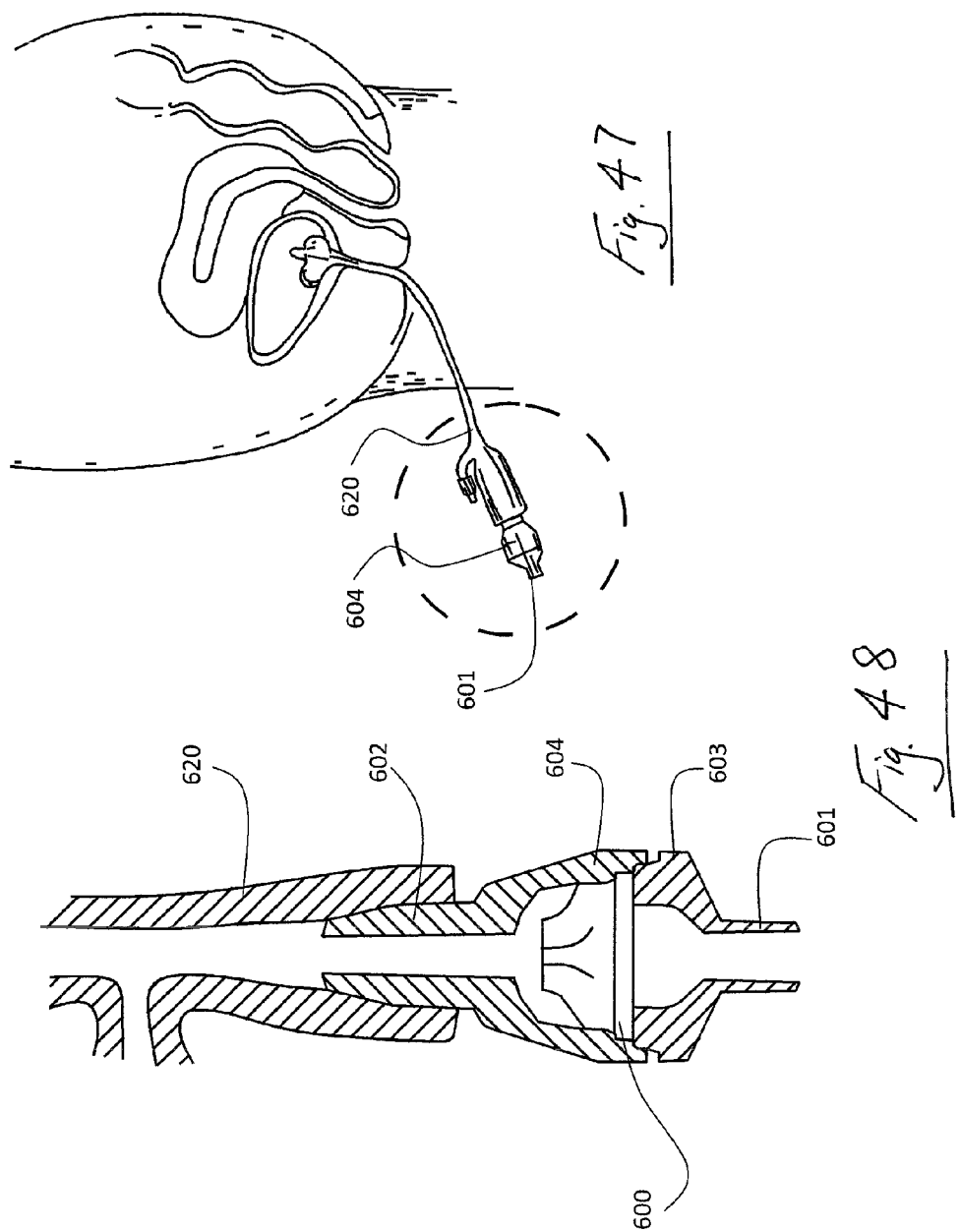

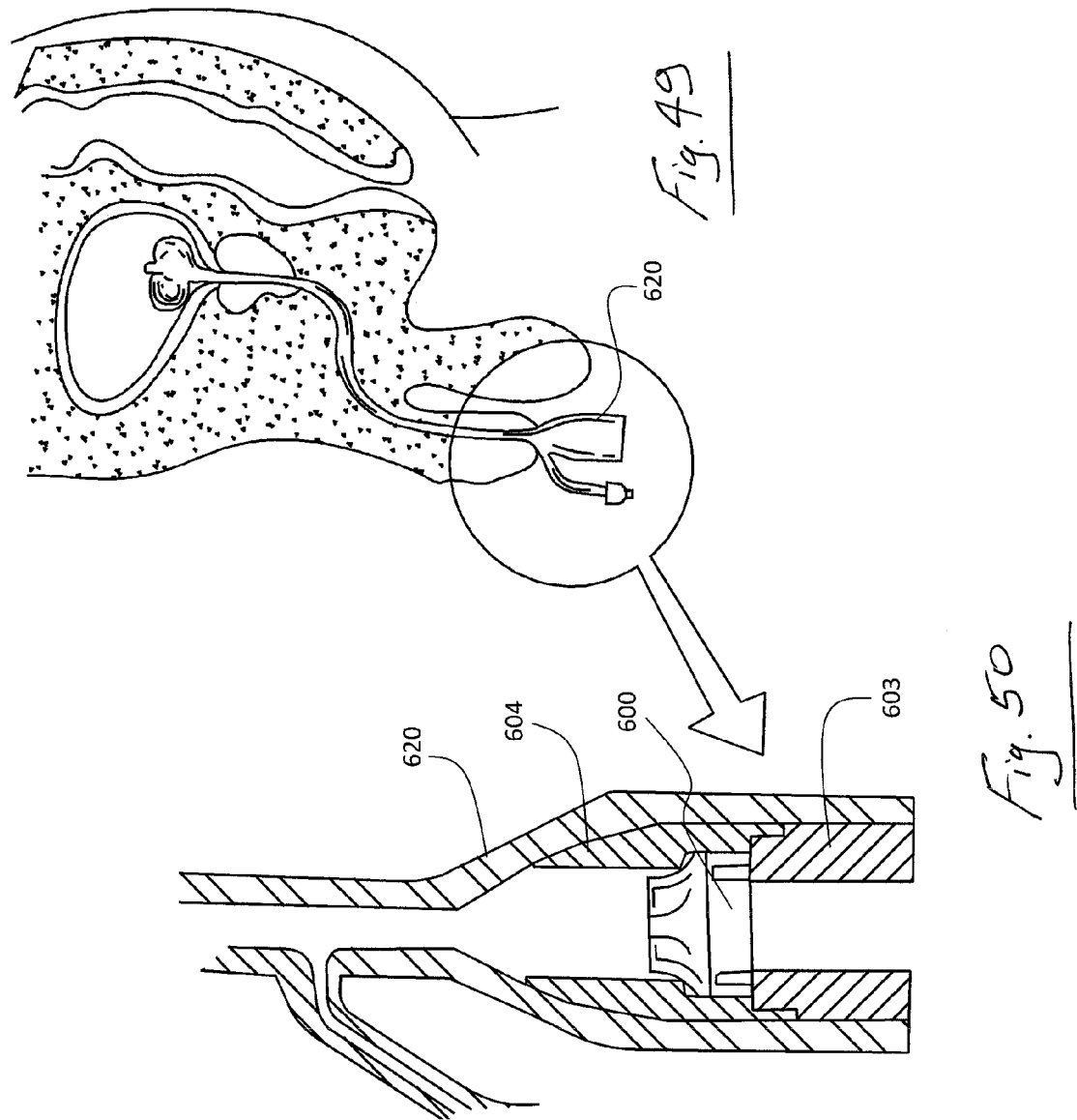

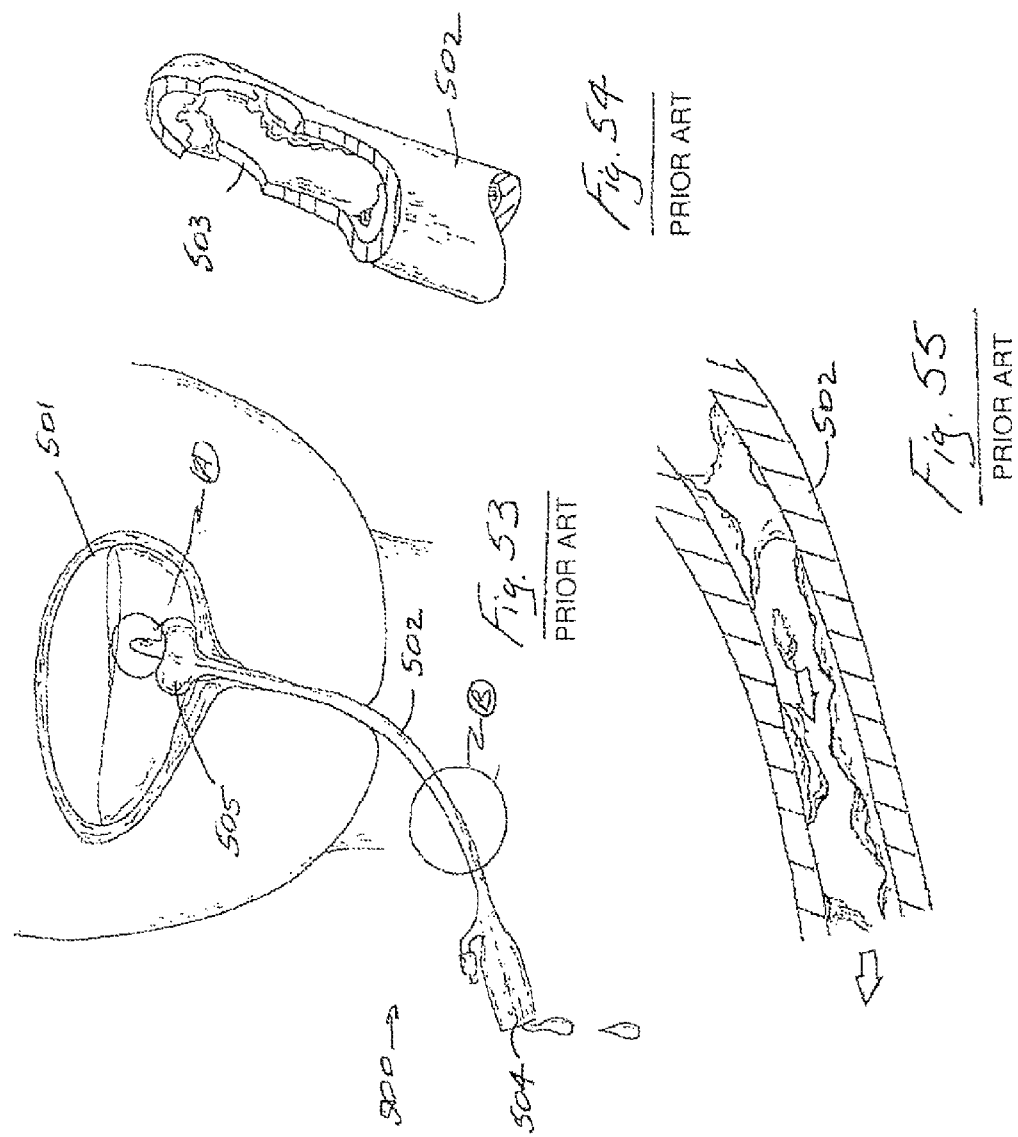

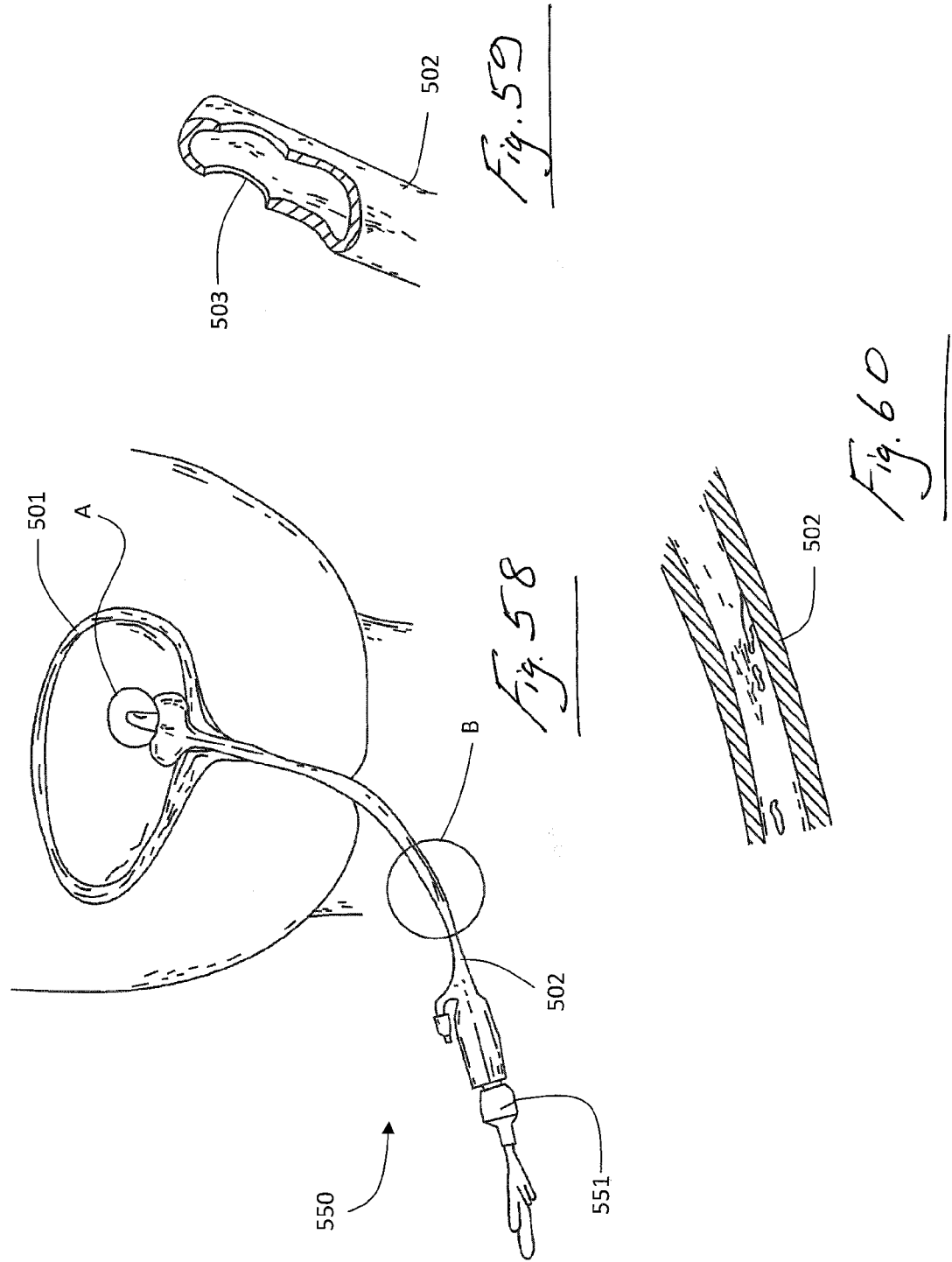

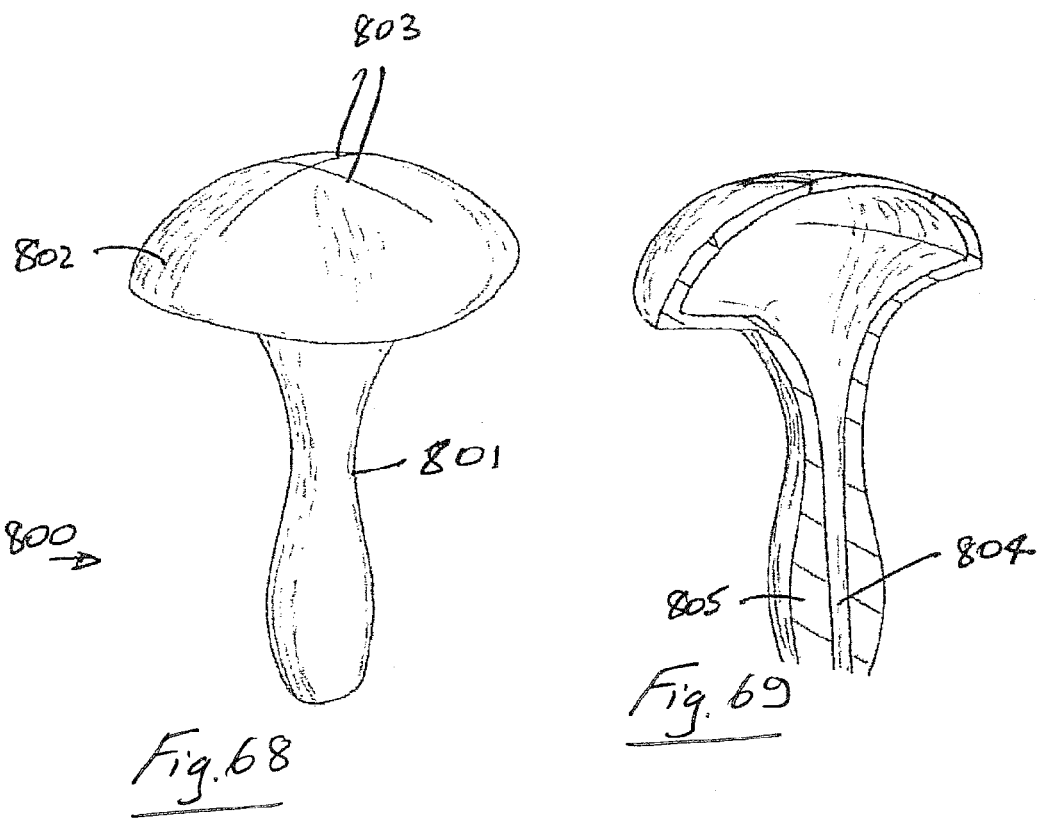
Fig. 68
Fig. 69
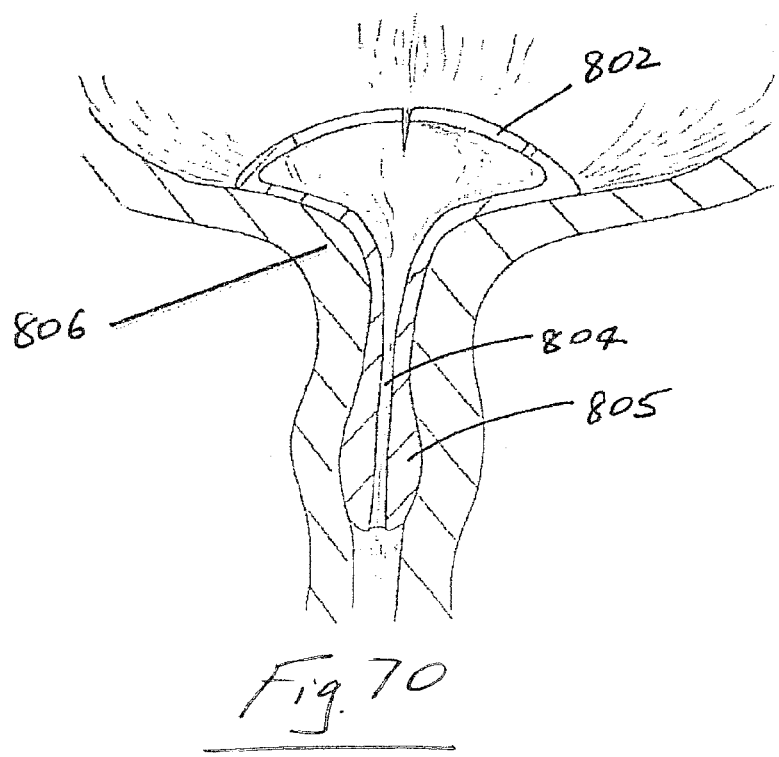
Fig. 70

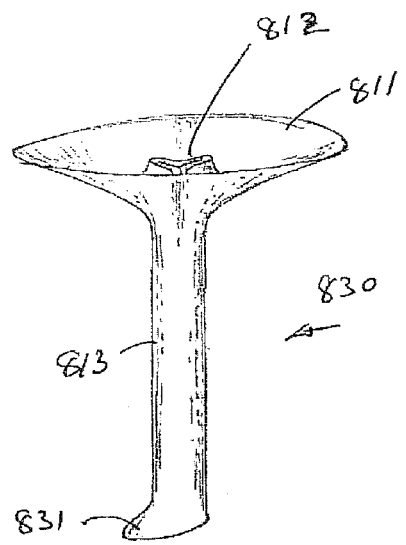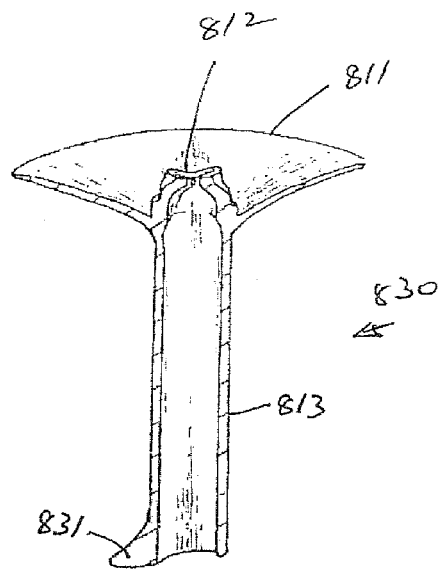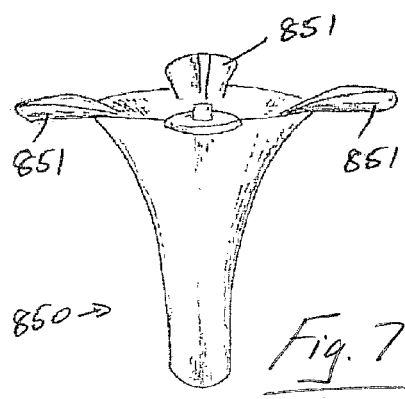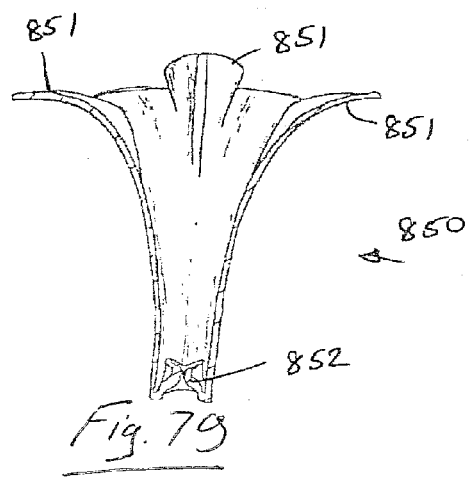

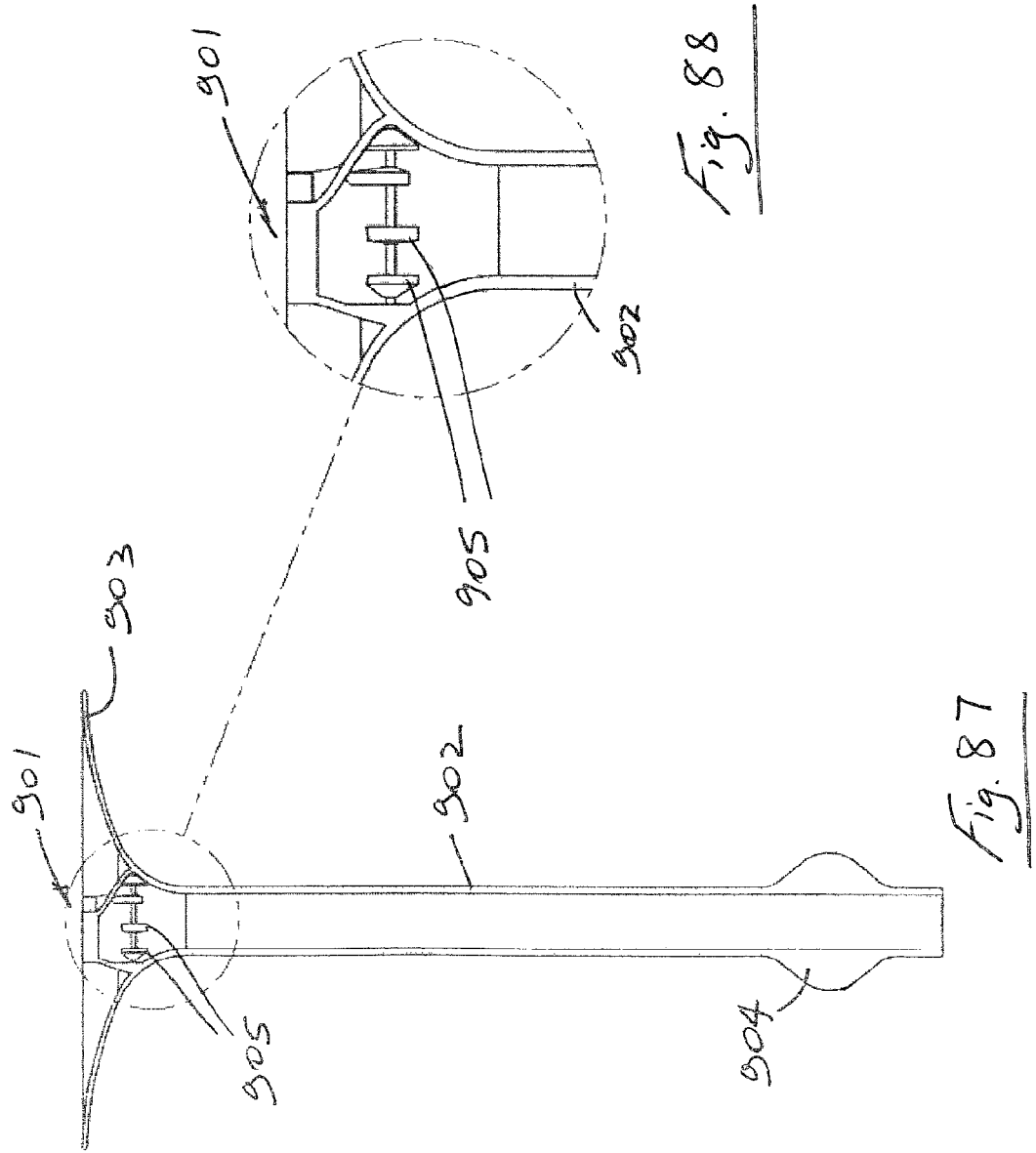

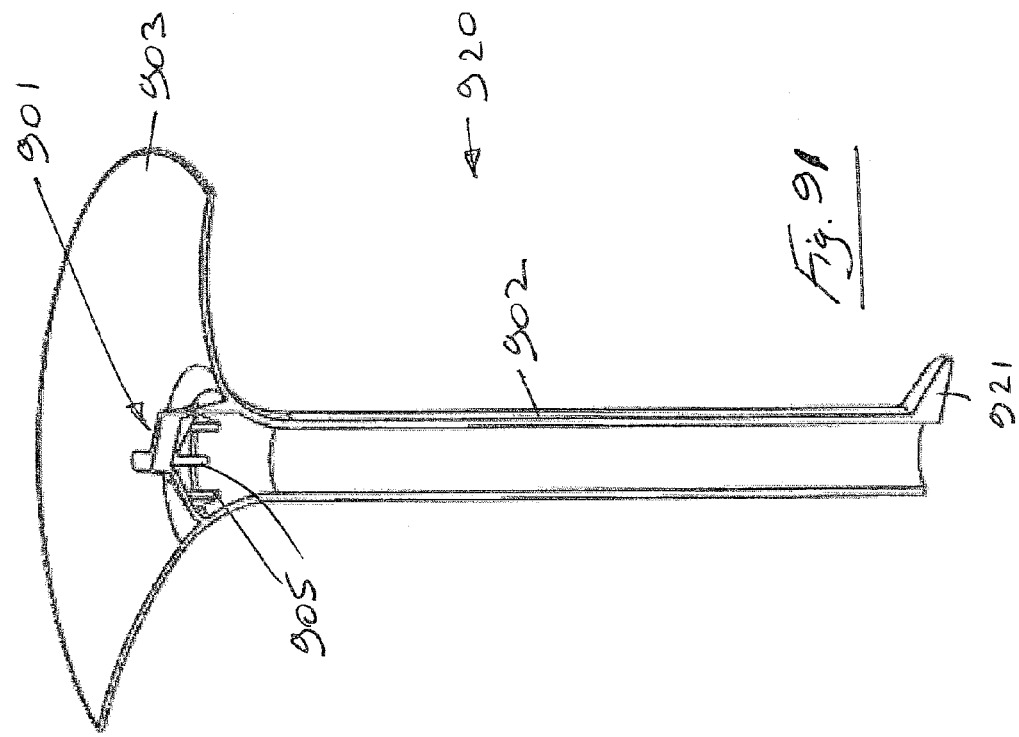
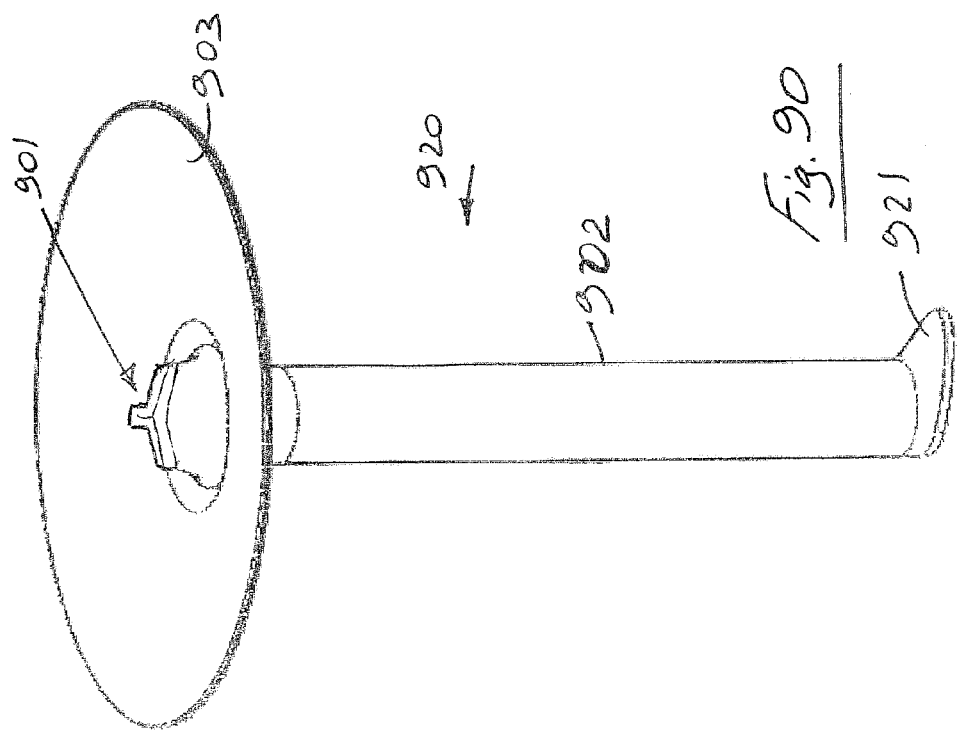

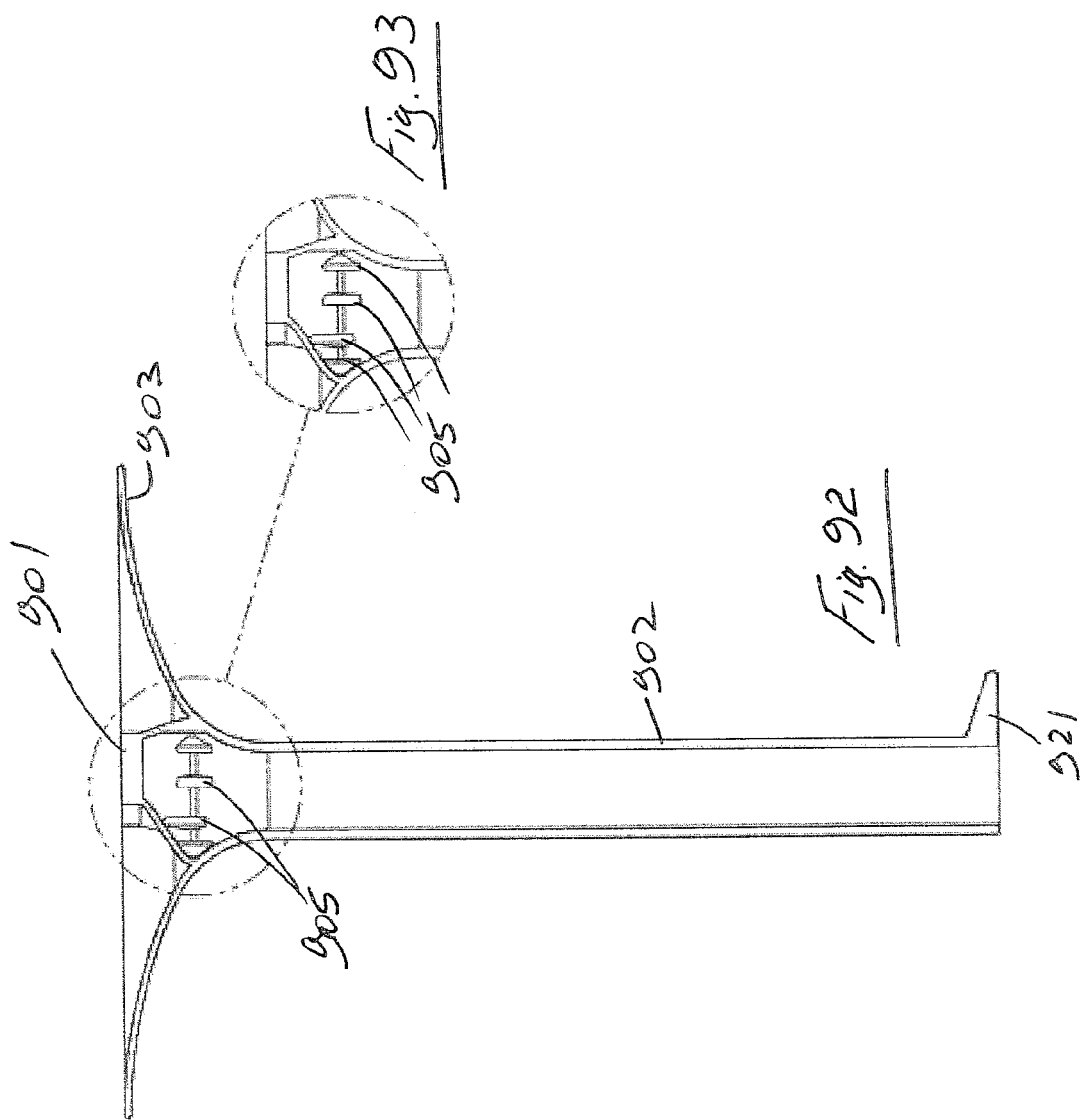

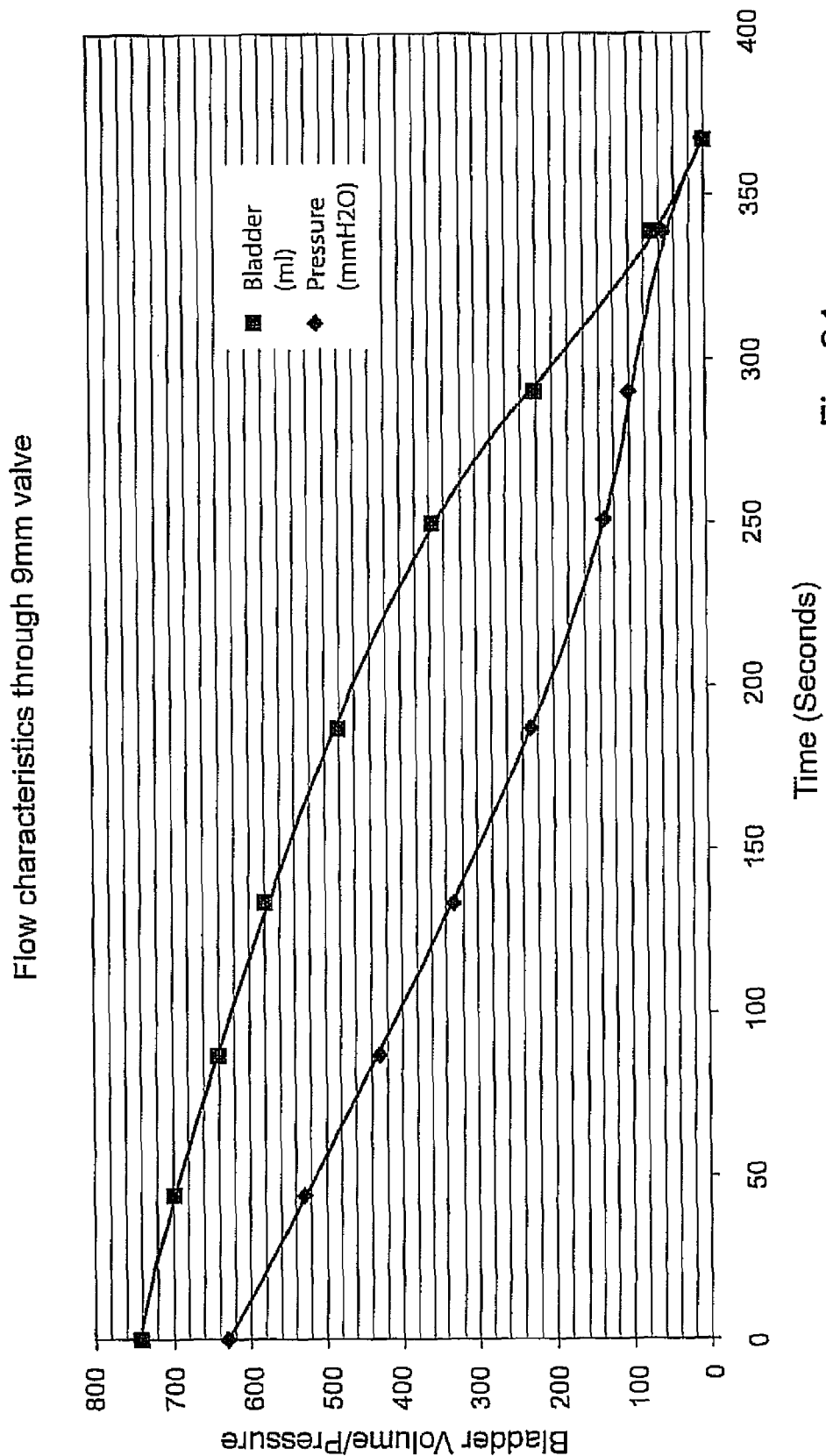

Prior Art
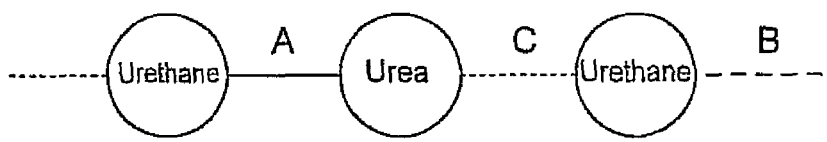
——— Homopolymer A
– – – Homopolymer B
·········· Homopolymer C
*Fig. 97*
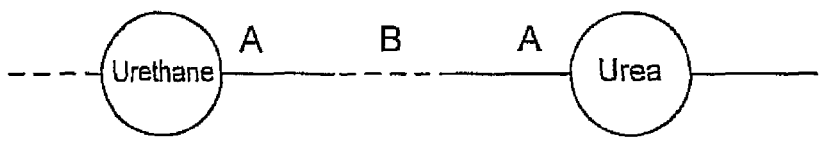
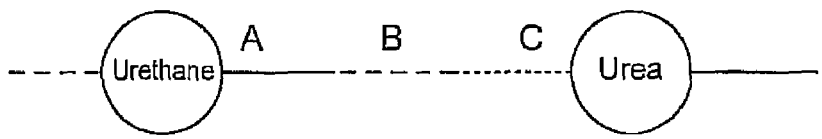
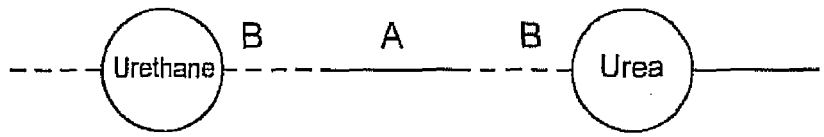
——— Polymer block A
– – – Polymer block B
·········· Polymer block C
*Fig. 98*

UROLOGICAL DEVICE

CROSS-REFERENCE TO RELATED APPLICATIONS

The present application claims the benefit of U.S. Provisional Patent Application Nos. 61/287,838, filed Dec. 18, 2009; and 61/409,741 filed Nov. 3, 2010, the entire contents of which are incorporated herein by reference.

INTRODUCTION

Prostate Cancer is the most common male malignancy in the Western world. In the U.S. there are approximately 180,000 new diagnoses annually. Each year, 40,000 men with established disease die from prostate cancer.

The main cause of stress urinary incontinence (SUI) in males is radical prostatectomy for cancer. Catalona W J, Carvalhal G F, Mager D E, Smith D S. Potency, continence and complication rates in 1,870 consecutive radical retropubic prostatectomies. J. Urol. 1999 August; 162(2):433-8 report that the incidence of SUI 1 yr post radical prostatectomy is 20%.

Lee W R, Schultheiss T E, Hanlon A L, Hanks G E. Urinary incontinence following external-beam radiotherapy for clinically localized prostate cancer Urology. 1996 July; 48(1): 95-9 report that adjuvant radiotherapy of prostate cancer can also affect treatment of SUI.

There is a need for a urology device that will improve patient quality of life by effectively providing a patient controlled device that removes the need for a urine bag and also facilitates normal social functioning.

STATEMENTS OF INVENTION

According to the invention there is provided a urological device comprising a urological valve, the valve comprising a plurality of valve leaflets, the valve having a region of co-aption between the valve leaflets, the valve having a normally closed configuration in which the valve leaflets are engaged at the region of co-aption and an open configuration in which the leaflets are separated at the co-aption region for fluid flow through the valve, the valve being automatically movable from the closed configuration to the open configuration in response to applied urological pressure.

In one embodiment the valve is of a viscoelastic polymeric foam material.

In one case the valve leaflets evert on movement between the closed and the open configuration in response to applied urological pressure.

The valve may be adapted to open in response to a preset pressure applied over a preset time.

The valve may be adapted to open in response a pressure of at least 750 mm $H_2O$ applied for at least 5 seconds.

In one embodiment the valve is adapted to remain closed in response to a spike pressure applied for a short time as would be generated by a user coughing. The spike pressure may be 900 mm $H_2O$ applied for a period of less than 0.5 seconds.

In one embodiment the valve remains open as fluid flows therethrough without a requirement for a user to apply urological pressure. The valve may return to the closed configuration when flow through the valve has substantially stopped.

In one case the valve everts on movement from the closed to open configuration. The valve may revert on return from the open to the closed configuration.

In one embodiment the valve comprises at least three valve leaflets. There may for example be six valve leaflets.

The valve may comprise a main body having a region which defines a hinge about which portion of the valve main body is movable between the closed and open configurations.

In one embodiment the valve comprises stiffening means. The hinge region may be at least partially defined adjacent to the stiffening means.

In one embodiment the urological device comprises a support for the valve. The support may be generally cylindrical. In one case the support is of the same material as that of the valve. In one embodiment the valve and support are integrally moulded.

The urological device may comprise a first retainer for locating the device in the bladder. The first retainer may comprise a flare extending radially outwardly of the support. The first retainer may be of the same material as that of the support.

In one case the first retainer, the support and the valve are integrally moulded.

The urological device may comprise stiffening means for the first retainer. The retainer stiffening means may be of a shape memory material such as Nitinol.

In one embodiment the urological device comprises a second retainer to prevent proximal migration of the device. The second retainer may comprise a meatal tab. The second retainer may comprise a bulbous region of compressive material.

In one embodiment the urological device comprises an antimicrobial coating.

In one case the device comprises a support to which the valve is mounted. The support may be adapted for mounting in a urinary tract. The support may comprise a generally tubular member. The tubular member may comprise a catheter.

In one embodiment the urological device comprises an anchor for anchoring the support and valve in situ.

In some cases the device comprises a housing for the valve, the housing having an inlet on one side of the valve and an outlet on the opposite side of the valve. The inlet may be adapted for mounting to a catheter such as a Foley catheter. The outlet may be adapted for mounting to a drainage bag.

In one case the urological device comprises a collar to support the valve in the housing. The valve may comprise a valve body and the collar is arranged to engage the valve body to control the pressure at which the valve moves from the open to the closed configuration and/or from the closed to the open configuration.

The invention also provides a drainage catheter system comprising a valve, the valve having:—
  a normally closed configuration in which the valve is closed; and
  an open configuration in which the valve is opened for flow through the valve;
  the valve being automatically movable from the closed to the open configuration for flushing of the catheter.

The valve may be a one-way valve. The valve may be movable from the closed to the open position in response to a predefined yield pressure. The valve may be of a biocompatible viscoelastic foam material.

In one case the catheter comprises a urological catheter.

According to the invention there is provided a urological device comprising a urological valve having:—
  a normally closed configuration in which the valve is closed; and
  an open configuration in which the valve is opened for flow through the valve;
  the valve being movable from the closed to the open configuration in response to applied urological pressure.

In one embodiment the device comprises a support to which the valve is mounted.

In one case the support is adapted for mounting in a urinary tract.

The support may comprise a generally tubular member. The tubular member may comprise a catheter.

In one embodiment the device comprises an anchor for anchoring the support and valve in situ.

In one aspect the valve everts on movement between the closed and the open configuration in response to applied urological pressure. On reduction of urological pressure to a preset pressure the valve returns from the open to the closed configuration.

In another aspect the device comprises a housing for the valve, the housing having an inlet on one side of the valve and an outlet on the opposite side of the valve. The inlet may be adapted for mounting to a catheter such as a Foley catheter. The outlet may be adapted for mounting to a drainage bag.

In one embodiment the device comprises a collar to support the valve in the housing. The valve may comprise a valve body and the collar is arranged to engage the valve body to control the pressure at which the valve moves from the open to the closed configuration and/or from the closed to the open configuration.

In one embodiment the valve is adapted to open in response to a preset pressure applied over a preset time. The valve may be adapted to remain closed in response to a spike pressure applied for a short time such as would be generated by a user coughing.

The invention also provides a drainage catheter system comprising a valve, the valve having:—
 a normally closed configuration in which the valve is closed; and
 an open configuration in which the valve is opened for flow through the valve;
 the valve being automatically movable from the closed to the open configuration for flushing of the catheter.

In one embodiment the valve is a one-way valve. The valve may be movable from the closed to the open position in response to a predefined yield pressure. The valve may be of a biocompatible viscoelastic foam material.

In one embodiment the valve comprises a polymeric valve body having an outer support rim, at least three valve leaflets, and a main body region extending between the support rim and the valve leaflets.

The invention also provided a luminal valve for placing in a body lumen comprising at least four valve leaflets, the valve having a normally closed configuration in which the leaflets are engaged and an open configuration in which the leaflets are open. There may be at least five valve leaflets. There may be six valve leaflets.

The valve may comprise a valve body of polymeric material. The valve may comprise an outer support region. The valve may also have a main body region extending between the support region and the valve leaflets.

In one case the main body region is generally concave between the outer support rim and a region of co-aption of the valve leaflets.

In one case the valve leaflets have a region of co-aption and the valve body is reinforced at the region of co-aption. The valve body may be thickened at the region of co-aption.

The region of co-aption may extend for an axial length of at least 1 mm. The region of co-aption may extend for a depth of from 1 mm to 5 mm.

In one embodiment the support rim of the valve body is reinforced. The support run of the valve may be thickened. In one embodiment the valve comprises three valve leaflets. In another embodiment the valve comprises six valve leaflets.

In one embodiment the polymeric material is stable to gastric fluid for at least 3 months, for at least 4 months, for at least 5 months, for at least 6 months, for at least 7 months, for at least 8 months, for at least 9 months, for at least 10 months, for at least 11 months, or for at least one year.

In one case the polymeric material takes up less than about 5%, less than about 10%, less than about 15%, less than about 20%, less than about 25%, or less than about 30% by weight of water at equilibrium.

In one case the polymeric material of the valve body has a % elongation of from 50% to 3000% or 200% to 1200%.

In one case the polymeric material of the valve body has a tensile strength of from 0.01 to 5 MPa or about 0.1 to 1.0 MPa, or about 0.25 to 0.5 MPa.

In one embodiment the polymeric material has a Young's Modulus of about 0.01 to 0.6 MPa, or about 0.1 to about 0.5 MPa.

In one embodiment the polymeric material of the valve body has a density of from 0.1 g/cm$^3$ to 1.5 g/cm$^3$, or 0.3 to 1.2 g/cm$^3$, or 0.8 to 0.9 g/cm$^3$, or 0.5 to 0.6 g/cm$^3$.

In one embodiment the distance between the proximal end of the support region of the valve body and the distal end of the valve leaflets is less than 50 mm, or less than 40 mm, or less than 30 mm, or less than 25 mm, or less than 20 mm, or less than 15 mm.

In one case the polymeric material of the valve body is of an elastic material.

In another case the polymeric material of the valve body is of a viscoelastic material.

In one embodiment the polymeric material of the valve body comprises a foam. The polymeric material of the valve body may comprise an open cell foam.

In one embodiment the polymeric material of the valve body comprises a polyurethane foam.

In one embodiment the length of the valve from the proximal end of the support region to the distal end of the valve leaflets is less than 50 mm, less than 40 mm, less than 30 mm. The length of the valve may be approximately the same as the outer diameter of the support region of the valve. The length of the valve may be approximately 23 mm.

BRIEF DESCRIPTION OF THE DRAWINGS

The invention will be more clearly understood from the following description thereof given by way of example only, in which:—

FIG. 27 is an isometric view of an external urological valve device according to the invention;

FIG. 28 is another isometric view of the device of FIG. 27;

FIG. 30 is an exploded view of the device of FIGS. 27 and 28;

FIGS. 35 and 36 are cross sectional views of the device of FIGS. 29 to 34 illustrating eversion of the valve and fluid flow;

FIG. 40 is a graph of pressure over time illustrating the pressure applied when the valve is in the configuration of FIGS. 37 to 39;

FIG. 44 is an isometric view of the device of FIGS. 27 to 33 mounted to a catheter;

FIG. 47 is a cross sectional view of a female version of the device and catheter in use;

FIG. 48 is an enlarged view of a detail of FIG. 47;

FIG. 49 is a cross sectional view illustrating a modified male version of the device and catheter in use;

FIG. 50 is an enlarged view of a detailed of FIG. 49;

FIG. 53 is a view of a prior art drainage catheter;

FIG. 54 is an enlarged cross sectional view of detail A of FIG. 53;

FIG. 55 is an enlarged cross sectional view of detail B of FIG. 53;

FIG. 58 is a view of the catheter and valve of FIG. 56 with the valve in an open configuration;

FIG. 59 is an enlarged cross sectional view of detail A of FIG. 58;

FIG. 60 is an enlarged cross sectional view of detail B of FIG. 58;

FIG. 68 is a perspective view of another valve device according to the invention;

FIG. 69 is a cross sectional view of the valve device of FIG. 68;

FIG. 70 is a cross sectional view of the valve device of FIGS. 68 and 69 in situ in a bladder neck;

FIG. 76 is a perspective view of another valve device according to the invention;

FIG. 77 is a cross sectional view of the device of FIG. 76;

FIG. 78 is a perspective view of another valve device according to the invention;

FIG. 79 is a cross sectional view of the device of FIG. 78;

FIG. 87 is a cross sectional view of the device of FIGS. 85 and 86;

FIG. 88 is an enlarged view of a detail of FIG. 87;

FIG. 90 is a perspective view of a further urological device according to the invention;

FIG. 91 is a cut-away view of the device of FIG. 90;

FIG. 92 is a cross sectional view of the device of FIG. 91;

FIG. 93 is an enlarged view of a detail of FIG. 92;

FIG. 94 is a graph illustrating the flow characteristics through a urological device of the invention;

FIG. 97 is an illustration of prior art polymers with urea and urethane linkages interspersed between homopolymer soft segments;

FIG. 98 is an illustration of a polyurethane/urea foam according to the invention with urea and urethane linkages interspersed between triblock copolymer soft segments;

DETAILED DESCRIPTION

Figure 1:
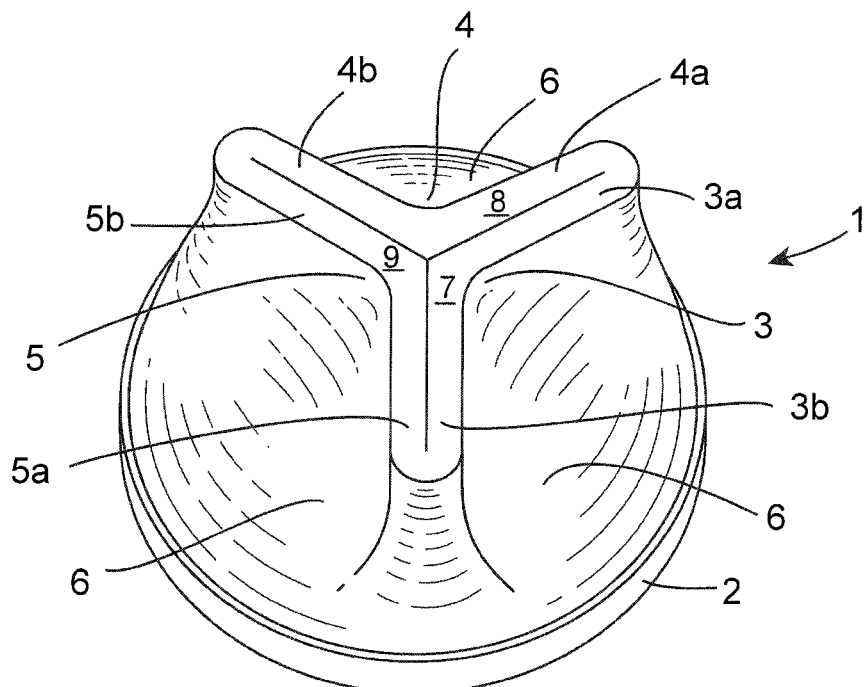
FIG. 1 is an isometric view (from above) of a urological valve according to the invention.
Figure 2:
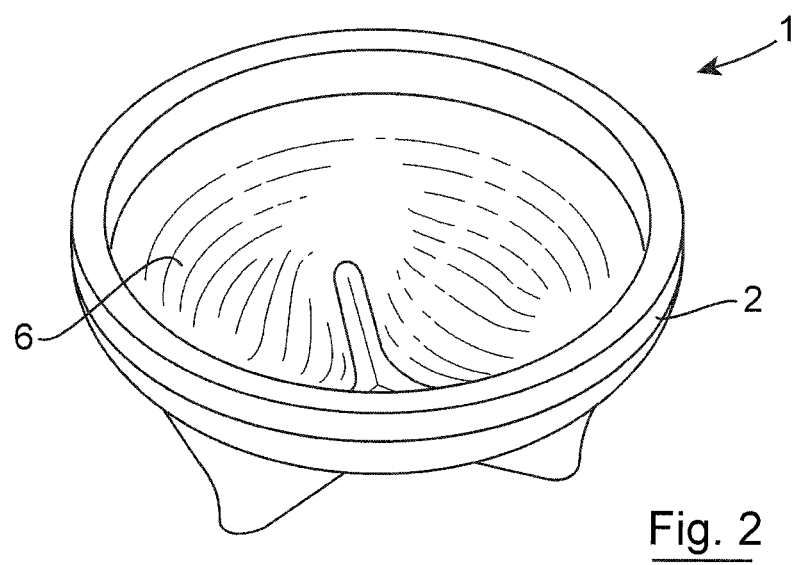
FIG. 2 is an isometric view (from below) of the valve of FIG. 1.
Figure 3:
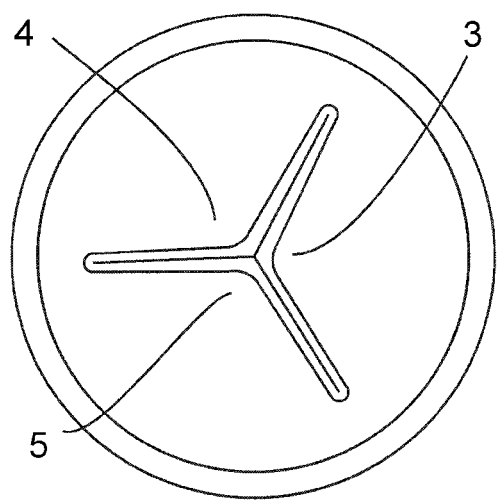
FIG. 3 is an underneath plan view of the valve.
Figure 4:
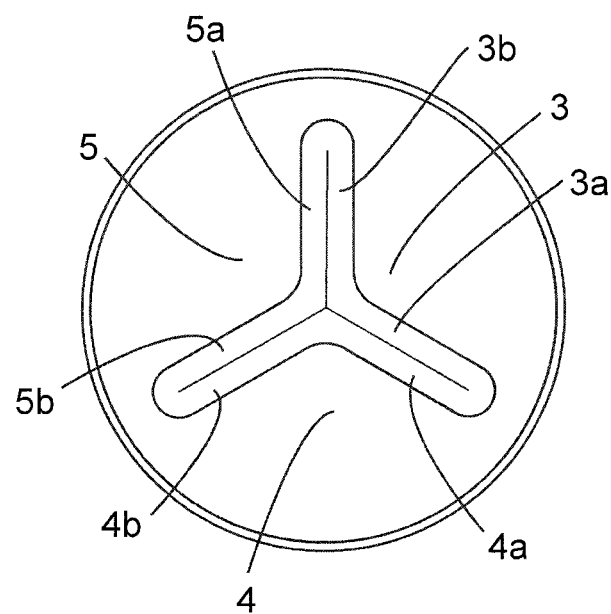
FIG. 4 is a top plan view of the valve.
Figure 6:
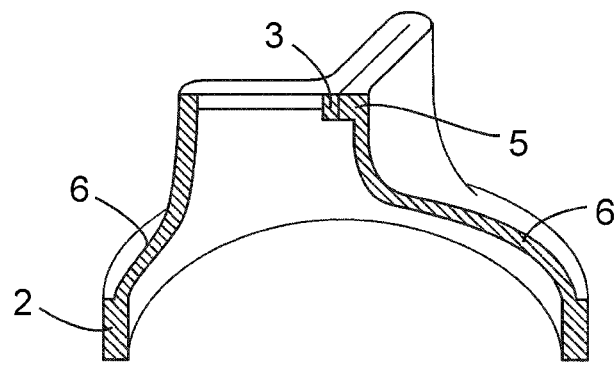
FIGS. 5 and 6 are isometric, partially cut-away sectional, views of the valve.
Figure 5:
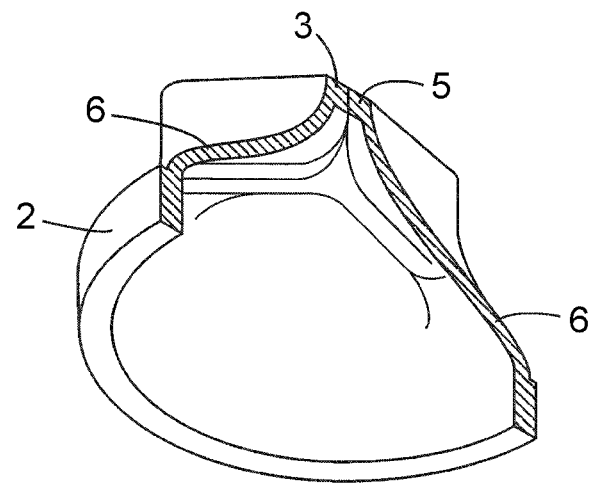
Figure 8:
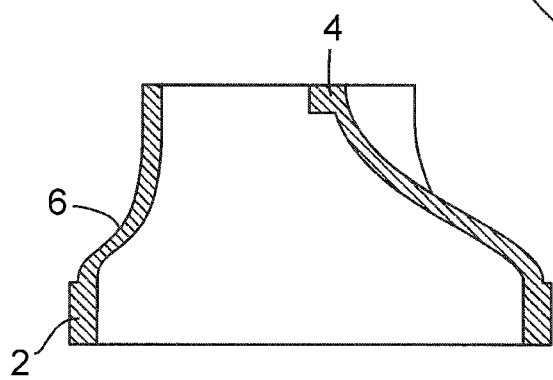
FIGS. 7 and 8 are cross sectional views of the valve.
Figure 7:
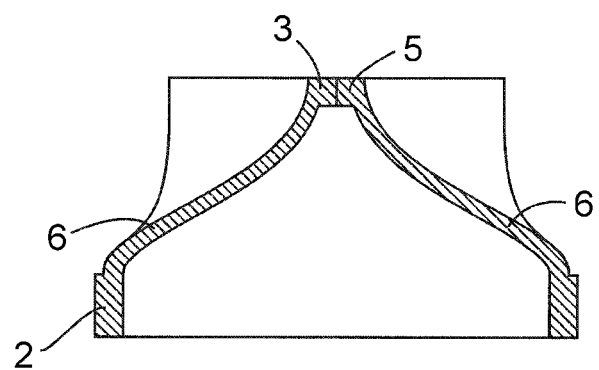

Referring to the drawings and initially to FIGS. 1 to 20 thereof there is illustrated a urological valve 1 which can open automatically in response to applied urological pressure.

The valve 1 comprises a polymeric valve body having an Outer support region with a rim 2, at least three valve leaflets 3, 4, 5, and a main body region 6 extending between the support rim 2 and the valve leaflets 3, 4, 5. The valve leaflets 3, 4, 5 extend inwardly and terminate at end faces 7, 8, 9 respectively. The leaflets 3, 4, 5 each have legs a, b which extend at an included angle of 120° to each other. The adjacent pairs of legs 3a; 4a; 4b; 5b; 5a; 3b; co-apt to close the gap between the valve leaflets when the valve is in the normally closed configuration.

The valve 1 has three configurations. The first configuration is a normally closed configuration in which the valve leaflets 3, 4, 5 co-apt to close the valve. The second configuration is an open configuration to allow fluid flow in which the valve leaflets 3, 4, 5 are opened such that the leaflet leg pairs 3a; 4a; 4b; 5b; 5a; 3b are opened and spaced-apart in response to a force F1 to allow flow through the valve. The third configuration is a second open configuration in response to a force F2.

The various configurations of the valve 1 are illustrated in FIGS. 11 to 20. In the first or normally closed configuration (FIGS. 9, 15) the valve leaflets 3, 4, 5 co-apt.

Figure 11:
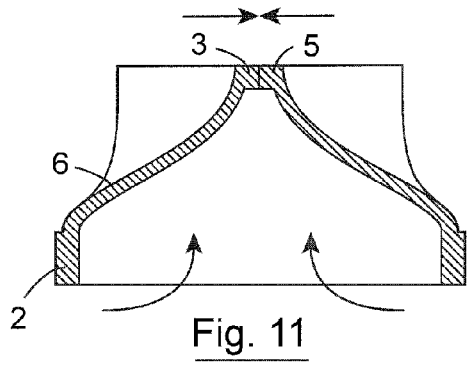
FIG. 11 is a cross sectional view of the valve returned to the closed configuration after opening to flow.
Figure 9:
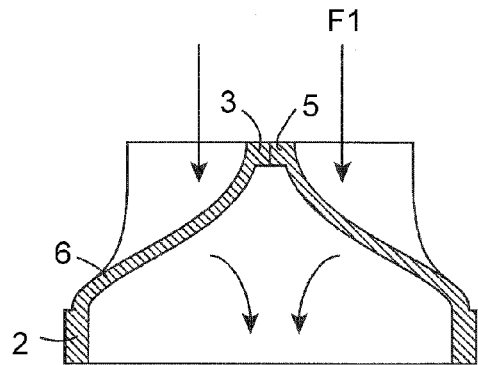
FIG. 9 is a cross sectional view of the valve in a normally closed configuration with a force F1 applied.
Figure 10:
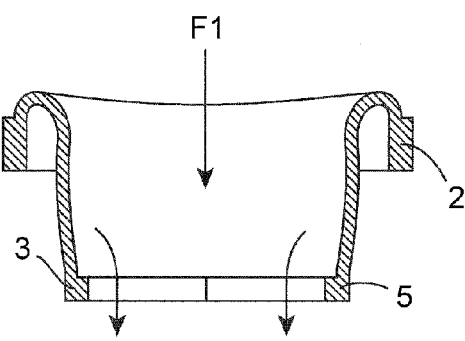
FIG. 10 is a cross sectional view of the valve in an open configuration in response to the force F1.
Figure 14:
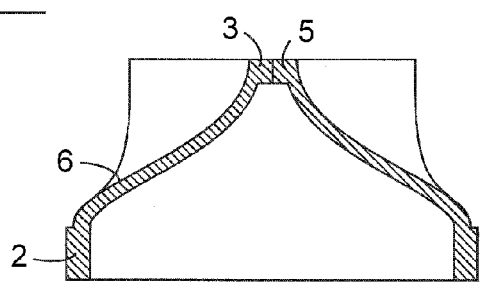
FIG. 14 is a cross sectional view of the valve returned to the closed configuration after opening.
Figure 15:
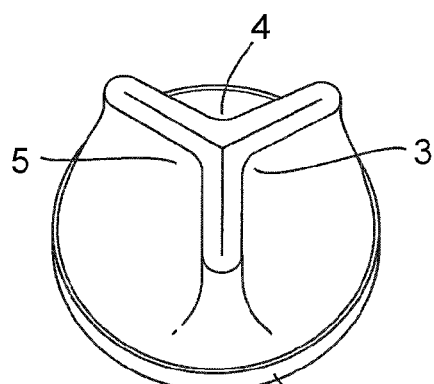
FIG. 15 is an isometric view (from above) of the valve in a normally closed configuration.
Figure 18:
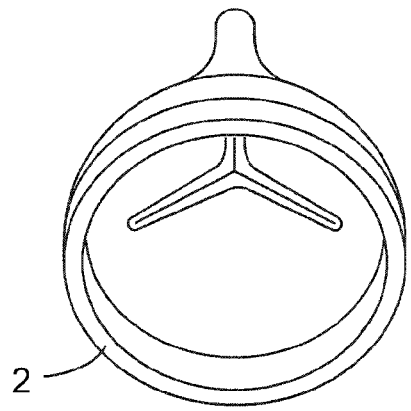
FIG. 18 is an isometric view (from below) of the valve in a normally closed configuration.
Figure 16:
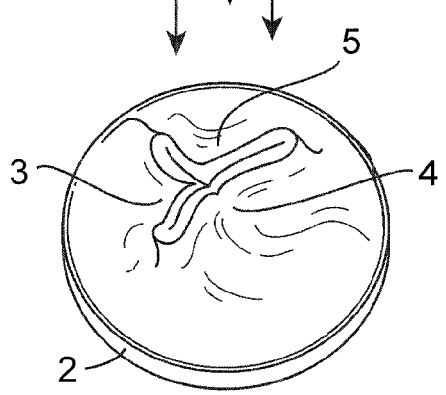
FIG. 16 is an isometric view of the valve moving towards an open configuration in response to the force F1.
Figure 17:
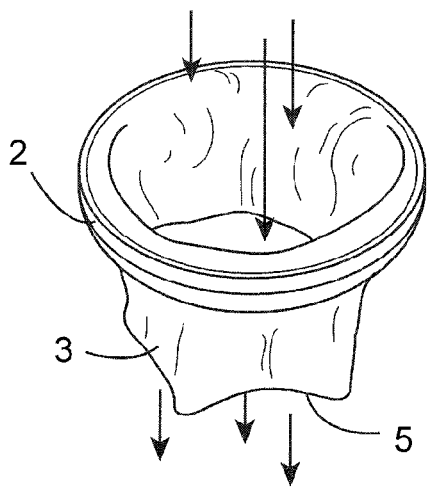
FIG. 17 is an isometric view of the valve in a fully open configuration permitting flow.

When a urological pressure force F1 is applied to the valve body, this force initially pushes the valve leaflets 3, 4, 5 against one another and if the pressure is greater than a set value, the valve body will invert. The start of inversion is illustrated in FIG. 16. When the valve is fully opened in response to force F1 the valve main body (and the leaflets 3, 4, 5) extend downwardly as illustrated in FIGS. 10 and 17. This allows flow to pass through the valve. When the flow is stopped the valve main body will return to the original configuration by everting in response to the biasing of the polymeric material to return to the normally closed configuration with the valve leaflets extending as illustrated in FIGS. 11 and 15.

Figure 13:
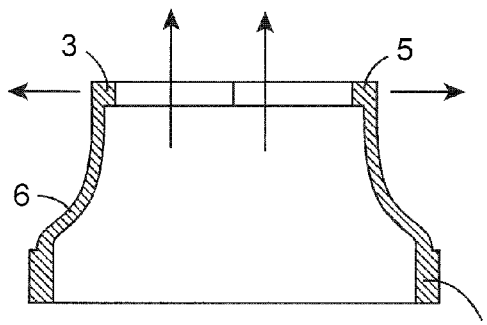
FIG. 13 is a cross sectional view of the valve in an open configuration in response to the force F2.
Figure 12:
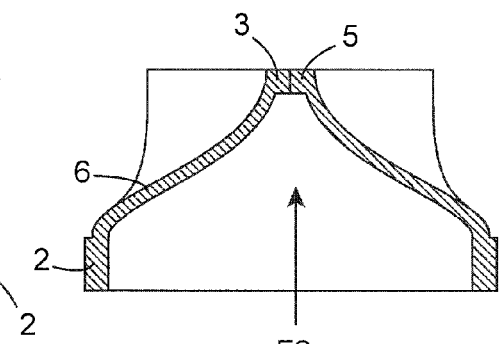
FIG. 12 is a cross sectional view of the valve in a normally closed configuration with a force F2 applied.
Figure 19:
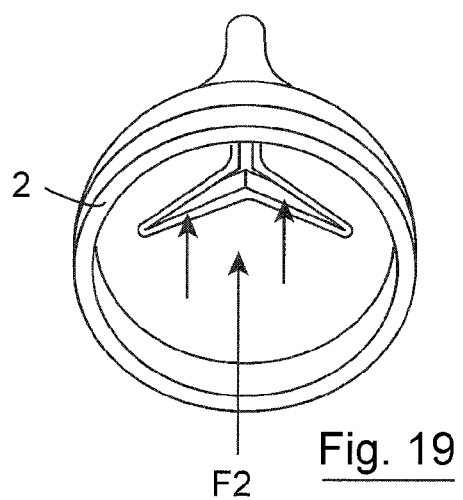
FIG. 19 is an isometric view of the valve in a partially open configuration in response to the force F2.
Figure 20:
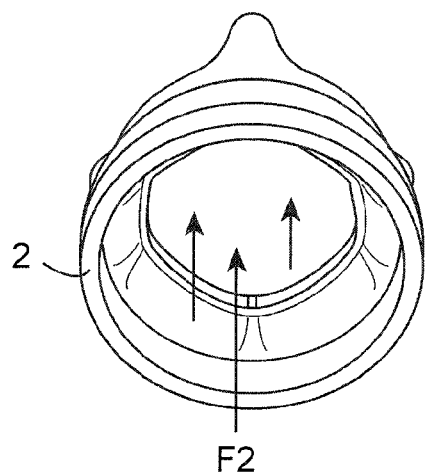
FIG. 20 is an isometric view of the valve in a fully open configuration in response to force F2.

When force F2 is applied to the valve leaflets 3, 4, 5 the leaflet leg pairs 3a; 4a; 4b; 5b; and 5a; 3b open to allow an object to pass (FIGS. 13, 20). FIG. 19 illustrates a partially open configuration in response to a force F2. When the force F2 is removed and the leaflets 3, 4, 5 return to the closed position under the inherent biasing of the polymeric material of the valve body (FIG. 13).

The valve leaflets 3, 4, 5 are reinforced in the region of co-aption. In this case, this is achieved by a local thickening of the polymeric material in this region. Similarly the support rim 2 is reinforced by a local thickening of the polymeric material.

The region of co-aption of the valve leaflets 3, 4, 5 has an axial extent which is typically from 1 to 5 mm. This ensures positive co-aption of the leaflets across a significant interfacial area when the valve is in the normally closed configuration. The thickness of the leaflets at the region of co-aption is typically between 0.1 mm and 10 mm.

The valve 1 is a two-way valve. Different forces are required to open the valve from the opposite directions. The valve 1 requires different forces to open in the different directions. By varying the properties (such as density) of the material of the valve the valve can be tailored to accommodate varying yield pressures. The valve accomplishes this by controllably inverting when placed under pressure.

The valve 1 of the invention returns to its original working position after being fully opened. This is accomplished without damaging the working valve.

When the valve is opened by an applied urological pressure and fluid flow the leaflets open. The outer face of the valve has a greater resistance to change in shape and thus the force required to open main body in this direction is higher.

The important characteristics influencing the functioning of the valve are the leaflet legs that impinge on one another. By varying the geometry and length of the leaflets 3, 4, 5 the valve 1 can be made to open in one direction at different pressures. Opening in the opposite direction is somewhat less dependant on the geometry of the leaflets and more dependant on the elasticity and density of the material the device is made from. Additionally, the overall diameter and the diameter to which the leaflets open influence the opening force in both directions.

The valve may be of any suitable biocompatible polymeric material. It may be of a biocompatible polymeric material having properties which allow the valve to function as described.

The materials used for the production of this valve have a % elongation between 50% and 3000%. The material also has a tensile strength of between 0.01 and 5 MPa. Additionally the material could have an antimicrobial action to prevent colonisation when in-vivo. Additionally the material can be elastic or viscoelastic and can optionally be an open cell foam. The density of the material should be between 0.1 g/cm$^3$ to 1.5 g/cm$^3$.

The valve may have any desired number of leaflets, for example the valve 30 illustrated in FIGS. 21 to 26 has six valve leaflets 251. These leaflets 251 are oriented perpendicular to direction of flow to additionally allow greater distensibility of the valve aperture.

The valve 30 is similar to the valve described above and comprises a polymeric valve body having a proximal outer support region with a rim 32, six valve leaflets 33, and a main body region 36 extending between the support rim 32 and the valve leaflets 33. The valve leaflets 33 terminate at distal end faces. The leaflets each have legs which extend at an included angle of 60° to each other. The adjacent pairs of legs co apt to close the gap between the valve leaflets 33 when the valve is in the normally closed configuration.

The valve 30 has three configurations. The first configuration is a normally closed configuration in which the valve leaflets 33 co-apt to close the valve. The second configuration is an open configuration to allow fluid flow in which the valve leaflets 33 are opened such that the leaflet leg pairs are opened and spaced-apart in response to a force F1 to allow flow through the valve 30. The third configuration is a second open configuration in response to a force F2 which is substantially larger than the antegrade force F2.

The various configurations of the valve 30 are illustrated in FIGS. 21 to 26. In the first or normally closed configuration (FIG. 21) the valve leaflets 33 co-apt.

Figure 21:
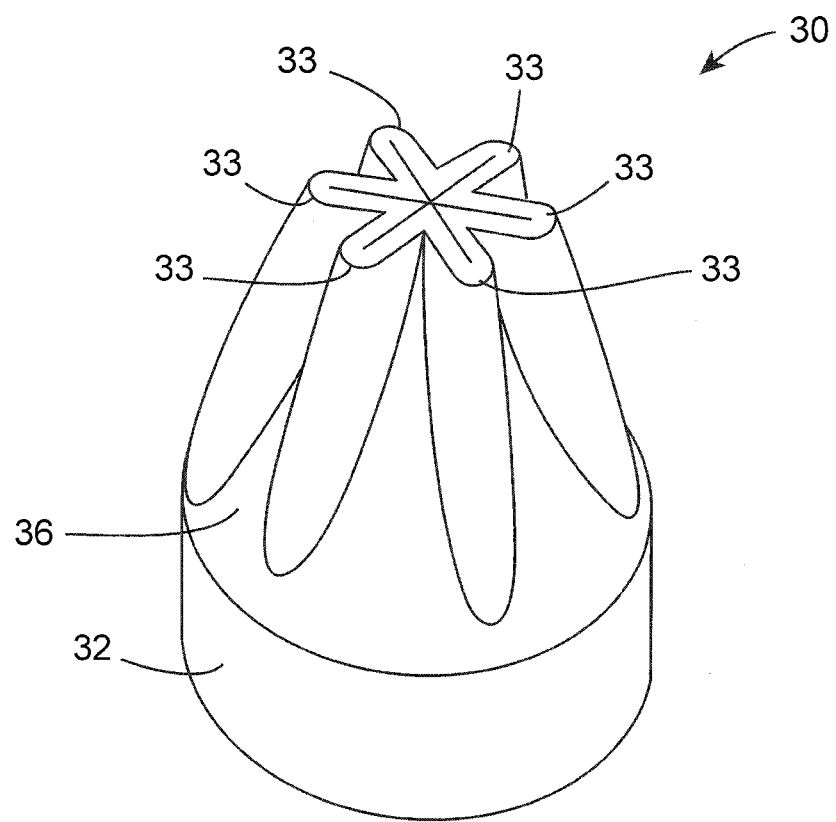
FIG. 21 is an isometric view of another valve according to the invention.
Figure 23:
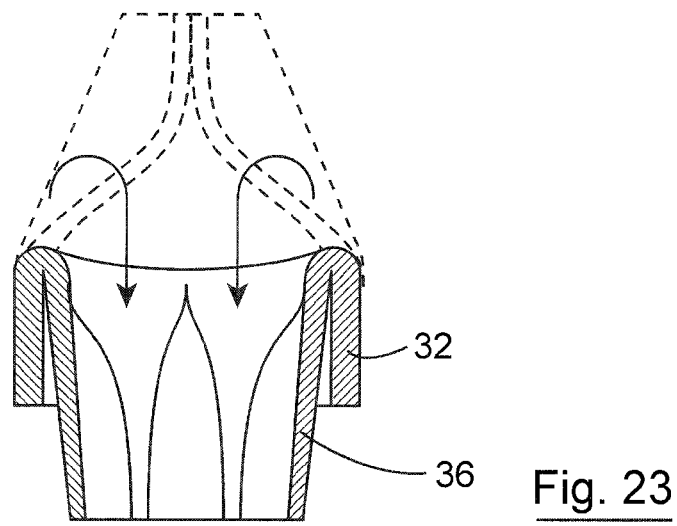
FIG. 23 is a cross sectional view with the valve in the open configuration in response to a urological pressure F1.
Figure 22:
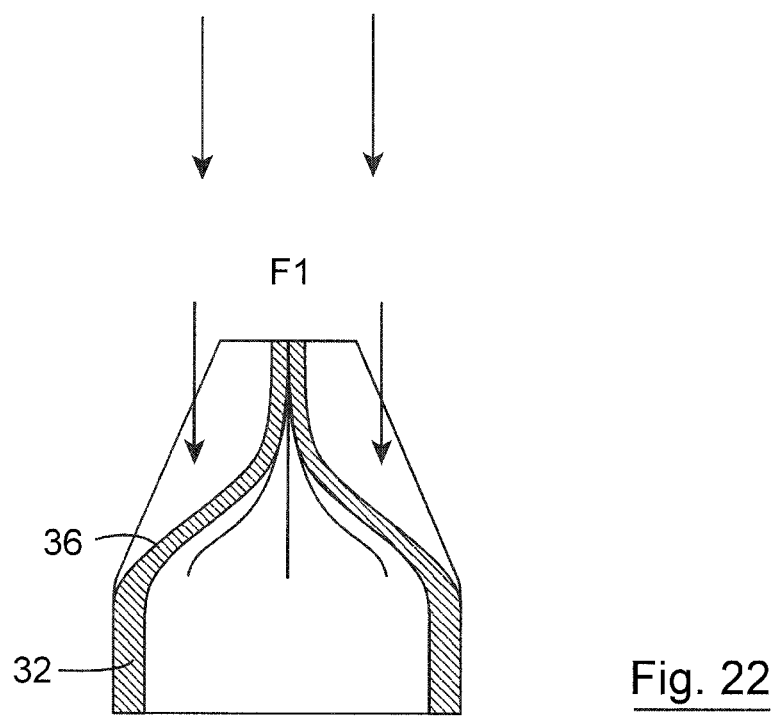
FIG. 22 is a cross sectional view of the valve in a closed configuration.

When a urological pressure force F1 is applied to the valve body. This force initially pushes the valve leaflets 33 against one another (FIG. 22) and if the pressure is greater than a set value, the valve body will invert as illustrated in FIG. 23. When the valve is fully opened in response to force $F_1$ the valve main body (and the leaflets 33) extend downwardly as illustrated in FIG. 23. This allows flow to pass through the valve. When the flow is stopped the valve main body will return to the original configuration by everting in response to the biasing of the polymeric material to return to the normally closed configuration with the valve leaflets extending as illustrated in FIG. 21.

Figure 26:
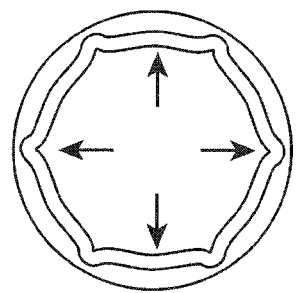
FIG. 26 is a plan view similar to FIG. 25 with the valve in an open configuration.
Figure 25:
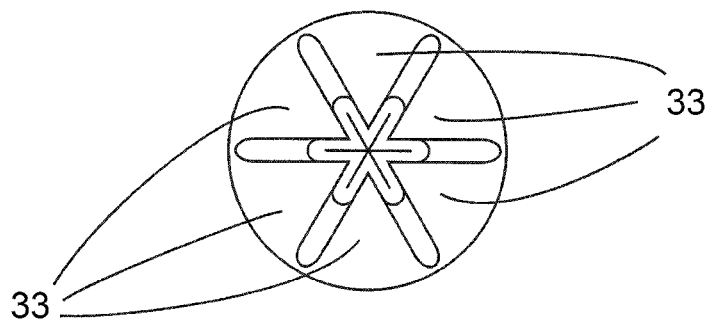
FIG. 25 is a plan view of the device of FIG. 21 with the valve in a closed configuration.
Figure 24:
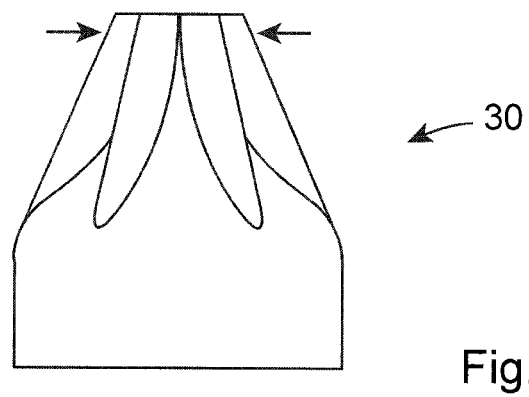
FIG. 24 is an elevational view of the valve of FIG. 21.

When force F2 is applied to the valve leaflets 33 the leaflet legs pairs open to allow an object to pass (FIG. 26). When the force F2 is removed the leaflets 33 return to the closed position under the inherent biasing of the polymeric material of the valve body The valve leaflets 33 are reinforced in the region of co-aption. In this case, this is achieved by a local thickening of the polymeric material in this region. Similarly the support rim 32 is reinforced by a local thickening of the polymeric material.

The region of co-aption of the valve leaflets 33 has an axial extent which is typically from 1 to 5 mm. This ensures positive co-aption of the leaflets across a significant interfacial area when the valve is in the normally closed configuration. The thickness of the leaflets at the region of co-aption is typically between 0.1 mm and 10 mm.

The valve 30 is a two-way valve. Different forces are required to open the valve from the opposite directions. The valve 30 requires different forces to open in the different directions. By varying the properties (such as density) of the material of the valve the valve can be tailored to accommodate varying yield pressures. The valve 30 accomplishes this by controllably inverting when placed under pressure.

The valve 30 of the invention returns to its original working position after being fully opened. This is accomplished without damaging the working valve.

When the valve 30 is opened by user applied urological pressure.

One important characteristic influencing the functioning of the valve 30 is the leaflet legs that impinge on one another. By varying the geometry and length of the leaflets 33 the valve 30 can be made to open in one direction at different pressures. Opening in the opposite direction is somewhat less dependant on the geometry of the leaflets and more dependant on the elasticity and density of the material the device is made from. Additionally, the overall diameter and the diameter to which the leaflets open influence the opening force in both directions.

The valve may be of any suitable biocompatible polymeric material. It may be of a biocompatible polymeric material having properties which allow the valve to function as described.

The materials used for the production of this valve have a % elongation between 50% and 3000%. The material also has a tensile strength of between 0.01 and 5 MPa. Additionally the material could have an antimicrobial action to prevent colonisation when in-vivo. Additionally the material can be elastic or viscoelastic and can optionally be an open cell foam. The density of the material should be between 0.1 g/cm3 to 1.5 g/cm3.

Referring to FIGS. 27 to 58 of the drawings there are illustrated various urological valve devices according to the invention. The devices comprise a valve 600 which may be of the type described above. The valve has a normally closed configuration in which the valve is closed and an open configuration in which the valve is opened for flow through the valve. The valve is movable from the closed to the open configuration in response to applied urological pressure. In some cases the valve 600 everts on movement between the closed and open configuration in response to applied urological pressure. On reduction of urological pressure to a present pressure the valve 600 returns from the open to the closed configuration. The device may be adapted for use in the male or female anatomy. In some cases the valve is mounted to a support. The support may be adapted for mounting in the urinary tract in which case there may be an anchor for anchoring the valve in situ. The valve may be external of the body and may be mounted in a housing having an inlet and an outlet. The inlet may be adapted for mounting to a catheter such as a Foley catheter. The outlet may be adapted for mounting to a drainage means such as a bag or the like.

The invention provides a urological valve device that may be used to treat patients with stress urinary incontinence, for example as a result of a radical prostatectomy. The valve will open based on the pressure applied by the patient through the muscles of the bladder.

In one embodiment the device is for connection to a catheter such as a Foley catheter. The device in this configuration is not intended to be in direct contact with the urethra.

The continence mechanism of the device is a one-way valve that maintains a leak-free system until a pre-defined hydraulic pressure is applied. Once the 'break-pressure' has been reached the lumen of the catheter is open to drain freely. The lumen will remain open until fluid flow has stopped after which the valve will reset itself (this may takes approx 15 sec after cessation of micturition).

The valve is designed to open when a preset pressure is applied to it. The valve is capable of remaining closed at higher pressures if they are not sustained for a prolonged period of time. For example, the valve can be opened by applying a pressure of 750 mmH$_2$O for 5 sec but should remain closed during a pressure of 900 mmH$_2$O over a short time. The valve in this way is insulated from coughing/straining related pressure spikes.

FIGS. 27 and 28 illustrate an external urological valve assembly housing with a fitting 602 for connecting to a Foley catheter at proximal end and a fitting 601 for connecting to a drainage bag at distal end. The housing comprises a proximal section 604 and a distal section 603, which are separable for insertion of a valve 600.

Figure 29:
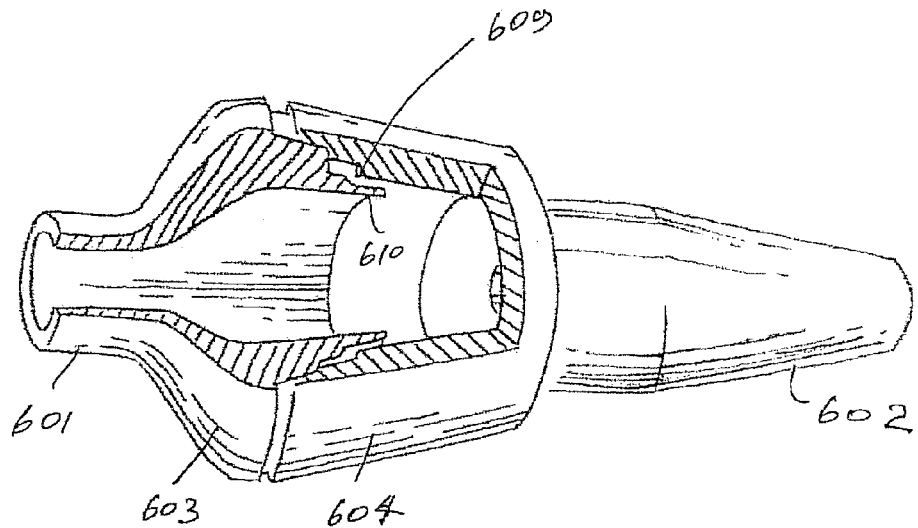
FIG. 29 is an isometric, partially cut-away view of the device of FIGS. 27 and 28 with a valve omitted.
Figure 34:
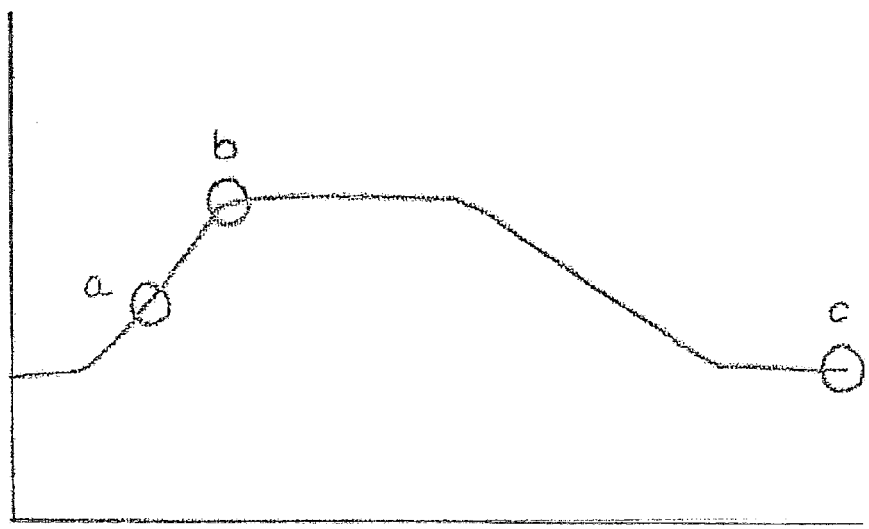
FIG. 34 is a graph of pressure over time illustrating the pressure applied when the valve is in the configurations of FIGS. 31 to 33.

FIG. 29 is a cutaway view of the valve housing without a valve in place. The proximal and distal caps 603, 604 can be seen. An area 609 for seating the valve 600 is illustrated. There is an extended collar 610, which protrudes into the proximal lumen of the valve.

FIG. 30 is an exploded view of valve housing and valve 600, illustrating how the extended collar 610 on the distal cap 602 locates into the lumen of the valve 600.

Figure 33:
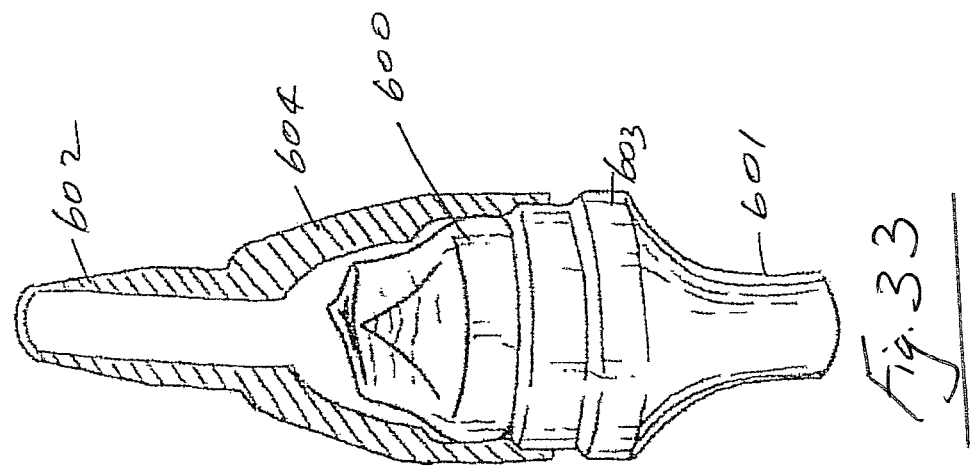
FIGS. 31 to 33 are elevational, partially cross sectional views illustrating the device of FIGS. 27 to 30 in use with the valve in different configurations.
Figure 32:
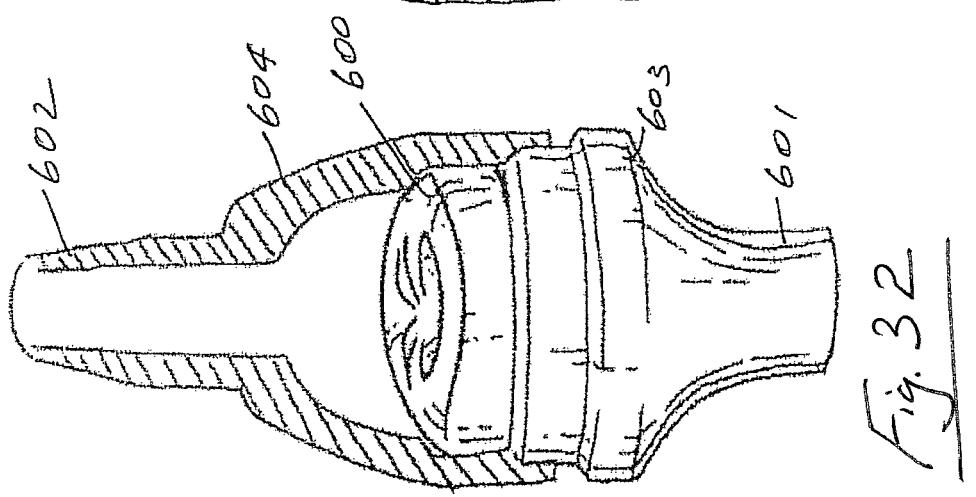
Figure 31:
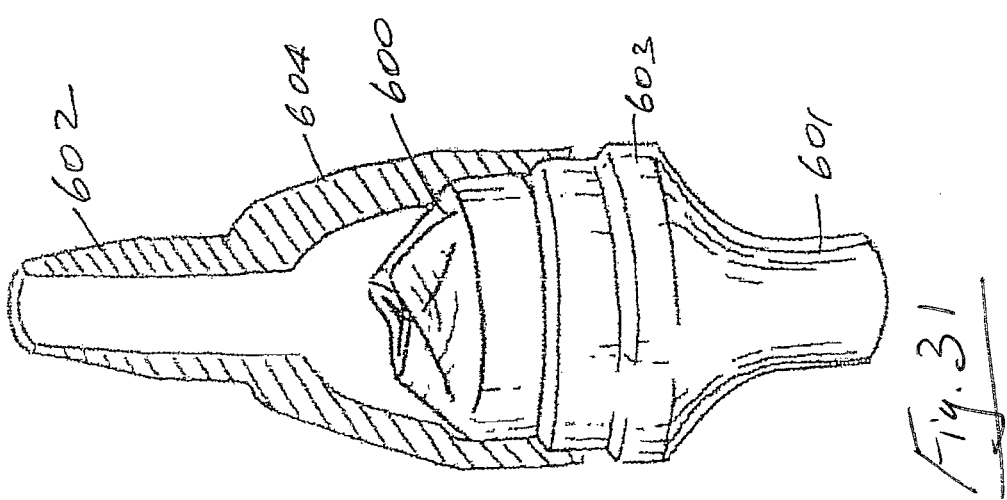

FIGS. 31 to 33 illustrates the functioning of the valve 600 under the influence of hydrostatic pressure. Referring to FIG. 31 as the urethral fluid pressure begins to rise the valve 600 starts to deform slightly. At a predetermined pressure the valve 600 will completely evert thus providing a conducting path for fluid to pass. (FIG. 32) After a predetermined period of time the everted valve 600 will reorient itself to its original position. (FIG. 33) This is graphically illustrated in FIG. 34.

FIGS. 35 and 36 illustrate valve eversion and fluid flow.

Figure 39:
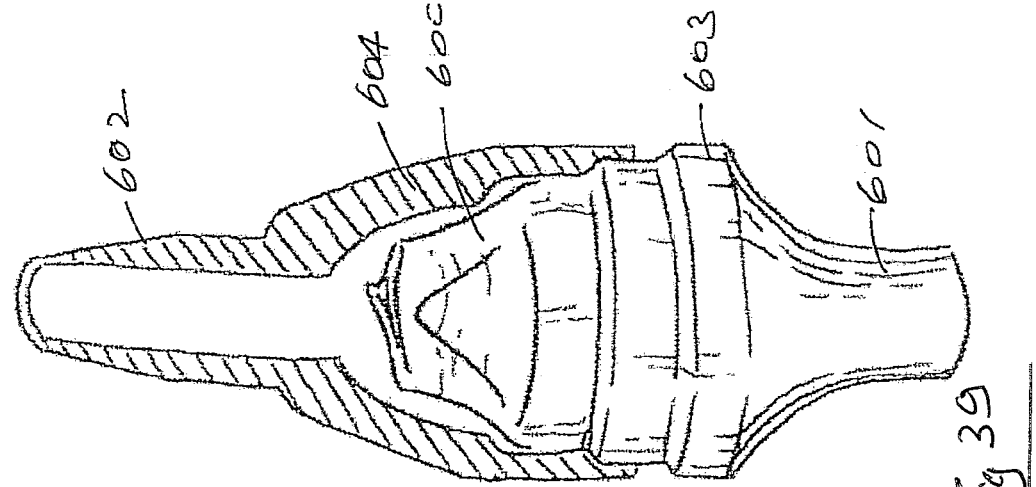
FIGS. 37 to 39 are elevational, partially cross sectional views of the device of FIGS. 29 to 33 and 35 to 36 in use illustrating the functioning of the valve in use when exposed to a rapid pressure spike.
Figure 38:
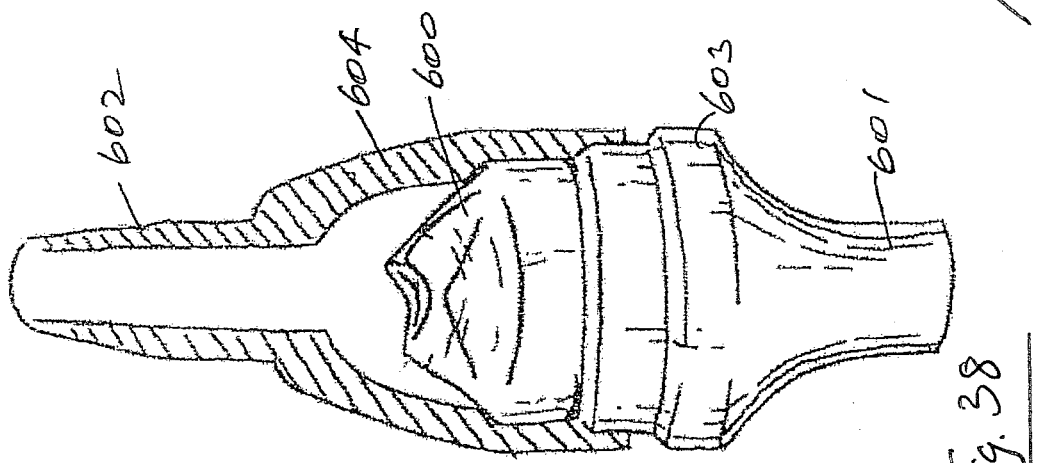
Figure 37:
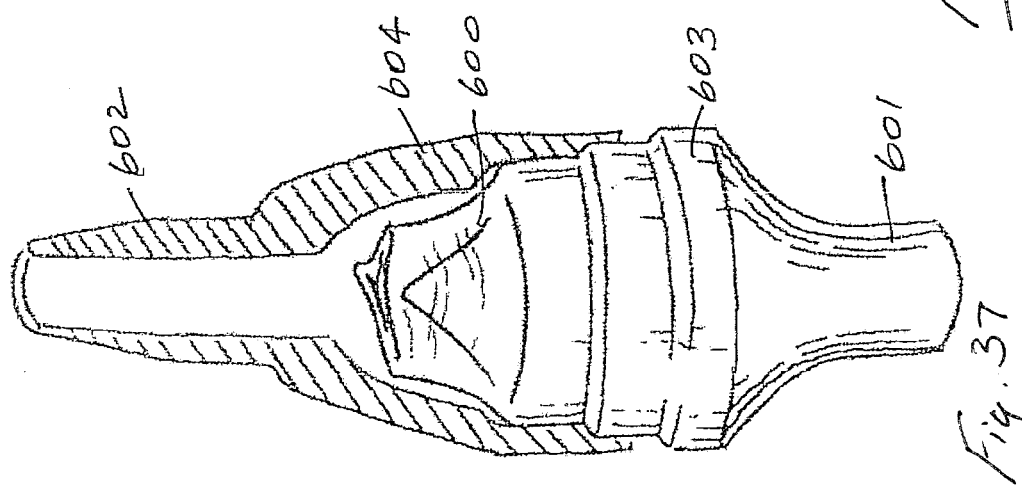

FIGS. 37 to 39 illustrate the functioning of the valve 600 when the valve 600 is exposed to a rapid pressure spike. (FIG. 38) due to a cough or a sneeze may deform momentarily but unless the pressure is maintained will revert to its original configuration. (FIG. 39) In this situation the valve 600 would require a predetermined prolonged time at high pressure to open the valve 600. This is graphically illustrated in FIG. 40.

Figure 42:
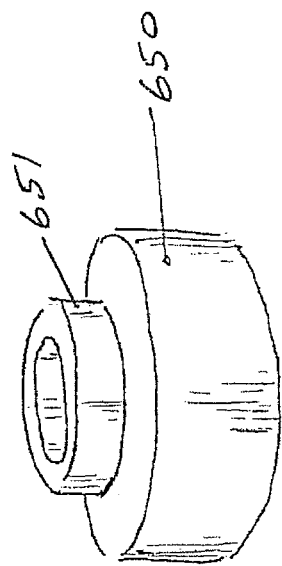
FIG. 42 is an isometric view of a collar used for mounting the valve.
Figure 43:
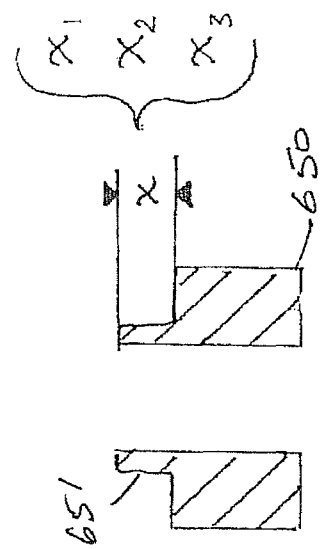
FIG. 43 is a cross sectional view of the collar of FIG. 42.
Figure 41:
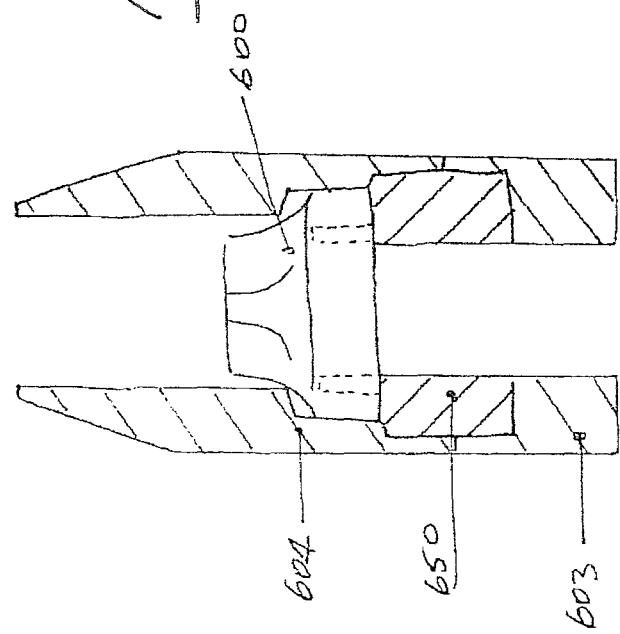
FIG. 41 is a cross sectional view illustrating a valve mounting arrangement.
Figure 45:
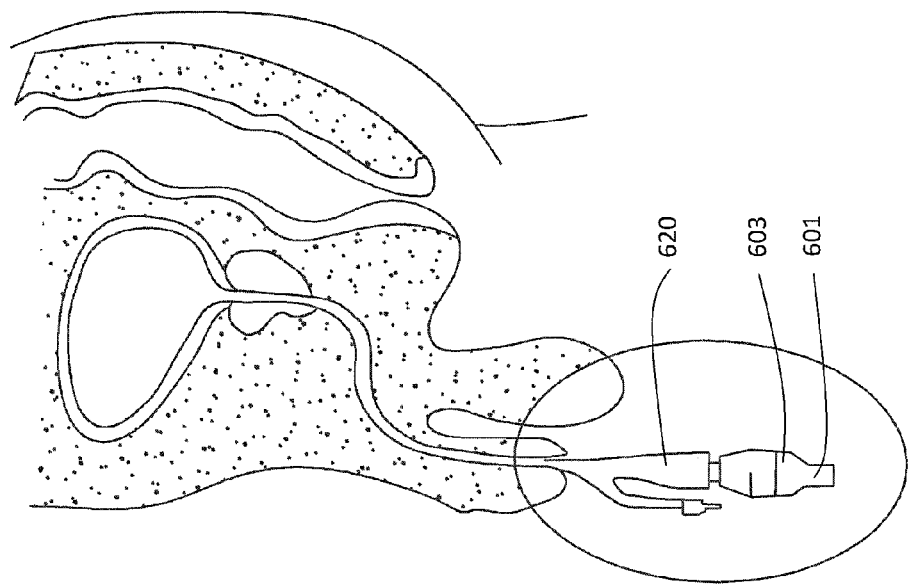
FIG. 45 is a cross sectional view illustrating a male version device and catheter in use.
Figure 46:
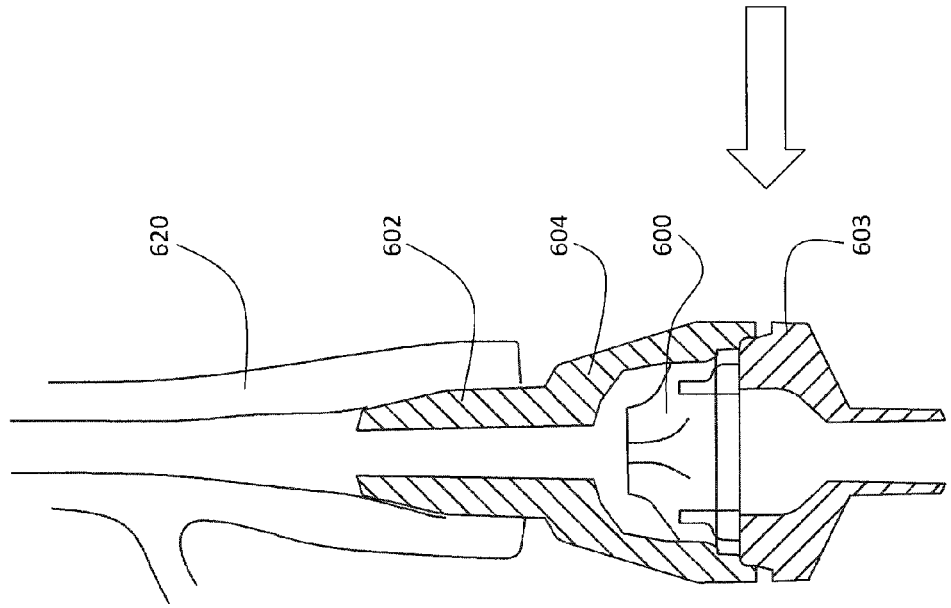
FIG. 46 is an enlarged view of a detail of FIG. 45.
Figure 51:
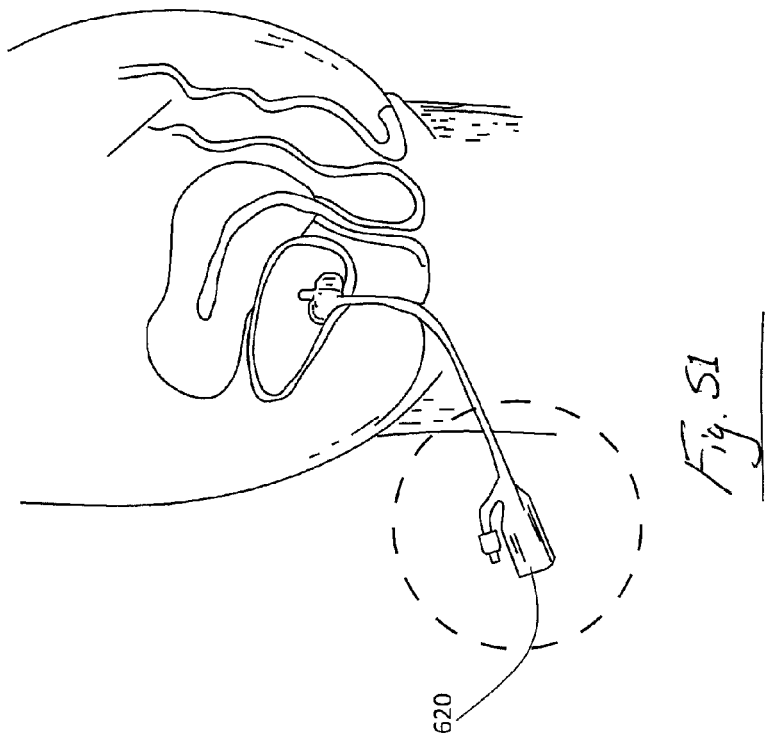
FIG. 51 is a cross sectional view illustrating a modified female version of the device and catheter in use.
Figure 52:
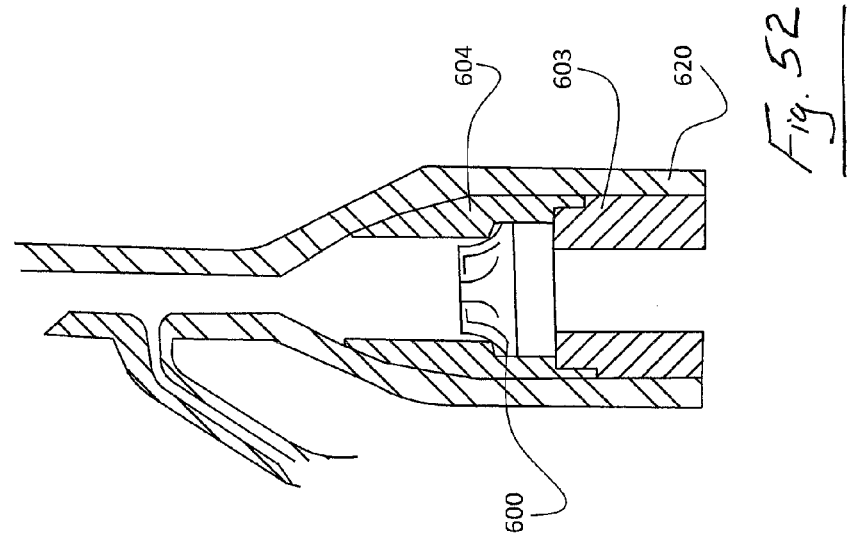
FIG. 52 is an enlarged view of a detail of the device of FIG. 51.

Referring to FIGS. 41 to 43 the mounting of the valve 600 may be controlled using a separate collar component 650 having a projecting part 651 which extends into the rim of the valve body to control the pressure at which the valve 600 moves from the open to the closed configuration and/or from the closed to the open configuration. This can be varied by adjusting the length X of the projection 651. For example, a short length may allow the valve to freely move whereas longer lengths would control the movement of the valve between the closed and open configurations. In this way a single valve may be used for a number of different applications by adjusting the projection 651 length appropriately.

FIGS. 44 to 48 illustrate embodiments of the use of the urology valve attached to a urinary catheter, such as a Foley catheter 620.

FIGS. 49 to 52 are views similar to FIGS. 44 to 48 illustrating an alternative arrangement in which the valve device is incorporated into the proximal housing of the urinary catheter.

The urological valve devices of the invention are in certain embodiments made from a polymeric viscoelastic material. The use of this material addresses a number of problems associated with conventional devices. In the prior art, urological devices have been made from metals and materials that are relatively stiff. These prior art devices, when placed in contact with soft tissues can lead to tissue remodelling, whereby the tissue can become eroded or fibrotic and hardened. In addition, the use of hard materials in contact with soft tissues can result in irritation and subsequently discomfort for the patient.

The urological devices of the invention have features which function using polymeric viscoelastic materials. The viscoelastic polymeric materials form valves, which are normally closed but which can evert on exposure to pressure. The mechanism by which the valves evert is associated with the ability of the material to deform under pressure. The deformation of viscoelastic materials under pressure can also be influenced by the duration over which the pressure is applied.

The material used for may be as described below. The material may also be as described in our application entitled "A biomaterial" Ref: VYSE12 filed on the same date as this application. The entire contents of the VYSE12 application are herein incorporated by reference in its entirety.

The various urological valves described herein may be manufactured from a suitable polymeric viscoelastic material such as described below in example 5 of the material section.

Valves of the type illustrated in FIGS. 28/29 above manufactured from this material were tested for opening pressure and flowrate. The following results were obtained.

| Valve Number | Polymer (g/ml) Density | Leakage (mls) | Opening pressure (mmH2O) | Flowrate (ml/min) |
|---|---|---|---|---|
| 1 | 1.02 | 0 | 817 | 877 |
| 2 | 0.95 | 0 | 703 | 894 |
| 3 | 1.01 | 0 | 877 | 875 |
| 4 | 1.01 | 0 | 803 | 941 |
| 5 | 1.02 | 0 | 877 | 892 |
| 6 | 0.96 | 0 | 820 | 928 |
| 7 | 1.07 | 0 | 945 | 1010 |

The results in the table above illustrate that a number of valves made with a density between 0.95-1.07 g/ml have opening pressures within the required specification but with no leakage when the valve is closed. The flowrate through the valve is also noteworthy as this enables bladder emptying within a reasonable timeframe.

This invention also relates to improvements in devices such as catheters that present a conduit through which bacteria can enter the internal anatomy. In particular, the invention relates to urological drainage catheters. However, the technology described below may also be relevant to long and short term drainage devices such as supra pubic catheters, Percutaneous Endoscopic Gastrostomy (PEG) tubes and other devices that might present a conduit through which bacteria could enter the internal anatomy.

Bacteria external to the body are known to travel rapidly up the urethra leading to urinary tract infections and biofilm formation in the case of indwelling catheters and devices.

The proliferation of *Proteus Miribellis* within urological devices results in the precipitation of salts and minerals from urine resulting in the ultimate encrustation of the device lumen leading to blockage. Although many attempts have been made to use antimicrobial coating to prevent this effect, no long term solution has been found and urinary catheters will become blocked within a 3-4 week period.

The Foley urinary catheter has remained unchanged for the past 60 years. It is widely accepted that 100% of indwelling Foley catheters will become encrusted and block within a 4 week timeframe. A great deal of commercial effort has focused on increasing the longevity of these devices because long term users require specialist nurses to change the devices frequently, which is costly.

There are very large number of disclosures in the prior art teaching the use of a variety of antimicrobial coatings and inserts for use in drainage catheters. U.S. Pat. No. 4,603,152 describes antimicrobial coatings for catheters canulea and the like. U.S. Pat. No. 7,601,361 describes durable antimicrobial coatings. U.S. Pat. No. 4,932,948 describes antimicrobial insert for a male urinary catheter. U.S. Pat. No. 5,782,808 describes an antimicrobial tubing connector.

One problem with the existing technology is that most of the antimicrobial agents are only minimally effective at preventing the proliferation of bacteria and the subsequent encrustation of drainage devices by those bacteria. In addition many of the antimicrobial agents in use can lead to the development of resistance by the bacteria to the agent in use.

Much work has been carried out to coat indwelling catheters with antimicrobial coatings in an effort to prevent biofilm formation. These coatings have either been ineffective or of insufficient durability to sustain the antimicrobial effect.

Referring to FIGS. 53 to 55 there is illustrated a conventional urinary drainage catheter 500 for draining urine from a bladder 501. The catheter comprises a tube 502 having an inlet 503 and an outlet 504 through which urine is drained. The catheter 500 has a bulbous head 505 for retaining the catheter in situ in the bladder. A conventional catheter of this type is generally referred to as a Foley catheter. In use, urine drips from the catheter outlet 504 into a collection bag. Such a catheter suffers from the considerable disadvantage that bacterial colonisation and encrustation adjacent to the inlet 503 and in the catheter lumen can occur, as illustrated in FIGS. 54 and 55 respectively.

Figure 56:
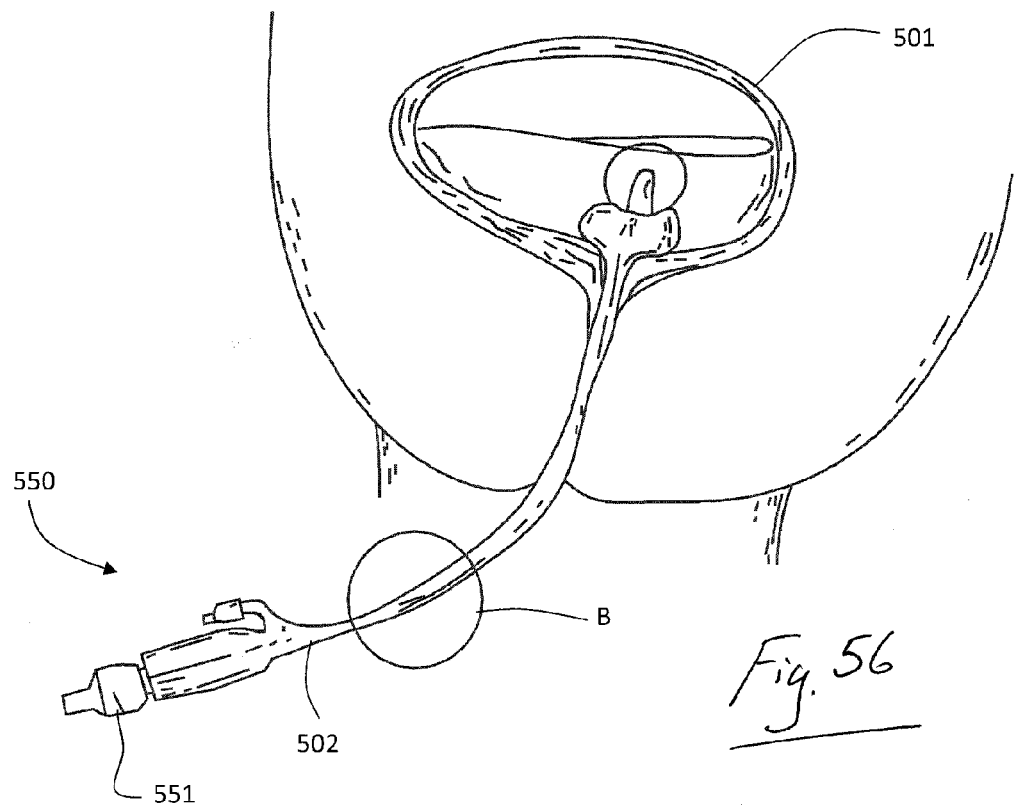
FIG. 56 is a view of a drainage catheter according to the invention in situ, the catheter having a valve in a closed configuration.
Figure 57:
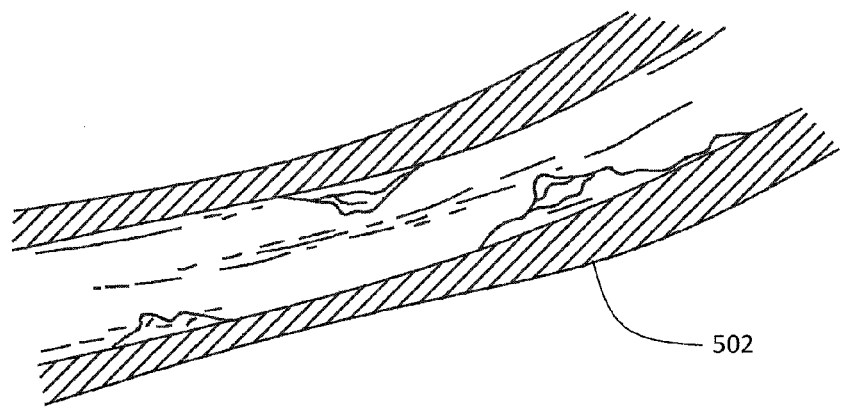
FIG. 57 is a cross sectional view of detail B of FIG. 56.

In the invention, a drainage catheter 550 has a valve 551 to control flow through the catheter. FIGS. 56 and 57 illustrate the catheter 550 when the valve 551 is in a closed configuration. The valve 551 allows the bladder to fill above the level of the catheter inlet 503. While the valve 551 is closed a build up of urine in the catheter lumen may start the process of bacterial biofilm formation and encrustation as illustrated in FIG. 57.

Referring to FIGS. 58 to 60 when the valve 551 is opened voluntarily a pressurised flow of urine through the catheter is generated until the level of urine in the bladder 501 drops below the level of the catheter inlet 503. Regular application of such pressurised flow generates sufficient force to prevent accumulation of bacterial biofilm at the catheter inlet and in the catheter lumen as illustrated in FIG. 59 and FIG. 60 respectively.

In the invention a one way valve is incorporated into a catheter, especially a urinary catheter. The valve is designed not to leak but to open at a predefined yield pressure and return to its closed position following bladder emptying. The predefined yield pressure may correspond to an abdominal force generated by the patient through conscious straining or due to normal movement. The force of standing or sitting alone is known to generate significant abdominal pressures. The valve in this case is designed to be placed in line between the catheter and a urine collection bag. The valve facilitates the cyclic filling and emptying of the bladder and thus regular flushing of the catheter lumen. The emptying of the bladder may be conscious or unconscious due to movement.

This invention teaches a completely different approach to that conventionally used to achieve an antimicrobial effect. In the invention a physical and mechanical means is used to achieve an antimicrobial effect, thus avoiding the need for potentially cytotoxic coatings. In addition this approach represents a durable and sustained effect rather than the transient effect seen with antimicrobial compounds.

Figure 61:
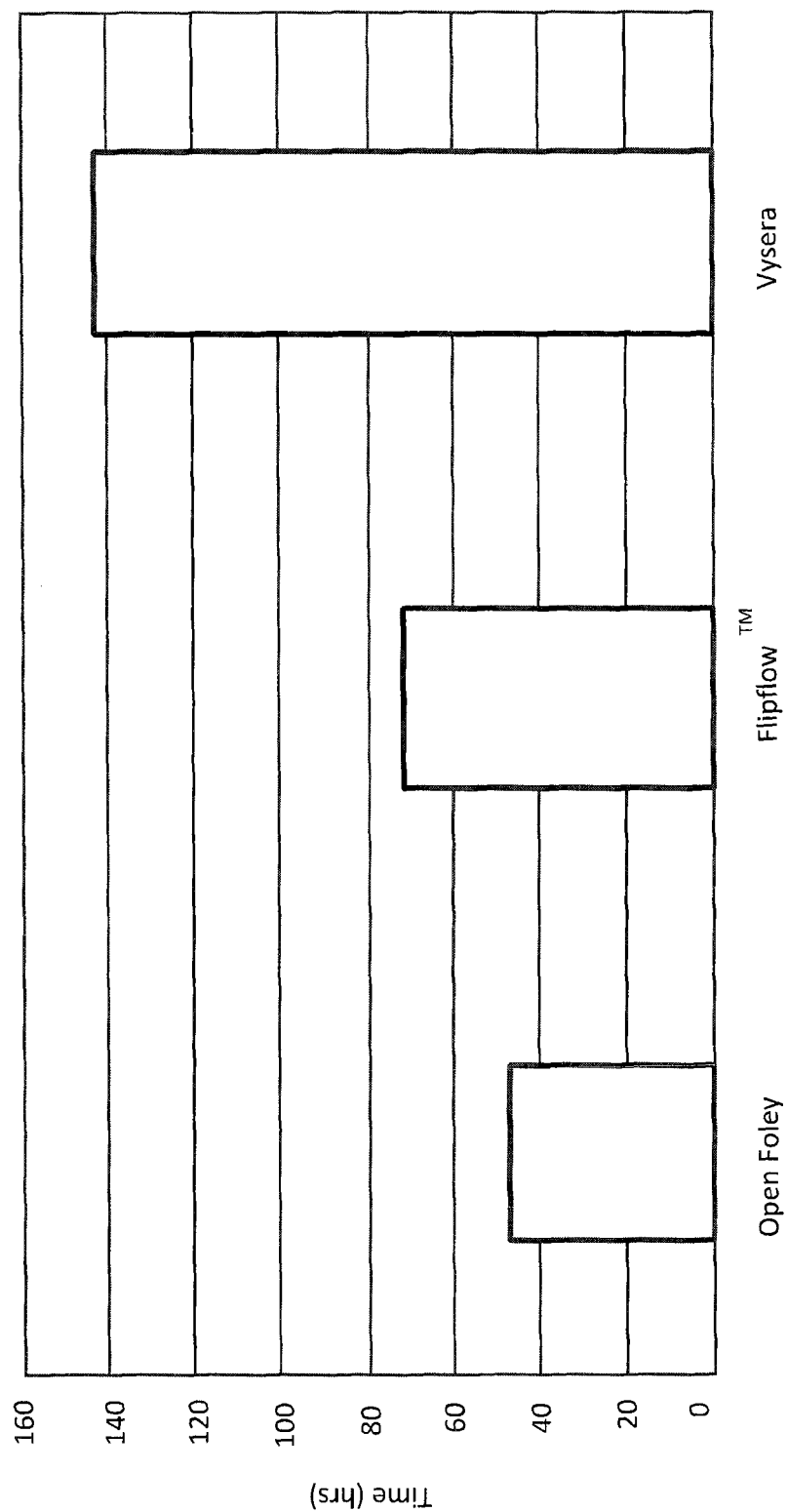
FIG. 61 is a graph of time taken for devices to encrust using an accelerated bacterial culture test.
Figure 63:
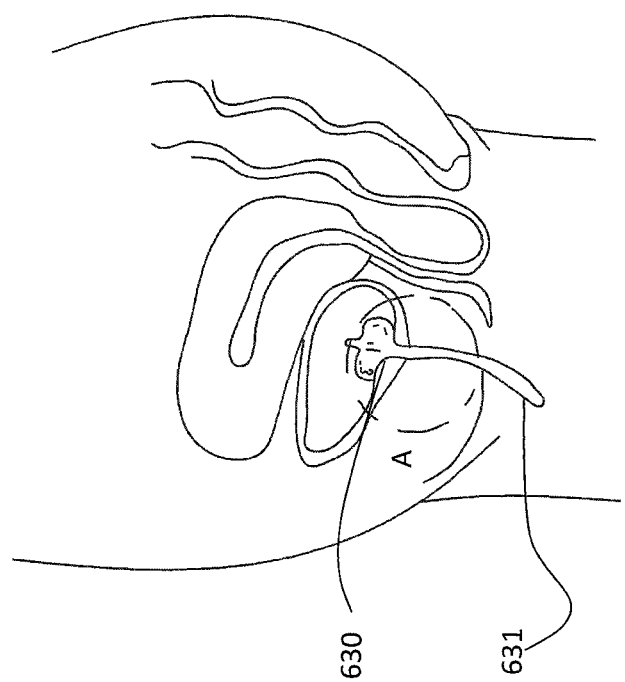
FIG. 63 is an enlarged view of a detail of the device of FIG. 62.
Figure 62:
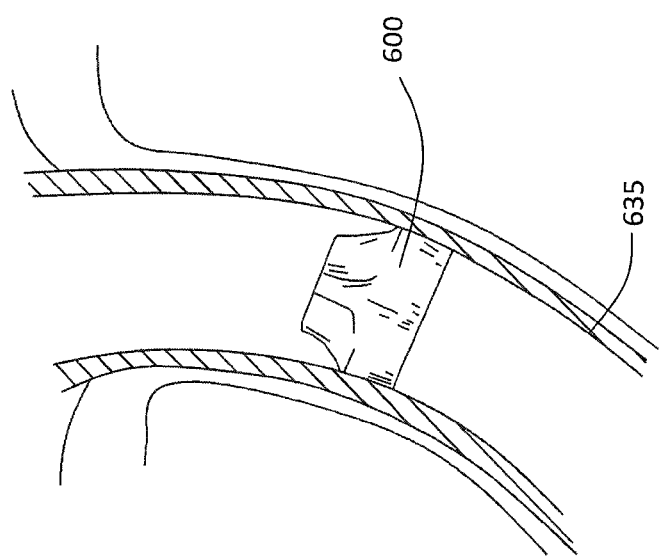
FIG. 62 is a cross sectional view illustrating another female version of the device.
Figure 65:
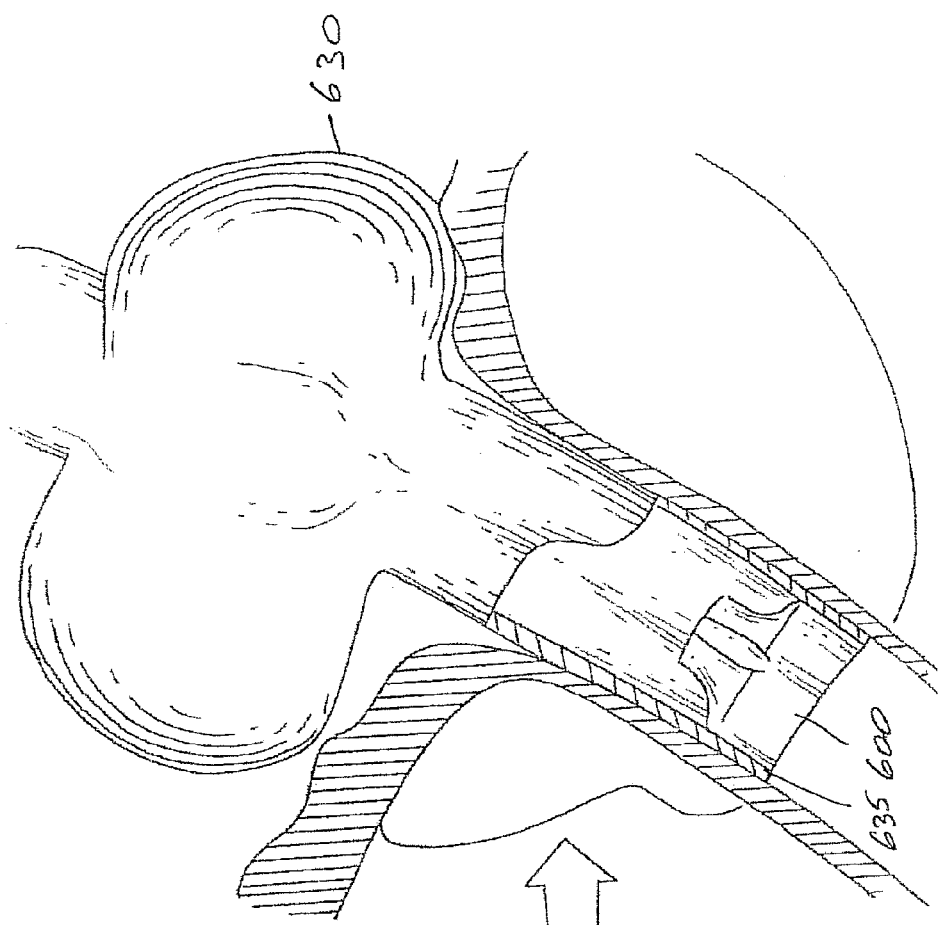
FIG. 65 is an enlarged view of a detail of FIG. 64.
Figure 64:
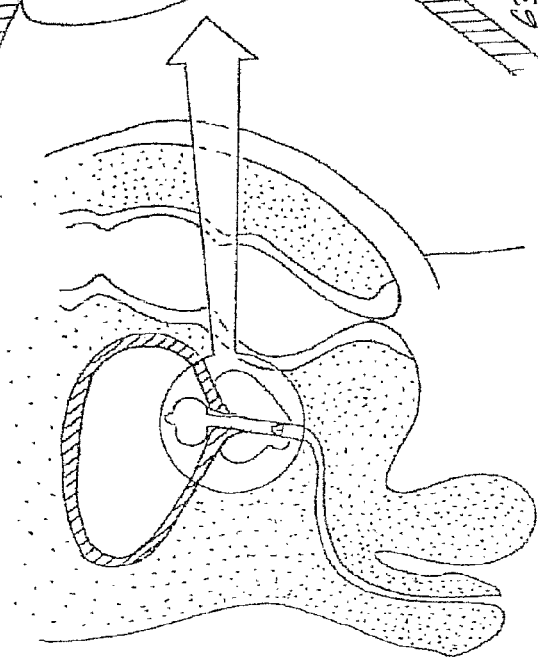
FIG. 64 is a cross sectional view of an internal urological valve device in use.

Accelerated microbial tests (FIG. 61) have demonstrated that incorporation of a tricuspid valve of a biocompatible foam material as described herein into a Foley catheter prolonges the time to encrustation by a factor of almost 4 compared to an open Foley catheter. The valve of the invention also performs very significantly better than a catheter fitted with a ball valve which is manually movable between an open and close configuration. One search prior-art valve is available under the tradename FLIP-FLO.

The invention provides a valve for control of urinary incontinence. The valve opens at a specific bladder pressure, in one case when the bladder is full (or at a required volume), without any manual manipulation. The bladder will then empty into an attached drainage bag and the valve will return to the closed position. This has the benefit of being easy to use. The use of a valve to offer intermittent rather than continual drainage has been shown to potentially reduce catheter blockage.

Those users most likely to suffer from catheter blockages are those that have other co-morbidities, a number of which result in dexterity or mobility.

The valve aids patients who are unable to use a conventional catheter valve but who would still benefit greatly in maintaining 'normal' bladder function by intermittent drainage as opposed to continuous drainage.

In vitro studies in a laboratory model of the catheterised bladder were undertaken to investigate the time to blockage of the valve of the invention in comparison to the 'Flip-flo' (Trade Mark of Bard Inc) valve and continuous drainage model. The bladder model is described by Striker et al in Stickler, D. J., Morris, N. S, and Winters, C. (1999). Simple physical model to study formation and physiology of biofilms on urethral catheters. Methods in Enzymology, 310:494.

The valve of the invention demonstrated a significantly increased length of time to blockage versus a continuous drainage model (110.4 vs. 22.9 hours, p-value 0.001). There was no significant difference between a normally draining 'Flip-flo' valve and a 'Flip-flo' valve assisted by the automated syringe pump (40.0 vs. 45.1 hours, p-value-0.425). The mean time to blockage was 110.4 hours for the valve of the invention compared to 45.1 hours for the automated Flip-flo: This result was highly significant (p-value 0.004).

The bladder model consists of a glass chamber (the bladder) maintained at 37° C. by a water jacket. Each model was sterilised by autoclaving and then a size 14 ch Romed catheter, latex based was inserted into the bladder chamber through a section of silicon tubing (the urethra) at the base of the model. Catheters were secured in place at the outlet of the bladder by inflation of their balloons with 10 ml of deionised water. Where appropriate, the end of the catheters were then attached to either a valve of the invention, Flip-flo valve or left open for continuous drainage. The Flip-flo valve and the continuous drainage models were then subsequently connected to drainage bags in the normal way but the valve of the invention and automated Flip-flo valve were left to drain into a covered plastic beaker (to allow for an open system due to the pressures applied from the syringe pump). Sterile urine was pumped into the chambers so that residual volumes collected below the catheter eye-holes before flowing through the drainage tube to the collection bags/beaker.

Flip-flo valves were attached to normal Foley catheters with and without an automated syringe pump and intermittently opened every four hours over a 12 hour period and then both switched to continuous drainage overnight, until blockage occurred. In normal use, a Flip-flo valve would be used for intermittent drainage during the daytime and continuous drainage at night. This regime was used in the tests to reproduce normal use as much as possible.

Valved catheters according to the invention provide the patient with a number of advantages: firstly unsightly drainage bags do not have to be continually worn throughout the day, and secondly it also helps retain some bladder tone because the bladder fills and empties periodically, as is the case in a 'normal' bladder. Additionally the periodic flushing of urine through the catheter displaces some of the developing biofilm, which ultimately causes catheter blockage, and hence increases the life-span of the catheter. The Vysera valve offers additional benefits, such as increasing the number of potential users to include those with dexterity or mobility difficulties and increase the life-span of the catheter by permitting intermittent drainage to occur overnight as well as during the day.+

FIGS. 62 to 65 illustrate a urology valve in an indwelling valve device 600 to be retained using a balloon 630 or other anchor in the bladder. The valve 600 may be mounted to a tubular support 635. There may be a pending tether 631 for recovery of the valve 600 externally.

Figures 66, 67:
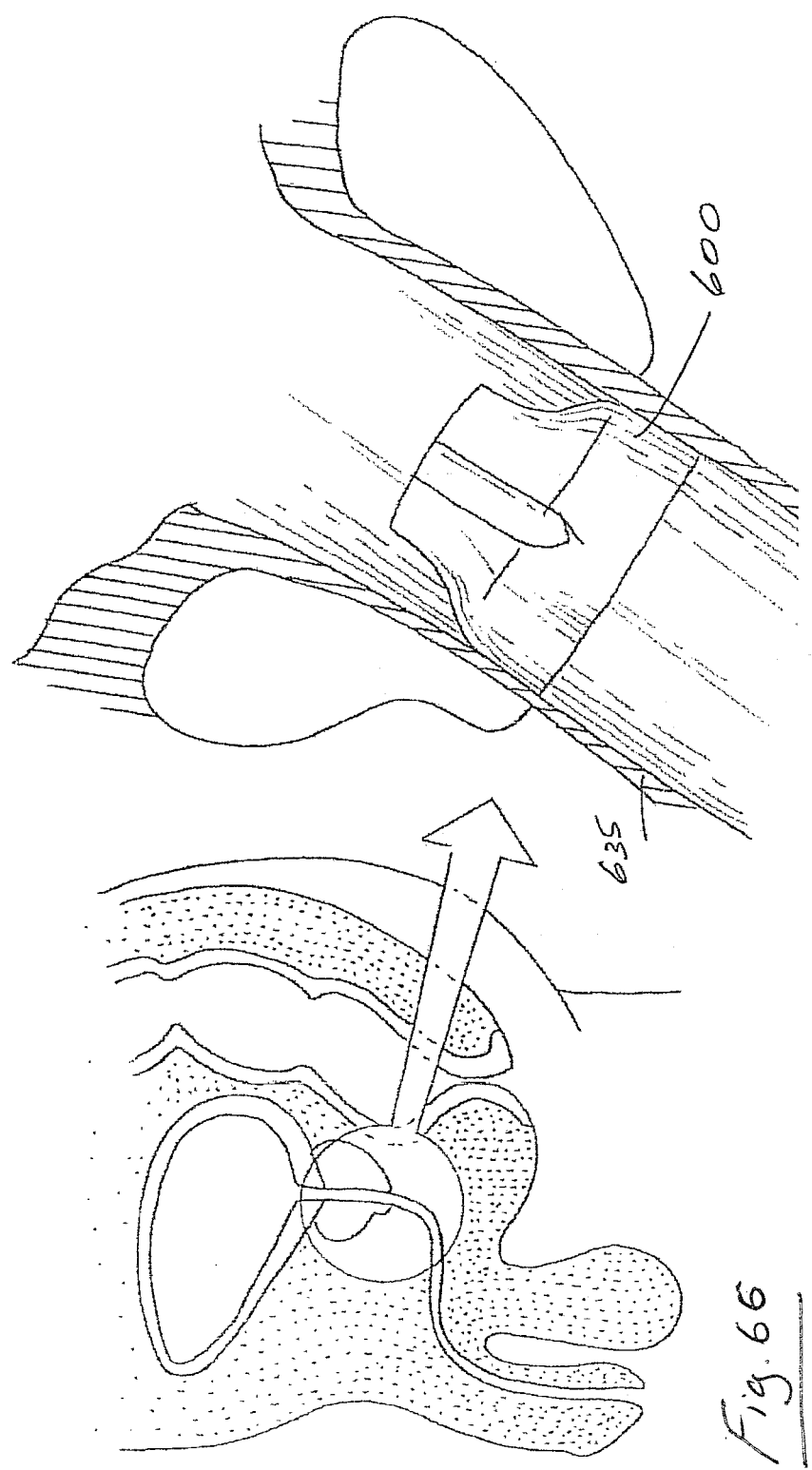
FIG. 66 is a cross sectional view of another internal urological valve device in use.
FIG. 67 is an enlarged view of a detail of FIG. 66.

FIGS. 66 and 67 illustrate a urology valve 600 in a self retaining structure 635 placed in the urethra. This could be held in placed with an adhesive or through anchoring or suturing technology.

Referring to FIGS. 68 to 70 there is illustrated another valve device 800 according to the invention. The device 800 comprises a hollow stem 801 and a head part 802 having slits 803 therein forming valve leaflets. When the slits 803 open in response to applied pressure, urine flows through the head part 802 and into a flow channel 804 extending through the stem 801. The stem 801 also has a bulbous part 805 to assist in locating and retaining the device in situ within a bladder neck 806.

Figure 71:
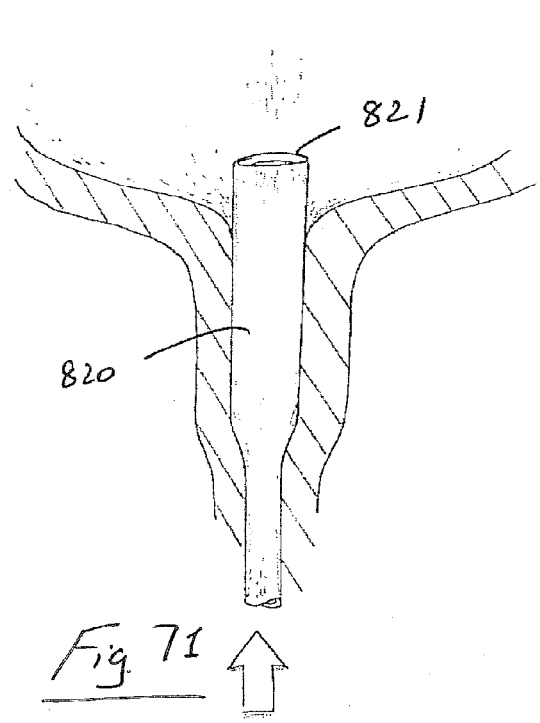
FIGS. 71 to 73 are diagrams illustrating the delivery and deployment of a valve device according to the invention.
Figure 72:
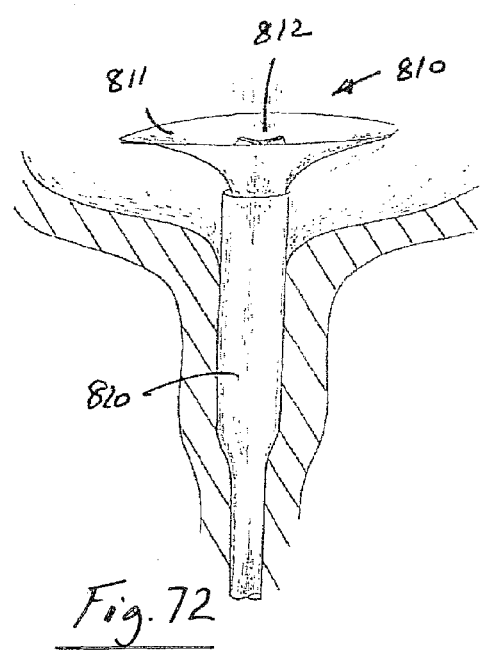
Figure 73:
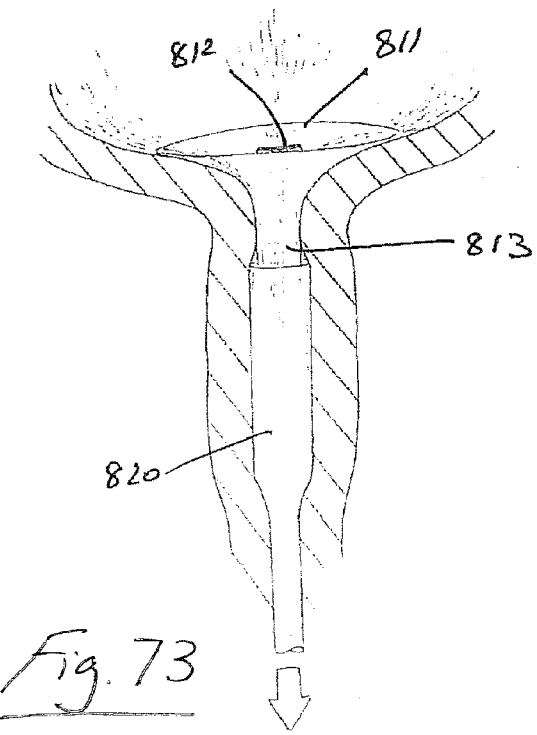

FIGS. 71 to 73 illustrate the delivery and deployment of a valve device 810 having a head part 811 with a valve 812 and a stem part 813. The delivery system comprises a catheter 820 which is advanced into the neck of the bladder. The valve device 810 is retained within the catheter 820 in a retracted configuration (FIG. 71). The device 810 is deployed from the distal end 821 of the catheter (FIG. 72). During deployment the valve device 810 expands to a deployed configuration and the catheter 820 is withdrawn to deploy the proximal end of the device (FIG. 73).

Figure 74:
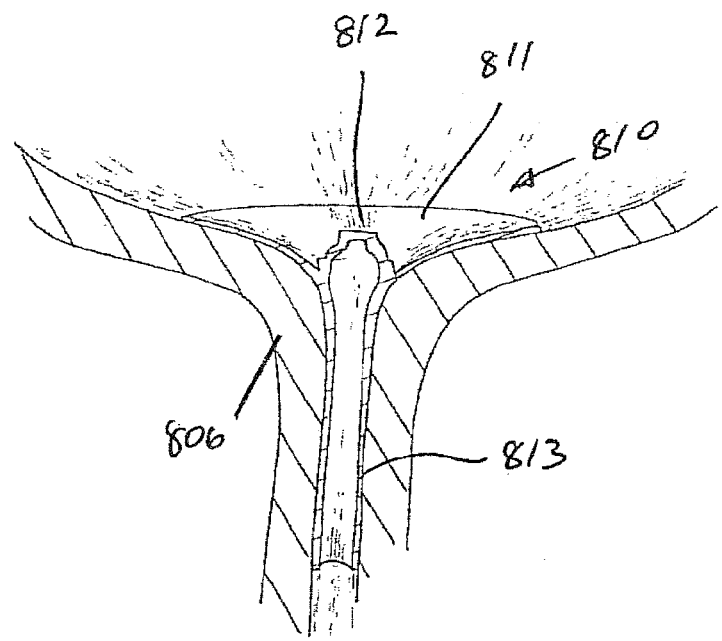
FIG. 74 is a cross sectional view of another valve device of the invention deployed in a bladder neck.
Figure 75:
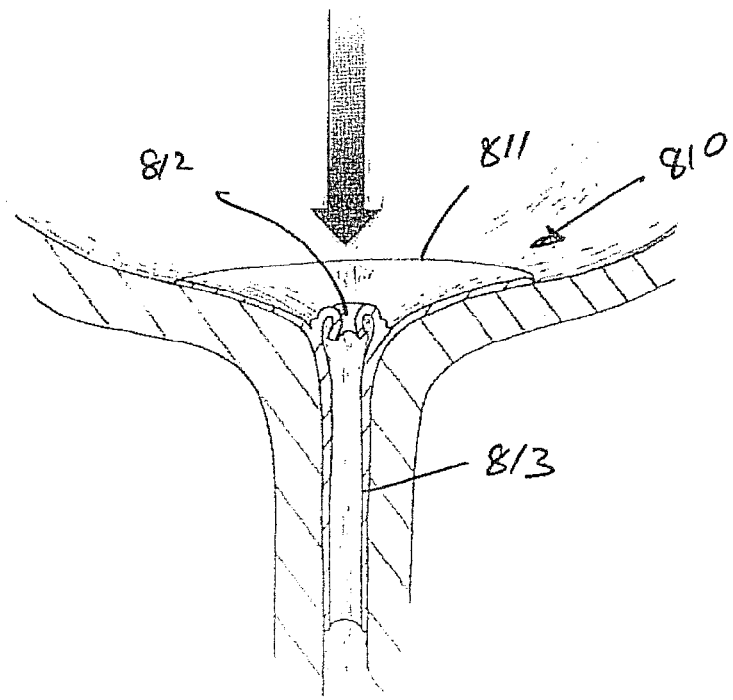
FIG. 75 is a cross sectional view illustrating the opening of a valve at the proximal end of the device of FIG. 74 opening in response to pressure.

FIGS. 74 and 75 illustrate the functioning of the valve device 810 deployed in the bladder neck. The valve 812 at the proximal end opens in response to applied pressure.

FIGS. 76 and 77 illustrate a valve device 830 which is similar to the device of FIGS. 71 to 75. In this case there is a tab 831 at the distal tip of the device to ensure that the device is firmly located in situ. The tab 831 typically anchors at the meatus to prevent proximal migration into the bladder.

Figure 80:
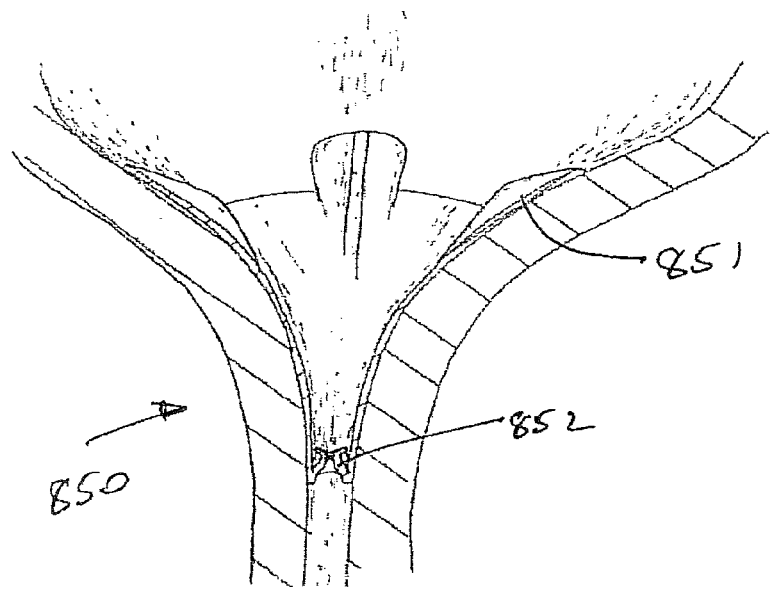
FIG. 80 is a cross sectional view of the device of FIGS. 78 and 79 anchored in a bladder neck.

Referring to FIGS. 78 to 80 there is illustrated another valve device 850 according to the invention which in this case has anchoring tabs 851 for anchoring the device in the bladder neck. In this case a valve part 852 is located in the urethra.

Figure 81:
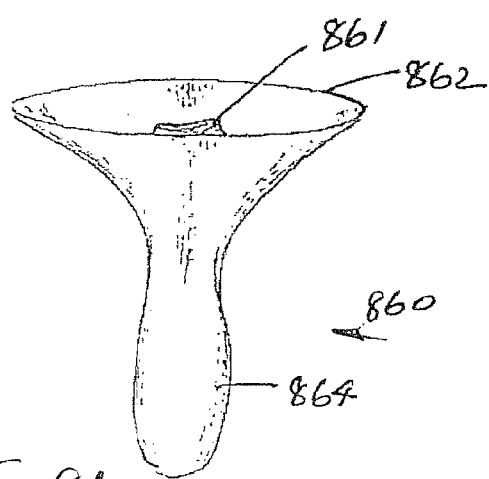
FIG. 81 is a perspective view of another valve device according to the invention.
Figure 82:
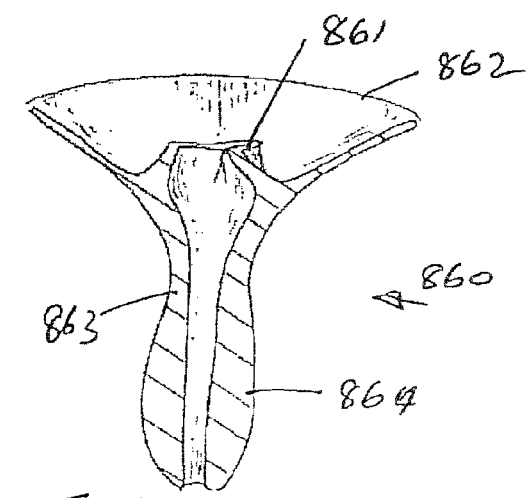
FIG. 82 is a cross sectional view of the device of FIG. 81.
Figure 83:
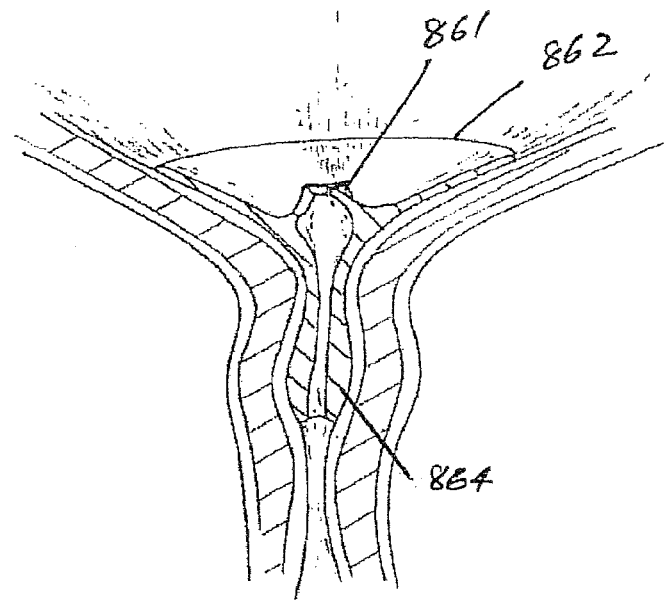
FIG. 83 is a cross sectional view of the device of FIGS. 81 and 82 in use.

Referring to FIGS. 81 to 83 there is illustrated another valve device 860 according to the invention. The device 860 comprises a valve part 861, a head part 862, and a stem part 863. The stem part 863 has a soft compressible foam structure 864 that anchors in the membranous urethra.

Figure 84:
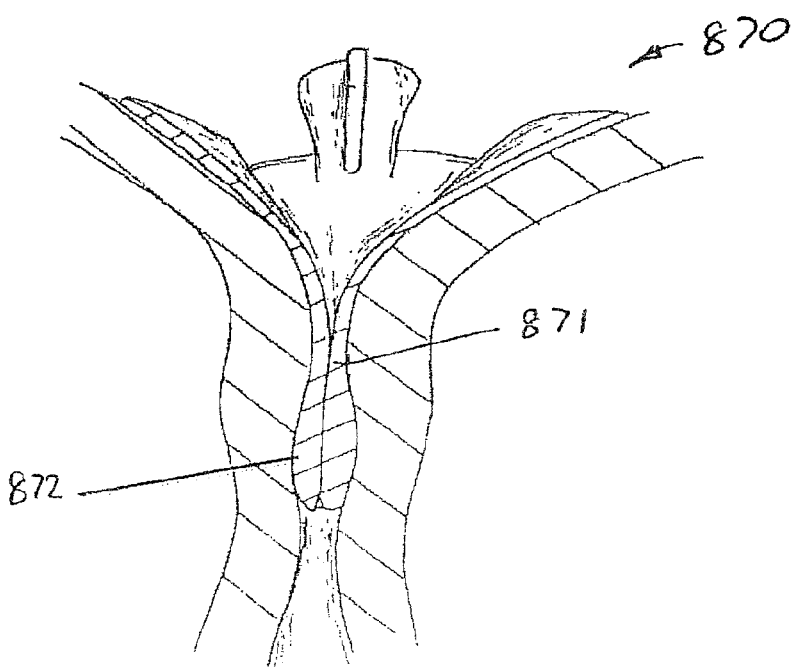
FIG. 84 is a cross sectional view of another valve device according to the invention, in use.

Referring to FIG. 84 there is illustrated another valve device 870 according to the invention. The valve device 870 has a stem port 871 with a deformable foam bulb 872. The bulb 872 acts as a valve and has a normally closed configuration. Application of a predefined pressure causes the valve to open.

Figure 86:
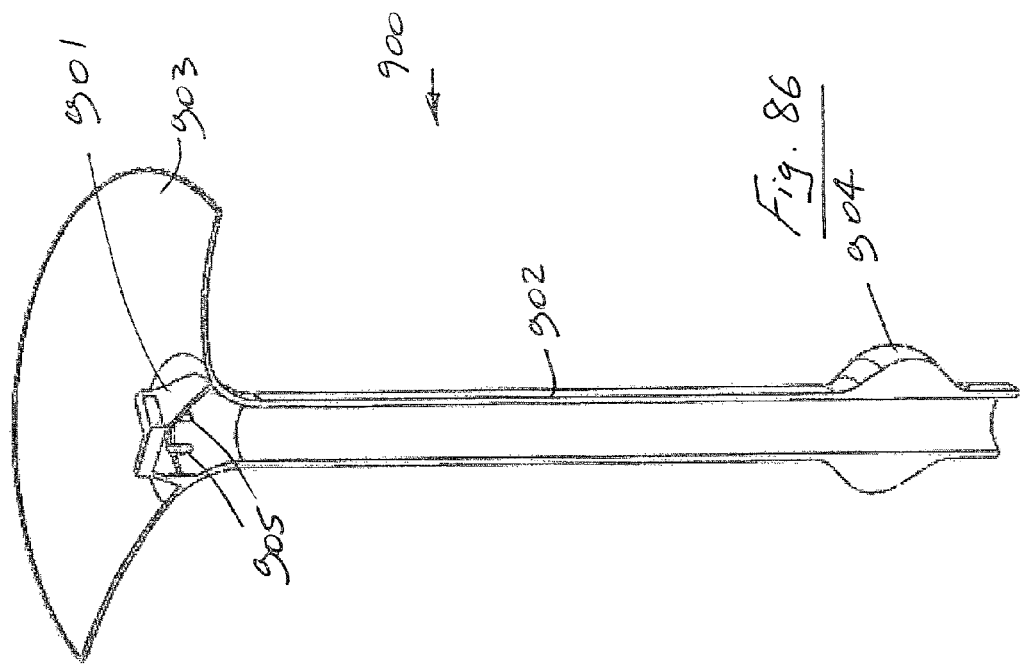
FIG. 86 is a cut-away view of the device of FIG. 85.
Figure 85:
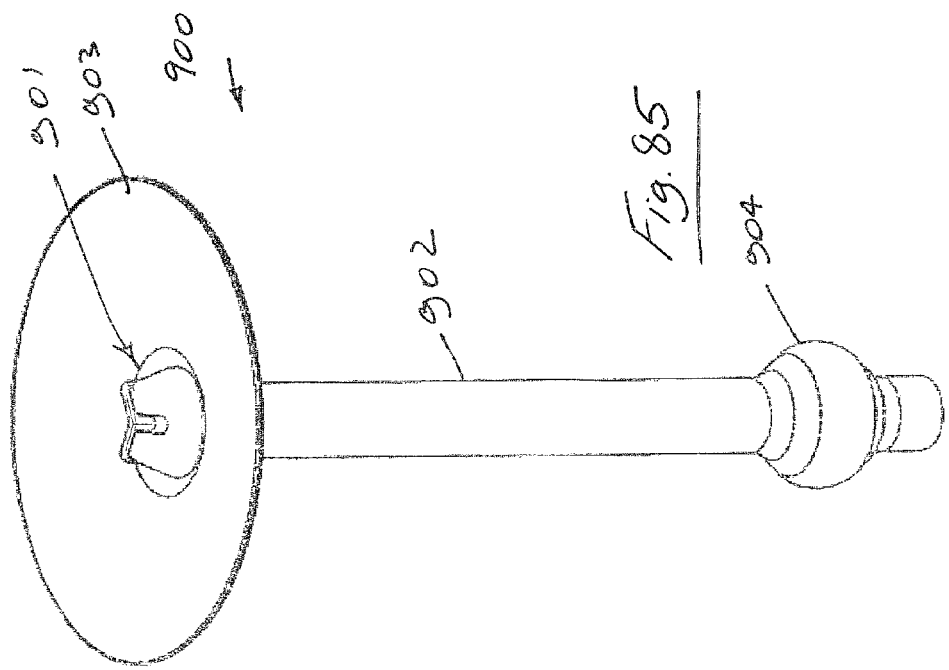
FIG. 85 is a perspective view of another urological device according to the invention.

Referring to FIGS. 85 to 86 there is illustrated another urological device 900 according to the invention. In this case the device is for use in a male. The device 900 comprises a valve 901 at one end of a tubular stem 902. The device has a bladder retainer comprising a flared region 903 which is typically of 40 mm diameter for a valve diameter of 9 mm. The device also has a second retainer in this case provided by a bulbous region 904 for maintaining the position of the device in the urethra.

The valve 901 is in this case of a polymeric viscoelastic foam material and is of the type described above with reference to FIGS. 1 to 20.

In this case the leaflets are at the top of the device and the valve has a stiffening means provided by vertical reinforcement features 905 which define a fulcrum or hinge region about which the valve leaflets are movable from a normally closed configuration as illustrated in FIGS. 85 to 88 to an open position. The valve has a region of co-aption between the valve leaflets and has a normally closed configuration in which the valve leaflets are engaged at the region of co-aption and an open configuration in which the leaflets are separated at the co-aption region for fluid flow through the valve. The valve is movable automatically from the closed to the open configuration in response to applied urological pressure. In this case the leaflets evert on movement between the closed and the open configuration in response to user patient applied urological pressure. The valve is adapted to open in response to a preset pressure applied over a preset time. For example, the valve may be adapted to open in response to a pressure of at least 750 mm $H_2O$ applied for at least 5 seconds. However, the valve remains closed in response to a strike pressure applied for a short time such as would be generated by a user coughing. The valve remains open as fluid flows therethrough without a requirement for a user to continue to apply urological pressure. The flow through the valve is sufficient to keep the valve open. The valve returns to the closed configuration when flow through the valve has substantially stopped. The valve in this case everts on movement from the closed to the open configuration and reverts on movement from the open to the closed configuration.

In this case the valve and the other elements of the device are all of a polymeric viscoelastic foam material. For example, for optimised manufacturing and cost the device may be integrally moulded.

The various urological devices of the invention may comprise a suitable anti-microbial agent such as an anti-microbial coating.

Figure 89:
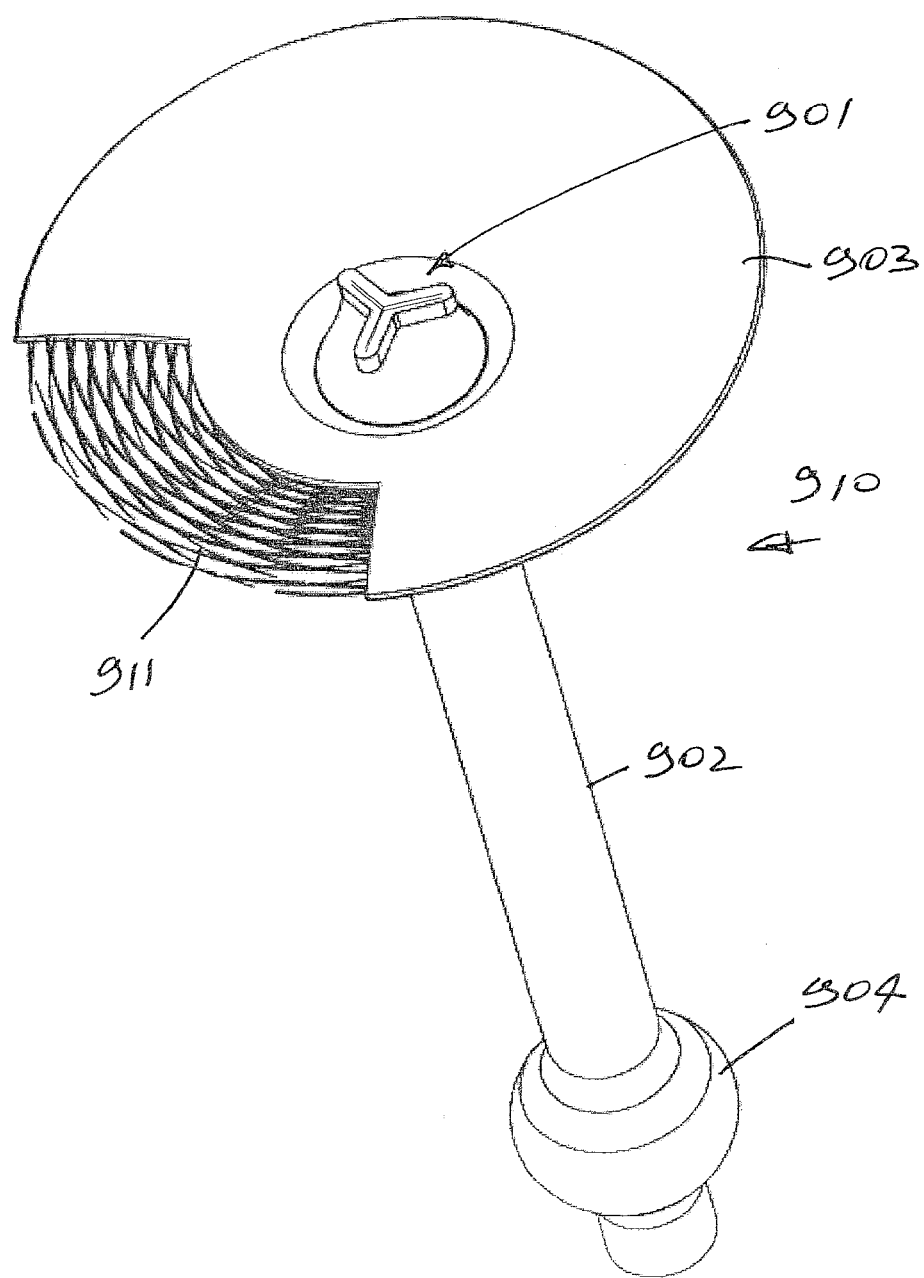
FIG. 89 is a perspective view of a further urological device according to the invention.

Referring to FIG. 89 there is illustrated another urological device 910 which is similar to the device of FIGS. 85 to 88 and like parts are assigned the same reference numerals. In this case the retaining flare 903 is reinforced, for example by a mesh 911 which may, for example be of a shape memory material such as Nitinol.

Referring to FIGS. 90 to 93 there is illustrated another urological device 920 according to the invention which is similar to the device of FIGS. 85 to 88 and like parts are assigned the same reference numerals. In this case the device is for female use and the retaining means comprises a metal tab 921 for prevention of proximal migration.

Test Results

Various tests were carried out using the urological devices of the invention. The following relates in particular to a female urological device as illustrated in FIG. 90 and described above. The device was manufactured from a polymeric foam material as described in Example 5 below. The valve was a 9 mm valve Referring to FIG. 94 the flow characteristics through a urological device of the invention is illustrated. It can be seen that flow through the valve is maintained even when the pressure is very low. This feature ensures that emptying of the bladder can be completed without maintaining constant urological or abdominal pressure.

Figure 95:
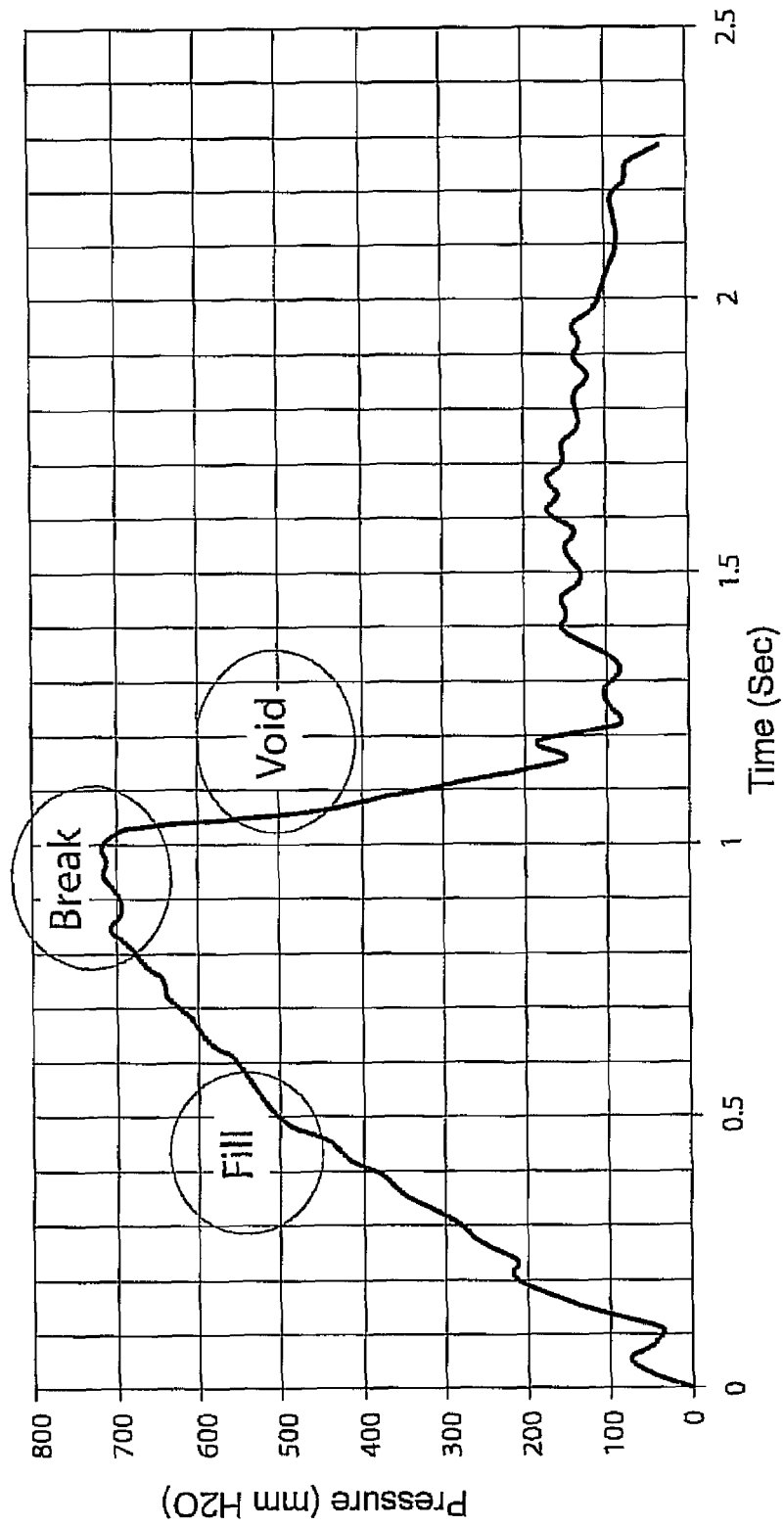
FIG. 95 is a graph of the pressure profile of a urological device of the invention during accelerated bladder filling simulation.

Referring to FIG. 95 the pressure profile of a urological device of the invention is illustrated during simulated bladder pressure ramp. It can be seen that until a certain pressure is exerted on the valve the valve does not open. Further the pressure continues to drop even after the initial depressurization of the valve due to opening. This in turn illustrates a similar point to FIG. 94 in that constant application of elevated pressure is not required to keep the valve open.

Figure 96:
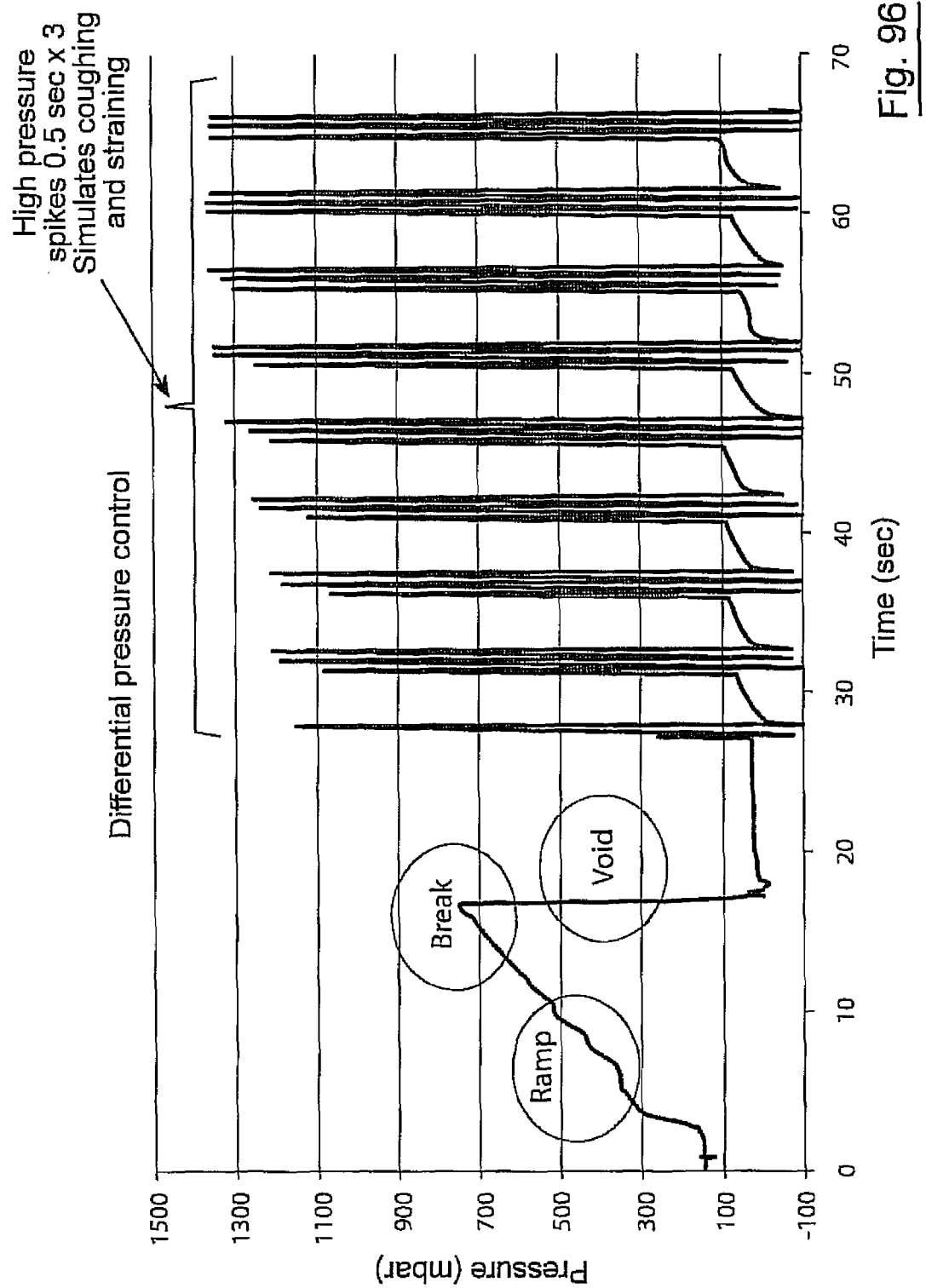
FIG. 96 is a graph of differential pressure control using a urological device of the invention.

Referring to FIG. 96 differential pressure control using a urological device of the invention is illustrated. In this illustration the first peak shows the normal opening of the valve due to application of elevated pressure. The magnitude of pressure required to trigger the valve in this case is indicative of a prolonged application or ramping of pressure or valsalva maneuver. The second set of peaks illustrates the application of high pressure spikes to the valve to simulate coughing. In the case of coughing the valve does not open.

The following section describes one group of biomaterials that are suitable for manufacturing devices and valves of the invention.

The material may also be as described in our application entitled "A biomaterial" Ref: VYSE12 filed on the same date as this application. The entire contents of the VYSE12 application are herein incorporated by reference in its entirety.

Use of polyethers as soft segments in polyurethane foams is know to result in soft elastic and viscoelastic materials due to the dynamic reinforcing effect of hydrogen bonding. Conversely, use of non-hydrogen bonding hydrophobic soft segments results in harder, less elastic material. Blending of such hydrophobic and hydrophilic homopolymer soft segments as shown in FIG. 85 via urethane/urea linkages is known in the art to achieve mechanical properties appropriate to specific applications.

Acid catalysed hydrolytic degradation occurs at urethane linkages within polyurethane materials. These urethane/urea linkages are therefore the 'weak-links' of the polyurethane material. It follows that the intrinsic hydrophilicity of the polyurethane material will affect the rate of hydrolysis through modulation of water uptake. Thus, such materials are incompatible with use in a gastric environment (i.e., a highly acidic aqueous environment).

Thus, in some embodiments, the present invention provides a multiblock copolymer that is biomimetic and hydrolytically stable in a gastric environment. Such multiblock copolymers are of formula I:

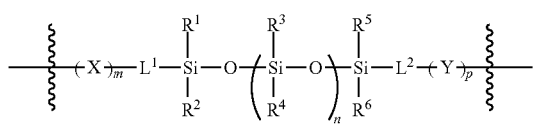

wherein:

each $\xi$ represents a point of attachment to a urethane or urea linkage;

each of X and Y is independently a polymer or co-polymer chain formed from one or more of a polyether, a polyester, a polycarbonate, or a fluoropolymer;

each of $R^1$, $R^2$, $R^3$, $R^4$, $R^5$ and $R^6$ is independently selected from one or more of R, OR, —$CO_2R$, a fluorinated hydrocarbon, a polyether, a polyester or a fluoropolymer;

each R is independently hydrogen, an optionally substituted $C_{1-20}$ aliphatic group, or an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulfur;

each of m n and p is independently 2 to 100; and each of $L^1$ and $L^2$ is independently a bivalent $C_{1-20}$ hydrocarbon chain wherein 1-4 methylene units of the hydrocarbon chain are optionally and independently replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, —C(O)O—, or a bivalent cycloalkylene, arylene, heterocyclene, or heteroarylene, provided that neither of $L^1$ nor $L^2$ comprises a urea or urethane moiety.

2. DEFINITIONS

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation.

As used herein, the term "bivalent $C_{1-8}$ [or $C_{1-6}$] saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}$—$CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2$ $OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°_2$; $SiR°_3$; —$(C_{1-4}$ straight or branched)alkylene)O—N$(R°)_2$; or —$(C_{1-4}$ straight or branched) alkylene)C(O)O—N$(R°_2$, wherein each $R°$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SR^•$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

3. DESCRIPTION OF EXEMPLARY EMBODIMENTS

A. Multiblock Copolymers

As described generally above, one embodiment of the present invention provides a triblock copolymer of formula I:

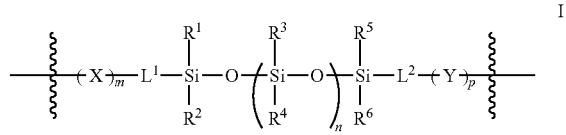

wherein the copolymers are chemically interspersed (bound) between urethane and/or urea linkages (i.e., at the bond designated with ⸹ ) and wherein each of X, Y, m, n, p, $L^1$, $L^2$, $R^1$, $R^2$, $R^3$, $R^4$, $R^5$, and $R^6$ is as defined and described herein.

As defined generally above, the each of X and Y groups of formula I is independently a polymer or co-polymer chain formed from one or more of a polyether, a polyester, a polycarbonate, and a fluoropolymer.

Examples of polymer or co-polymer chains represented by X and/or Y include: poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof, poly(dimethylsiloxane), poly(diethylsiloxane) and higher alkyl siloxanes, poly(methyl phenyl siloxane), poly(diphenyl siloxane), poly(methyl di-fluoroethyl siloxane), poly(methyl tri-fluoroethyl siloxane), poly(phenyl di-fluoroethyl siloxane), poly(phenyl tri-fluoroethyl siloxane) and copolymers thereof, poly(ethylene terephthalate) (PET), poly (ethylene terephthalate ionomer) (PETI), poly(ethylene naphthalate) (PEN), poly(methylene naphthalate) (PTN), poly(butylene teraphalate) (PBT), poly(butylene naphthalate) (PBN), polycarbonate.

In certain embodiments, the present invention provides a pre-formed soft segment for a polyurethane/urea foam.

In some embodiments X is a polyether and Y is a polyether. More specifically in one case X and Y are both poly(propylene oxide).

In certain embodiments, m and p are each independently between 2 and 50 and n is between 2 and 20. In some embodiments, m and p are each independently between 2 and 30 and n is between 2 and 20.

As defined generally above, each of $R^1$, $R^2$, $R^3$, $R^4$, $R^5$ and $R^6$ is independently selected from one or more of R, OR, —CO$_2$R, a fluorinated hydrocarbon, a polyether, a polyester or a fluoropolymer. In some embodiments, one or more of $R^1$, $R^2$, $R^3$, $R^4$, $R^5$ and $R^6$ is —CO$_2$R. In some embodiments, one or more of $R^1$, $R^2$, $R^3$, $R^4$, $R^5$ and $R^6$ is —CO$_2$R wherein each R is independently an optionally substituted $C_{1-6}$ aliphatic group. In certain embodiments, one or more of $R^1$, $R^2$, $R^3$, $R^4$, $R^5$ and $R^6$ is —CO$_2$R wherein each R is independently an unsubstituted $C_{1-6}$ alkyl group. Exemplary such groups include methanoic or ethanoic acid as well as methacrylic acid and other acrylic acids.

In certain embodiments, one or more of $R^1$, $R^2$, $R^3$, $R^4$, $R^5$ and $R^6$ is independently R. In some embodiments, one or more of $R^1$, $R^2$, $R^3$, $R^4$, $R^5$ and $R^6$ is an optionally substituted $C_{1-6}$ aliphatic group. In certain embodiments, one or more of $R^1$, $R^2$, $R^3$, $R^4$, $R^5$ and $R^6$ is an optionally substituted $C_{1-6}$ alkyl. In other embodiments, one or more of $R^1$, $R^2$, $R^3$, $R^4$, $R^5$ and $R^6$ is an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulphur. Exemplary such $R^1$, $R^2$, $R^3$, $R^4$, $R^5$ and $R^6$ groups include methyl, ethyl, propyl, isopropyl, cyclopropyl, butyl, isobutyl, cyclobutyl, phenyl, pyridyl, morpholinyl, pyrrolidinyl, imidazolyl, and cyclohexyl.

In certain embodiments, one or more of $R^1$, $R^2$, $R^3$, $R^4$, $R^5$ and $R^6$ is independently —OR. In some embodiments, one or more of $R^1$, $R^2$, $R^3$, $R^4$, $R^5$ and $R^6$ is —OR wherein R is an optionally substituted $C_{1-6}$ aliphatic group. In certain embodiments, one or more of $R^1$, $R^2$, $R^3$, $R^4$, $R^5$ and $R^6$ is —OR wherein R is $C_{1-6}$ alkyl. In other embodiments, one or more of $R^1$, $R^2$, $R^3$, $R^4$, $R^5$ and $R^6$ is —OR wherein R is an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulphur. Exemplary such $R^1$, $R^2$, $R^3$, $R^4$, $R^5$ and $R^6$ groups include —Omethyl, —Oethyl, —Opropyl, —Oisopropyl, —Ocyclopropyl, —Obutyl, —Oisobutyl, —Ocyclobutyl, —Ophenyl, —Opyridyl, —Omorpholinyl, —Opyrrolidinyl, —Oimidazolyl, and —Ocyclohexyl.

In certain embodiments, one or more of $R^1$, $R^2$, $R^3$, $R^4$, $R^5$ and $R^6$ is independently R wherein each R is a $C_{1-6}$ aliphatic group substituted with one or more halogens. In some embodiments, each R is $C_{1-6}$ aliphatic substituted with one, two, or three halogens. In other embodiments, each R is a perfluorinated $C_{1-6}$ aliphatic group. Examples of fluorinated hydrocarbons represented by $R^1$, $R^2$, $R^3$, $R^4$, $R^5$ and $R^6$ include mono-, di-, tri, or perfluorinated methyl, ethyl, propyl, butyl, or phenyl. In some embodiments, each of $R^1$, $R^2$, $R^3$, $R^4$, $R^5$ and $R^6$ is trifluoromethyl, trifluoroethyl, or trifluoropropyl.

In certain embodiments, one or more of $R^1$, $R^2$, $R^3$, $R^4$, $R^5$ and $R^6$ is independently a polyether. Examples of polyethers represented by $R^1$, $R^2$, $R^3$, $R^4$, $R^5$ and $R^6$ include poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof.

In certain embodiments, one or more of $R^1$, $R^2$, $R^3$, $R^4$, $R^5$ and $R^6$ is independently a polyester. Examples of polyesters represented by $R^1$, $R^2$, $R^3$, $R^4$, $R^5$ and $R^6$ include poly(ethylene terephthalate) (PET), poly(ethylene terephthalate ionomer) (PETI), poly(ethylene naphthalate) (PEN), poly(methylene naphthalate) (PTN), poly(butylene teraphalate) (PBT), poly(butylene naphthalate) (PBN), polycarbonate.

In certain embodiments, one or more of $R^1$, $R^2$, $R^3$, $R^4$, $R^5$ and $R^6$ is independently a fluoropolymer. Examples of fluoropolymers represented by $R^1$, $R^2$, $R^3$, $R^4$, $R^5$ and $R^6$ include poly(tetrafluoroethylene), poly(methyl di-fluoroethyl siloxane), poly(methyl tri-fluoroethyl siloxane), poly(phenyl di-fluoroethyl siloxane).

In some embodiments, $R^1$, $R^2$, $R^3$, $R^4$, $R^5$ and $R^6$ is independently hydrogen, hydroxyl, carboxylic acids such as methanoic or ethanoic acid as well as methacrylic acid and other acrylic acids. Alkyl or aryl hydrocarbons such as methyl, ethyl, propyl, butyl, phenyl and ethers thereof. Fluorinated hydrocarbons such as mono-, di-, tri, or perfluorinated methyl, ethyl, propyl, butyl, phenyl. Polyether such as Poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof. Polyesters such as Poly(ethylene terephthalate) (PET), poly(ethylene terephthalate ionomer) (PETI), poly(ethylene naphthalate) (PEN), poly(methylene naphthalate) (PTN), Poly(Butylene Teraphalate) (PBT), poly(butylene naphthalate) (PBN), polycarbonate and .fluoropolymer such as Poly(tetrafluoroethylene), poly(methyl di-fluoroethyl siloxane), poly(methyl tri-fluoroethyl siloxane), poly(phenyl di-fluoroethyl siloxane).

In some embodiments, m and p are between 2 and 50 and n is between 2 and 20. In certain embodiments, m and o are between 2 and 30 and n is between 2 and 20.

As defined generally above, each of $L^1$ and $L^2$ is independently a bivalent $C_{1-20}$ hydrocarbon chain wherein 1-4 methylene units of the hydrocarbon chain are optionally and independently replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, —C(O)O—, or a bivalent cycloalkylene, arylene, heterocyclene, or heteroarylene, provided that neither of $L^1$ nor $L^2$ comprises a urea or urethane moiety. In some embodiments, each of $L^1$ and $L^2$ is independently a bivalent $C_{1-20}$ alkylene chain. In certain embodiments, each of $L^1$ and $L^2$ is independently a bivalent $C_{1-10}$ alkylene chain. In certain embodiments, each of $L^1$ and $L^2$ is independently a bivalent $C_{1-6}$ alkylene chain. In certain embodiments, each of $L^1$ and $L^2$ is independently a bivalent $C_{1-4}$ alkylene chain. Exemplary such $L^1$ and $L^2$ groups include methylene, ethylene, propylene, butylene or higher bivalent alkanes.

In some embodiments, each of $L^1$ and $L^2$ is independently a bivalent $C_{1-20}$ alkylene chain wherein one methylene unit of the chain is replaced by —O—. In some embodiments, each of $L^1$ and $L^2$ is independently a bivalent $C_{1-10}$ alkylene chain wherein one methylene unit of the chain is replaced by —O—. In some embodiments, each of $L^1$ and $L^2$ is independently a bivalent $C_{1-6}$ alkylene chain wherein one methylene unit of the chain is replaced by —O—. In some embodiments, each of $L^1$ and $L^2$ is independently a bivalent $C_{1-4}$ alkylene chain wherein one methylene unit of the chain is replaced by —O—. Exemplary such $L^1$ and $L^2$ groups include —OCH$_2$—, —OCH$_2$CH$_2$—, —OCH$_2$CH$_2$CH$_2$—, —OCH$_2$CH$_2$CH$_2$CH$_2$—, or higher bivalent alkylene ethers.

In some embodiments, each of $L^1$ and $L^2$ is independently a bivalent $C_{1-20}$ alkylene chain wherein at least one methylene unit of the chain is replaced by —O— and at least one methylene unit of the chain is replaced by a bivalent arylene. In some embodiments, each of $L^1$ and $L^2$ is independently a bivalent $C_{1-10}$ alkylene chain wherein at least one methylene unit of the chain is replaced by —O— and at least one methylene unit of the chain is replaced by a bivalent arylene. In some embodiments, each of $L^1$ and $L^2$ is independently a bivalent $C_{1-6}$ alkylene chain wherein at least one methylene unit of the chain is replaced by —O— and at least one methylene unit of the chain is replaced by a bivalent arylene. In some embodiments, each of $L^1$ and $L^2$ is independently a bivalent $C_{1-4}$ alkylene chain wherein at least one methylene unit of the chain is replaced by —O— and at least one methylene unit of the chain is replaced by a bivalent arylene. Exemplary such $L^1$ and $L^2$ groups include —OCH$_2$-phenylene-, —OCH$_2$CH$_2$-phenylene-, —OCH$_2$CH$_2$-phenylene-CH$_2$—, —OCH$_2$CH$_2$CH$_2$CH$_2$-phenylene-, and the like.

One of ordinary skill in the art would understand that a polyurethane results from the reaction of a diisocyanate and a hydroxyl group. Similarly, a polyurea results from the reaction of a diisocyanate and an amine. Each of these reactions is depicted below.

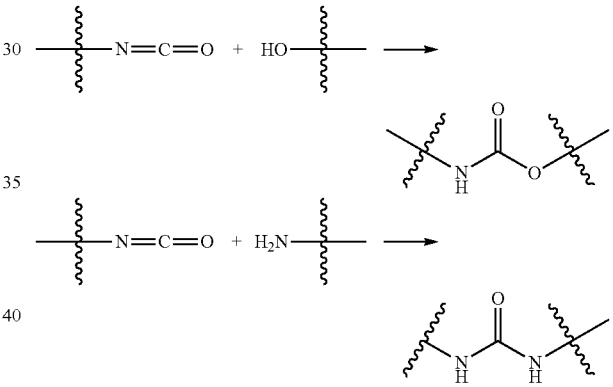

Thus, it is readily apparent that provided compounds of formula I can be functionalized with end groups suitable for forming urethane and/or urea linkages. In certain embodiments, the present invention provides a compound of formula II:

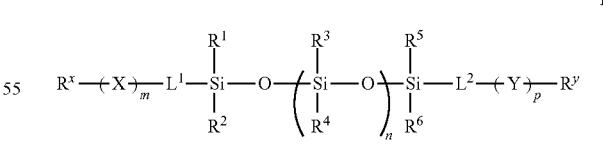

wherein:
each of $R^x$ and $R^y$ is independently —OH, —NH$_2$, a protected hydroxyl or a protected amine;
each of X and Y is independently a polymer or co-polymer chain formed from one or more of a polyether, a polyester, a polycarbonate, and a fluoropolymer;
each of $R^1$, $R^2$, $R^3$, $R^4$, $R^5$ and $R^6$ is independently selected from one or more of R, OR, —CO$_2$R, a fluorinated hydrocarbon, a polyether, a polyester or a fluoropolymer;

each R is independently hydrogen, an optionally substituted $C_{1-20}$ aliphatic group, or an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulfur;

each of m n and p is independently 2 to 100; and each of $L^1$ and $L^2$ is independently a bivalent $C_{1-20}$ hydrocarbon chain wherein 1-4 methylene units of the hydrocarbon chain are optionally and independently replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, —C(O)O—, or a bivalent cycloalkylene, arylene, heterocyclene, or heteroarylene, provided that neither of $L^1$ nor $L^2$ comprises a urea or urethane moiety.

In some embodiments, each of X, Y, m, n, p, $L^1$, $L^2$, $R^1$, $R^2$, $R^3$, $R^4$, $R^5$, and $R^6$ is as defined and described herein.

As defined generally above, each of $R^x$ and $R^y$ is independently —OH, —NH$_2$, a protected hydroxyl or a protected amine. In some embodiments, both of $R^x$ and $R^y$ are —OH. In other embodiments, both of $R^x$ and $R^y$ are —NH$_2$. In some embodiments one of $R^x$ and $R^y$ is —OH and the other is —NH$_2$.

In some embodiments, each of $R^x$ and $R^y$ is independently a protected hydroxyl or a protected amine Such protected hydroxyl and protected amine groups are well known to one of skill in the art and include those described in detail in *Protecting Groups in Organic Synthesis*, T. W. Greene and P. G. M. Wuts, 3rd edition, John Wiley & Sons, 1999, the entirety of which is incorporated herein by reference. Exemplary protected amines include methyl carbamate, ethyl carbamante, 9-fluorenylmethyl carbamate (Fmoc), 9-(2-sulfo) fluorenylmethyl carbamate, 9-(2,7-dibromo) fluoroenylmethyl carbamate, 2,7-di-t-butyl-[9-(10,10-dioxo-10,10,10,10-tetrahydrothioxanthyl)]methyl carbamate (DB D-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(4p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Exemplary hydroxyl protecting groups include methyl, methoxyl, methyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-trimethylsilyl)ethyl carbonate (TMSEC), 2-phenylsulfonyl) ethyl carbonate (Psec), 2-triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl) benzoate, 2,6-dichloro-4-methylphenoxyacetate, 2,6-dichloro-4-(1, 1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

One of ordinary skill in the art will appreciate that the choice of hydroxyl and amine protecting groups can be such that these groups are removed at the same time (e.g., when both protecting groups are acid labile or base labile). Alternatively, such groups can be removed in a step-wise fashion (e.g., when one protecting group is removed first by one set of removal conditions and the other protecting group is removed second by a different set of removal conditions). Such methods are readily understood by one of ordinary skill in the art.

In certain embodiments, the present invention provides a compound of any of formulae II-a, II-b, II-c, and II-d:

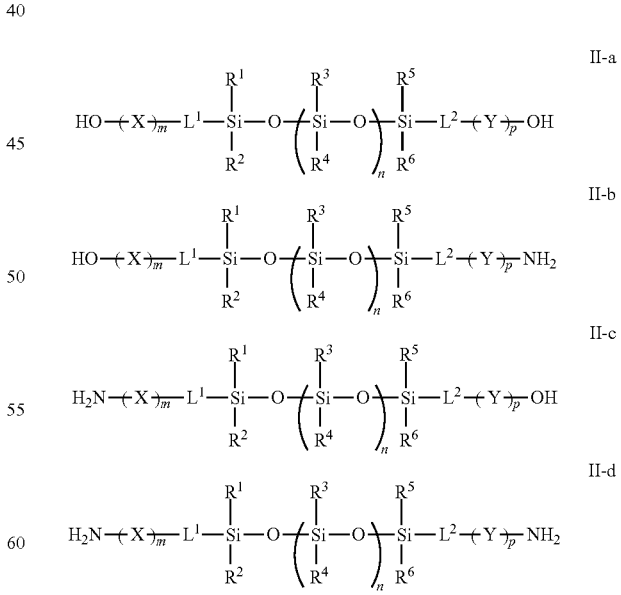

wherein each of X, Y, m, n, p, $L^1$, $L^2$, $R^1$, $R^2$, $R^3$, $R^4$, $R^5$, and $R^6$ is as defined and described herein.

Exemplary triblock copolymers of the present invention are set forth below:

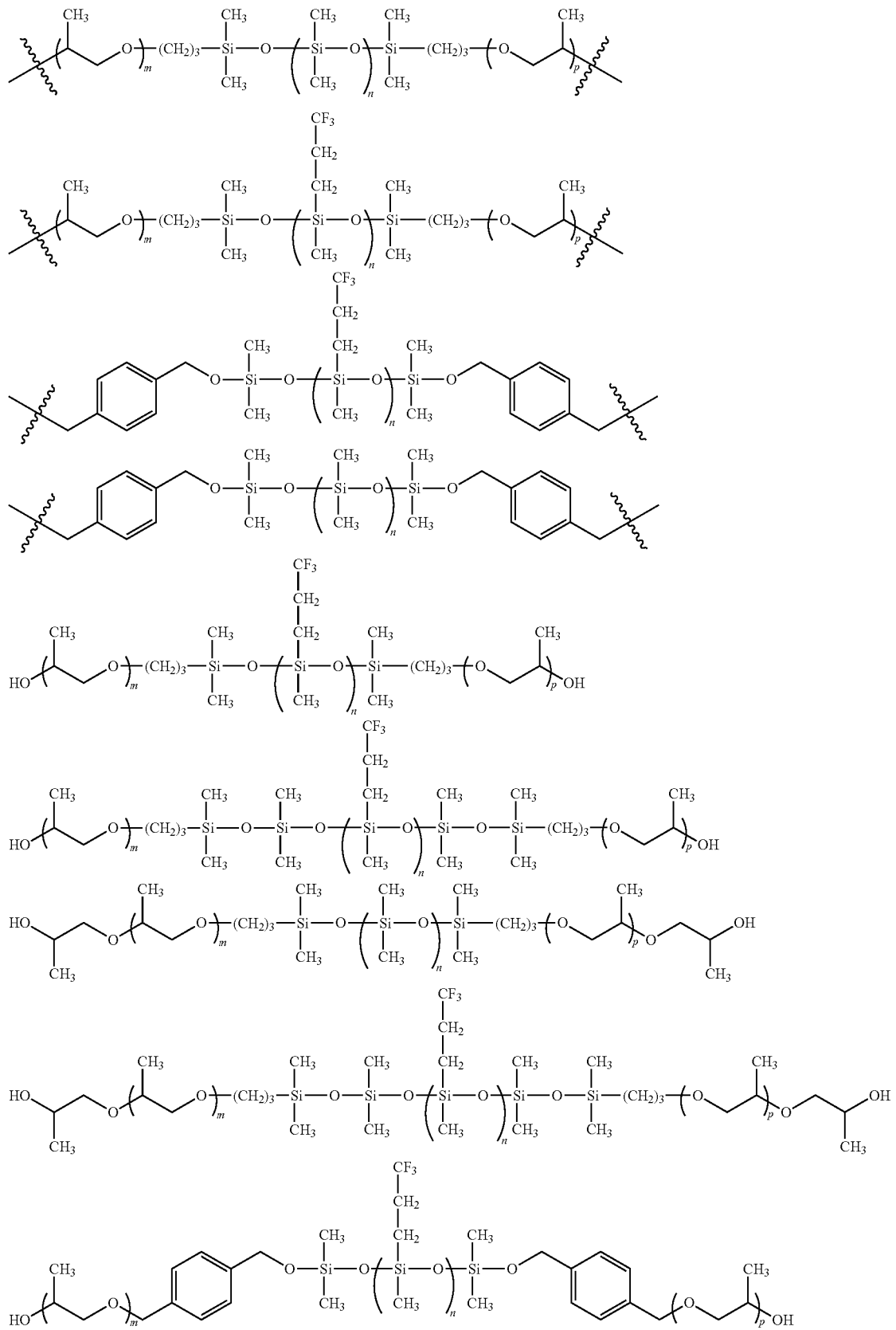
wherein each of m, n, and p is as defined and described herein.

In some embodiments, the present invention provides a polymer foam, comprising:
(a) one or more triblock copolymers of formula I:

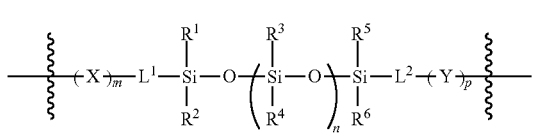

wherein each of X, Y, m, n, p, $L^1$, $L^2$, $R^1$, $R^2$, $R^3$, $R^4$, $R^5$, and $R^6$ is as defined and described herein; and
(b) wherein the copolymers are chemically interspersed (bound) between urethane and/or urea linkages (i.e., at the bond designated with §

The invention further provides a pre-formed soft segment of the formula I as defined above. In some embodiments, the present invention provides a polyurethane/urea foam comprising a soft segment triblock copolymer of formula I.

In some embodiments, the present invention provides a viscoelastic biostable water blown foam, comprising:
(a) one or more triblock copolymers of formula I:

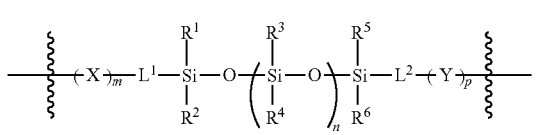

wherein each of X, Y, m, n, p, $L^1$, $L^2$, $R^1$, $R^2$, $R^3$, $R^4$, $R^5$, and $R^6$ is as defined and described herein; and
(b) wherein the copolymers are chemically interspersed (bound) between urethane and/or urea linkages (i.e., at the bond designated with §

It has been surprisingly found that polyurethanes and/or polyureas comprising a triblock copolymer of the present invention are stable to gastric fluid. Such polyurethanes and polyureas prepared using triblock copolymers of the present invention are viscoelastic and stable to gastric fluid. In some embodiments, a provided viscoelastic material is a foam.

In certain embodiments, a provided biostable foam is stable to gastric fluid. In some embodiments, a provided biostable foam is stable to gastric fluid for at least one year. In some embodiments, a provided biostable foam is stable to gastric fluid for at least 3 months, for at least 4 months, for at least 5 months, for at least 6 months, for at least 7 months, for at least 8 months, for at least 9 months, for at least 10 months, for at least 11 months, or for at least one year. Methods for determining stability of a provided biostable foam are known in the art utilizing simulated gastric fluid and include those described in detail in the Exemplification, infra.

In some embodiments, a provided viscoelastic foam, comprising a triblock copolymer of the present invention, is characterized in that the foam takes up less than about 30% by weight of water at equilibrium. In certain embodiments, a provided viscoelastic foam takes up less than about 5%, less than about 10%, less than about 15%, less than about 20%, less than about 25%, or less than about 30% by weight of water at equilibrium. One of ordinary skill in the art will appreciate that such chemical stability (i.e., in gastric fluid and therefore at very low pH) and hyrophobicity (i.e., water uptake of less than about 30% by weight) are characterisitics that differ dramatically from known siloxane polymers that are utilized in, e.g., the manufacture of contact lenses. For example, siloxane polymer that are utilized in, e.g., the manufacture of contact lenses require a water uptake of 50-120%.

As described above, the present invention provides a viscoelastic foam comprising a triblock copolymer of the present invention. It was suprisingly found that a provided foam has a high elongation capacity and the ability to recover very slowly following elongation. Indeed, it was found that a provided viscoelastic foam has an elongation capacity of about 200-1200%. In some embodiments, a provided viscoelastic foam has an elongation capacity of about 500%.

In some embodiments, a provided viscoelastic foam has a tensile strength of about 0.1 to about 1.0 MPa. In certain embodiments, a provided viscoelastic foam has a tensile strength of about 0.25 to about 0.5 MPa.

In some embodiments, a provided viscoelastic foam has a Young's Modulus of about 0.1 to about 0.6 MPa. In certain embodiments, a provided viscoelastic foam has a Young's Modulus of about 0.1 to about 0.5 MPa.

One of ordinary skill in the art will appreciate that, depending upon the physical characteristics required for a particular use of a provided foam, a foam of varying densities can be prepared. For example, a valve having a thinner wall would require a foam having a higher density than a similar valve having a thicker wall in order to result in each valve having a similar physical characteristic (e.g., tensile strength, and the like). Thus, in certain embodiments, a provided viscoelastic foam has a density of 0.1 to 1.5 g/cm³. In certain embodiments, a provided viscoelastic foam has a density of 0.3 to 1.2 g/cm³. In certain embodiments, a provided viscoelastic foam has a density of 0.8 to 0.9 g/cm³. In some embodiments, a provided viscoelastic foam has a density of 0.5 to 0.6 g/cm³.

Figure 99:
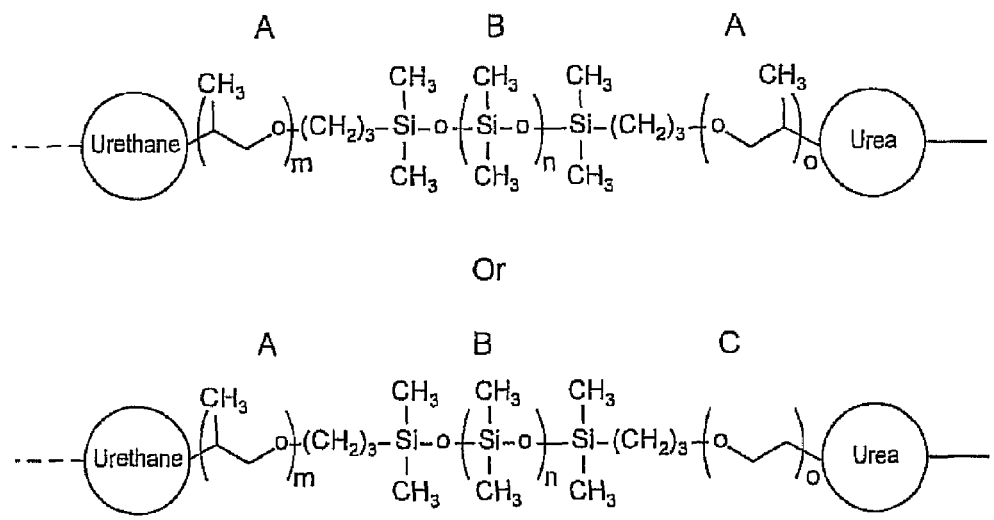
FIG. 99 is an illustration of a siloxane and polypropylene oxide based triblock copolymer in different forms.

In certain embodiments, the present invention provides polyether-siloxane and polyether-fluorosiloxane polyurethane materials with a greatly reduced number of weak-links as illustrated by FIG. 98 and FIG. 99. This was achieved by preforming the soft segment prior to the polyurethane reaction. In the examples below a triblock copolymer based on polydimethyl siloxane and polypropylene oxide was used but it will be appreciated that other triblock copolymers such as those formed from polysiloxanes and poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof, poly(dimethylsiloxane), poly(diethylsiloxane) and higher alkyl siloxanes, poly(methyl phenyl siloxane), poly(diphenyl siloxane), poly(methyl di-fluoroethyl siloxane), poly(methyl tri-fluoroethyl siloxane), poly(phenyl di-fluoroethyl siloxane), poly(phenyl tri-fluoroethyl siloxane) and copolymers thereof, poly(ethylene terephthalate) (PET), poly(ethylene terephthalate ionomer) (PETI), poly (ethylene naphthalate) (PEN), poly(methylene naphthalate) (PTN), poly(butylene teraphalate) (PBT), poly(butylene naphthalate) (PBN) and polycarbonate could be used.

Referring to FIG. 98, copolymers of the form ABA, ABC and BAB were produced from homopolymers of polysiloxane and polypropylene oxide which were covalently linked using bonds less labile than urethane/urea. The molecular weight and chemical characteristics of such homopolymers were tailored to achieve a pre-soft-segment with the appropriate balance of hydrophilicity/hydrophobicity. Without wishing to be bound by any particular theory, it is believe that by using a non-urethane linked tri-block copolymer instead of the constituent homopolymers as soft segments that the mechanical characteristics and hydrolytic stability of the resulting material is substantially improved.

In some embodiments, the present invention provides a foam comprising a copolymer of the present invention. Such foams offer specific advantages over solid elastomers, especially for gastrointestinal device applications. These advantages include enhanced biostability in the gastric environment, compressibility, viscoelasticity and high 'surface area to volume ratio'. The foam formulations of the invention can mimic mechanical characteristics of the native gastrointestinal tissue.

A biostable water blown foam was prepared from heterogenous reagents.

The prior art describes polyurethane foams that are prepared by the sequential reaction of polymer chains to one another resulting in a high molecular weight solid material. In all cases the polymeric precursors described in the art are linked together by urethane/urea linkages as illustrated in FIG. 97. However, each urethane/urea linkage is a possible site for degradation.

In the invention we have prepared a biostable polyurethane/urea foam with much fewer 'weak links' by using co-polymer precursors as shown in FIG. 98.

Polyurethane reactions have historically been carried out in a single phase due to ease of processing. However, we have made novel materials by combining physically heterogenous reaction pre-cursors together to form a stable two-phase dispersion ('water-in-oil') which was then reacted to form a foam.

EXEMPLIFICATION

In two specific examples X and Y are both polyethers namely poly(propylene oxide) (PPO). These were formulated into copolymers with poly(dimethylsiloxane) (PDMS) and poly(trifluoropropyl methylsiloxane) respectively in varying ratios as described by the following formulae:

Diethanolamine (DEOA) is used as a branching agent although it is sometimes known as a crosslinking agent. The molecular weight of DEOA is 105.14 g/mol. The effect of the DEOA is to influence softness and elasticity of the end polymer.

Gelling Catalyst—Bismuth Neodecanoate (BICAT)

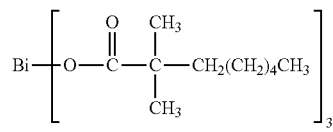

Bismuth neodecanoate is supplied as BiCat 8108M from Shepherd. It has a molecular weight of 722.75 g/mol. This catalyst is used to facilitate the complete reaction between isocyanate and hydroyl or amine functional groups.

Blowing Catalyst—DABCO 33-lv

DABCO is a common blowing catalyst for reaction between NCO and $H_2O$. It has a molecular weight of 112.17 g/mol. This catalyst has the effect, in combination with $H_2O$, of manipulating the foam rise characteristics.

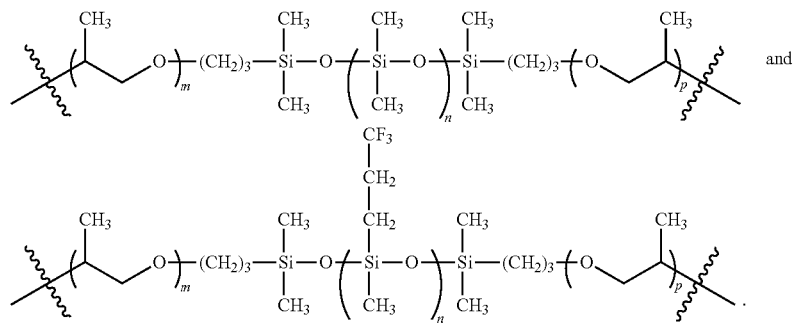

The formulations contained a number of other components including:

Branching Agent—DEOA

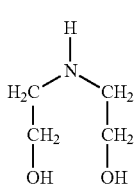

Example 1

Synthesis of Aliphatic Linked Fluorosiloxane Based Triblock Copolymer Pre-Soft-Segment This is a 2 step process. In the first step silanol terminated poly(trifluoropropyl methyl siloxane) is converted into its dihydride derivative. In the next step, this dihydride derivative is reacted with the allyl terminated poly(propylene glycol).

The synthetic procedure is as follows:
Step 1

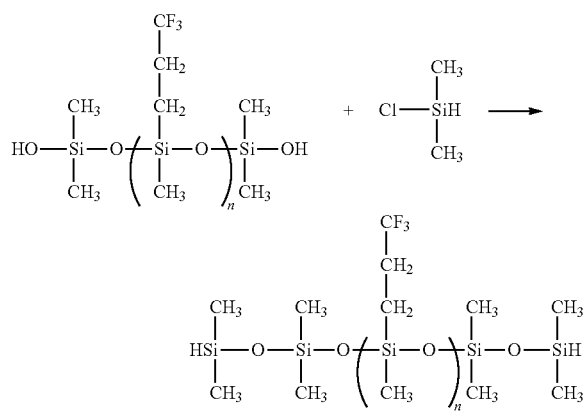

To a 4 neck separable flask fitted with mechanical stirrer, was added 40 g of Silanol terminated poly(trifluoropropyl methylsiloxane) (FMS-9922 from Gelest Inc.) and this was mixed with 50 ml of toluene and fitted with a continuous flush of Nitrogen. To the reaction mixture 7.57 g of dimethyl chlorosilane (DMCS, from Sigma Aldrich) was added slowly over about 20 minutes keeping the temperature of the mixture constant at 30° C. With each addition of dimethyl chlorosilane, the mixture became hazy but cleared in a short period of time. Once the addition of dimethyl chlorosilane was complete, the mixture was heated to 90° C. for 3 hours. The reaction was then washed with excess water several times to reduce the acidity of the mixture. The resulting mixture was dried over silica gel, filtered and vacuumed to remove solvent and traces of water at 65° C. overnight. A clear fluid was then obtained with a very strong Si—H band in infra red spectroscopy (IR) at 2130 cm$^{-1}$, which confirms the reaction. GPC analysis showed the molecular weight to be 1200 g/mol.
Step 2

40 g of Hydride terminated FMS-9922 was dissolved in 50 ml of reagent grade toluene and the temperature raised to around 90° C. To the reaction mixture 2 drops of hexachloroplatinic (IV) acid (0.01M $H_2PtCl_6$ from Sigma) solution in isopropanol (by Merck) was then added. After this catalyst solution had been added, the mixture was refluxed for 1 hour and the solvent distilled off in order to get the final product. The reaction was followed by H-NMR and gel permeation chromatography (GPC) confirmed the final molecular weight to be 2700 g/mol.

TABLE 1

Resulting polymer block ratios
Stoiciometric ratios for reaction product:

| | Polymer block | | |
|---|---|---|---|
| | PO<br>m | F—SiO<br>n | PO<br>p |
| Ratio | 11 | 9.7 | 11 |

Example 2

Synthesis of Aliphatic Linked Dimethylsiloxane Based Triblock Copolymer Pre-Soft-Segment To 130 ml of reagent grade toluene in a separable flask fitted with a mechanical stirrer, was added 64 g of allyl terminated poly(propylene glycol) (MW=700 g/mol, Jiangsu GPRO Co.) and both were mixed and heated to reflux. Then 40 g of hydride terminated poly(dimethyl siloxane) (Silmer H Di 10 by Siltech Corp.) was dissolved in 50 ml reagent grade toluene and the temperature raised to around 90° C. To this reaction mixture 2 drops of hexachloroplatinic(IV) acid (0.01M $H_2PtCl_6$ from Sigma) solution in isopropanol was added. After this catalyst solution was added, the mixture was refluxed for 1 hour and then the solvent was distilled off in

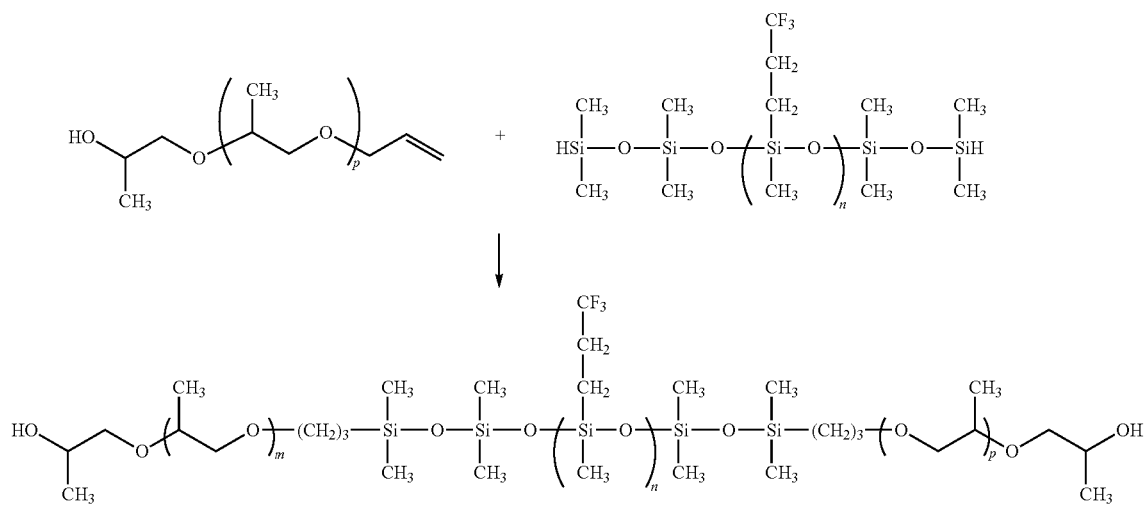

To 90 ml of reagent grade toluene in a 4 neck separable flask fitted with mechanical stirrer, 46.67 g of Allyl terminated poly(propylene glycol) (MW=700 g/mol, Jiangsu GPRO Group Co.) was added and then heated to reflux. Then order to get the final product. The reaction was followed with H-NMR and gel permeation chromatography (GPC) confirmed the final molecular weight of the product to be 2300 g/mol.

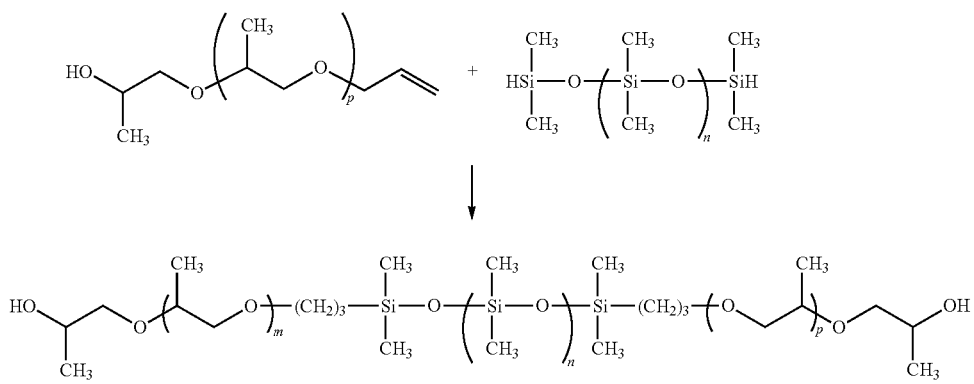

TABLE 2

Polymer block ratios
Stoiciometric ratios for reaction product:

| | Polymer block | | |
|---|---|---|---|
| | PO m | SiO n | PO p |
| Ratio | 11 | 11 | 11 |

Example 3

Synthesis of Aromatic Linked Siloxane Based Triblock Copolymer Pre-Soft-Segment

To a 100 ml separable flask fitted with a mechanical stirrer, 15 g of hydroxy terminated polydimethyl siloxane (DMS-S14 from Gelest Inc.) was added along with 5.36 g of di-chloro p-xylene (from Sigma) and 0.0089 g of Copper(II) acetylacetonate (Cu(Acac)$_2$ from Sigma). The reaction mixture was refluxed at 110° C. for 5 hrs. At this point, 19.77 g of hydroxy terminated poly(propylene glycol) (from Sigma) was added dropwise and the reaction mixture was then refluxed for another 15 hr. The progress of reaction was followed by $^1$H-NMR and the final molecular weight, determined by gel permeation chromatography (GPC), was 3000 g/mol.

H-NMR analysis: Solvent used for $^1$H-NMR analysis is CDCl$_3$.

Aromatic H=7.25-7.45 ppm, —CH$_2$=4.5-4.6 ppm, —CH$_3$ (of PPO)=1-1.4 ppm, —CH$_2$ (of PPO)=3.2-3.8 ppm, —OH (of PPO)=3.8-4 ppm, —CH$_3$(silanol)=0.5-0.8 ppm.

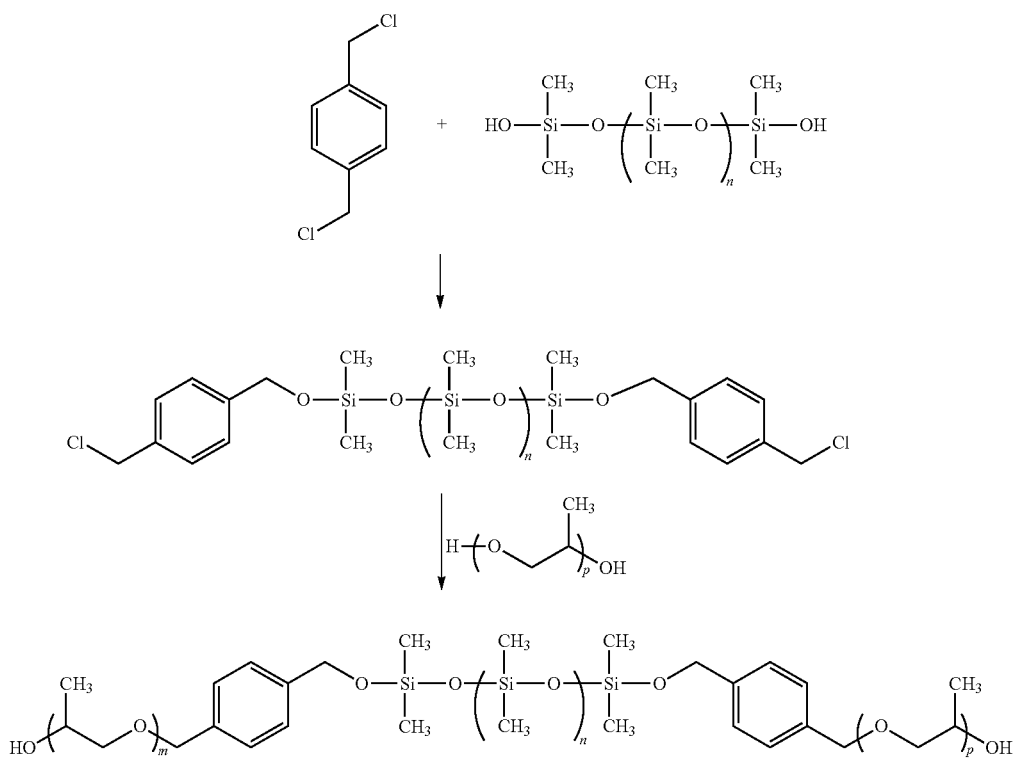

TABLE 3

Resulting polymer block ratios
Stoiciometric ratios for reaction product:

| | Polymer block | | |
|---|---|---|---|
| | PO m | SiO n | PO p |
| Ratio | 14 | 15.5 | 14 |

Example 4

Synthesis of Aromatic Linked Fluorosiloxane Based Triblock Copolymer Pre-Soft-Segment

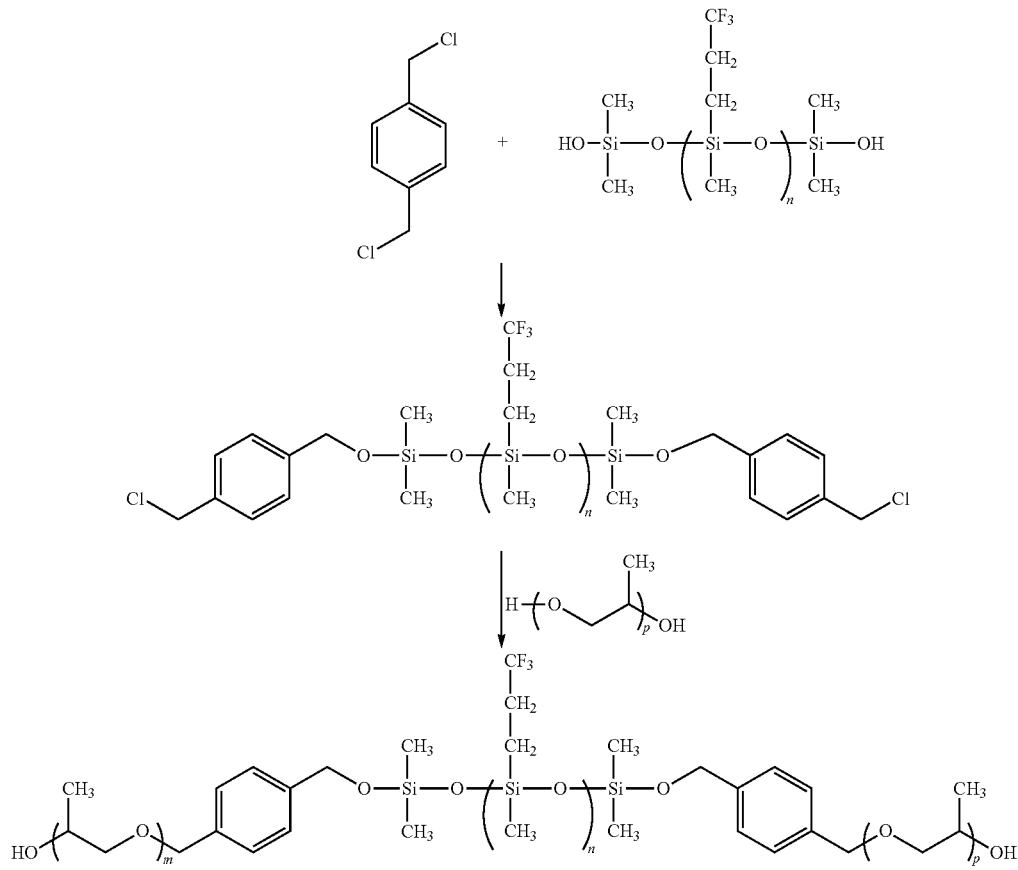

To a 100 ml separable flask fitted with a mechanical stirrer, 15 g of hydroxy terminated polytrifluoromethyl siloxane (FMS-9922, Gelest inc.) was added along with 5.9 g of dichloro p-xylene and 0.0098 g of copper(II) acetylacetonate (Cu(Acac)$_2$ from Sigma). The reaction mixture was refluxed at 110° C. for 5 hrs. At this point, 21.75 g of hydroxy terminated poly(propylene glycol) (from Sigma) was added dropwise to the reaction mixture. The reaction was refluxed for another 15 hr. The progress of reaction was followed by $^1$H-NMR analysis and the molecular weight, determined by gel permeation chromatography (GPC), was 3100 g/mol.

$^1$H-NMR analysis: Solvent used for H-NMR analysis is CDCl$_3$.

Aromatic $^1$H=7.25-7.45 ppm, —CH$_2$=4.5-4.6 ppm, —CH$_3$ (of PPO)=1-1.4 ppm, —CH$_2$ (of PPO)=3.2-3.8 ppm, —OH (of PPO)=3.8-4 ppm, —CH$_3$(silanol)=0.5-0.8 ppm.

TABLE 4

Polymer block ratios
Stoiciometric ratios for reaction product:

| | Polymer block | | |
|---|---|---|---|
| | PO m | FSiO n | PO p |
| Ratio | 14 | 9.2 | 14 |

Example 5

Preparation of Water Blown Foam

The pre-soft segments prepared can be described as having polymer block ratios which are numerically represented by the letters m, n and o for the constituents PO/SiO/PO respectively. The triblock copolymers prepared in Examples 1 and 2 with specific m, n, o ratios were formulated into polyurethane/urea foams as illustrated by Table 7.

The process for preparing the foam was a two-step procedure. The following describes the method of manufacture of the first product in Table 7. The same procedure was used to prepare other foams as described by Table 8.

Step 1) Firstly a mixture was made with 0.041 g of DABCO LV-33 (Airproducts), 0.120 g of bismuth neodecanoate (Bicat 8108M from Shepherd chemicals), 0.467 g of diethanol amine (DEOA, from Sigma), 7.917 g of synthesized block copolymer, 0.200 g water and 0.1 g of surfactant (Niax L-618 from Airproducts) in a plastic flat bottomed container. This is then thoroughly mixed manually for 30 sec until a homogenous mixture was obtained.

Step 2) To the above mixture, 15 g of a diisocyanate prepolymer (PPT 95A Airproducts) was added. This was then thoroughly mixed by a mechanical stirrer for about 5 seconds. The material was then molded and cured at 70° C. for 2.5 hours and post cured at 50° C. for another 3 hours.

TABLE 5

Formulation details for foam

| Formulation Identification | Polymer block (PO/SiO/PO) Ratio m:n:p | DABCO | BICAT | DEOA | H₂O |
|---|---|---|---|---|---|
| VF230209A | 11:11:11 | 0.0325 | 0.015 | 0.40 | 1.0 |
| VF090309B | 11:9:11 | 0.0325 | 0.015 | 0.40 | 1.0 |

Example 6

Comparative Example of Formulation of Water Blown Foam from Triblock Copolymer Pre-Soft Segment and Individual Homopolymers Polyurethane/urea polymer foams from Example 5 were compared to foams made from the stoiciometric equivalent homopolymer soft segments. The foams with homopolymer based soft segments (VF130309 and VF190309) shown in FIG. 100 were produced as follows (VF130309):

Step 1) Firstly a mixture was made with 0.041 g of DABCO LV-33 (Airproducts), 0.120 g of bismuth neodecanoate (Bicat 8108M from Shepherd chemicals), 0.467 g of diethanol amine (DEOA, from Sigma), 3.056 g of poly (dimethyl siloxane) diol (DMS-s14 Gelest Inc.), 1.633 g of polypropylene oxide (Mw=700 g/mol), 0.200 g water and 0.1 g of surfactant (Niax L-618 from Airproducts). These were added to a plastic flat bottomed container and were thoroughly mixed manually for 30 sec until a homogenous mixture was obtained.

Step 2) To the above mixture, 15 g of a diisocyanate prepolymer (PPT 95A Airproducts) was added. This was then thoroughly mixed by a mechanical stirrer for 5 seconds. The material was then molded and cured at 70° C. for 2.5 hours and post cured at 50° C. for another 3 hours.

Figure 100:
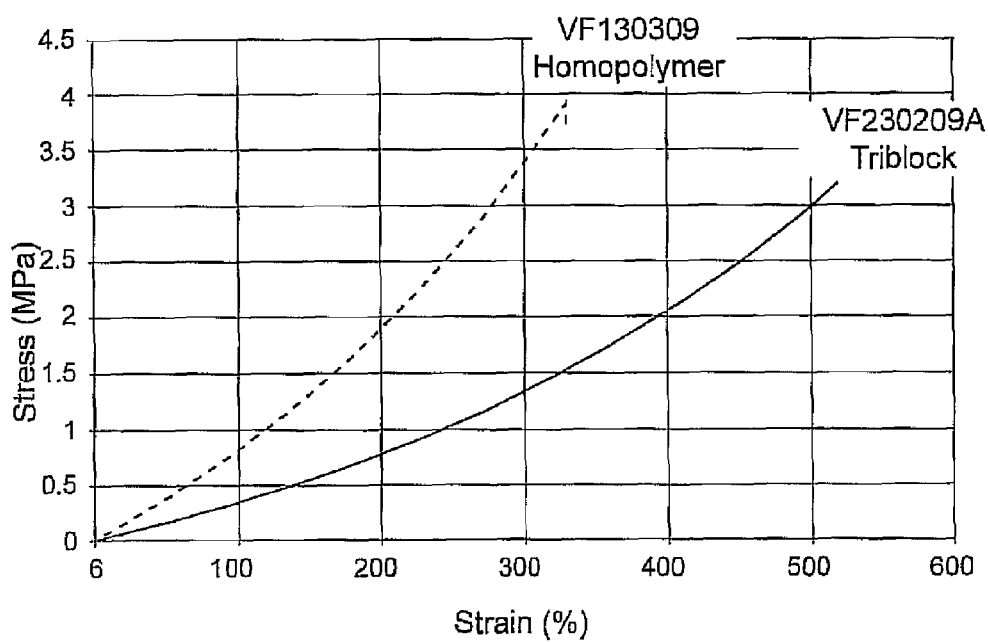
FIG. 100 is a graph of comparative mechanical properties of homo (VF130309) and triblock copolymer (VF230209A) soft segments.
Figure 101:
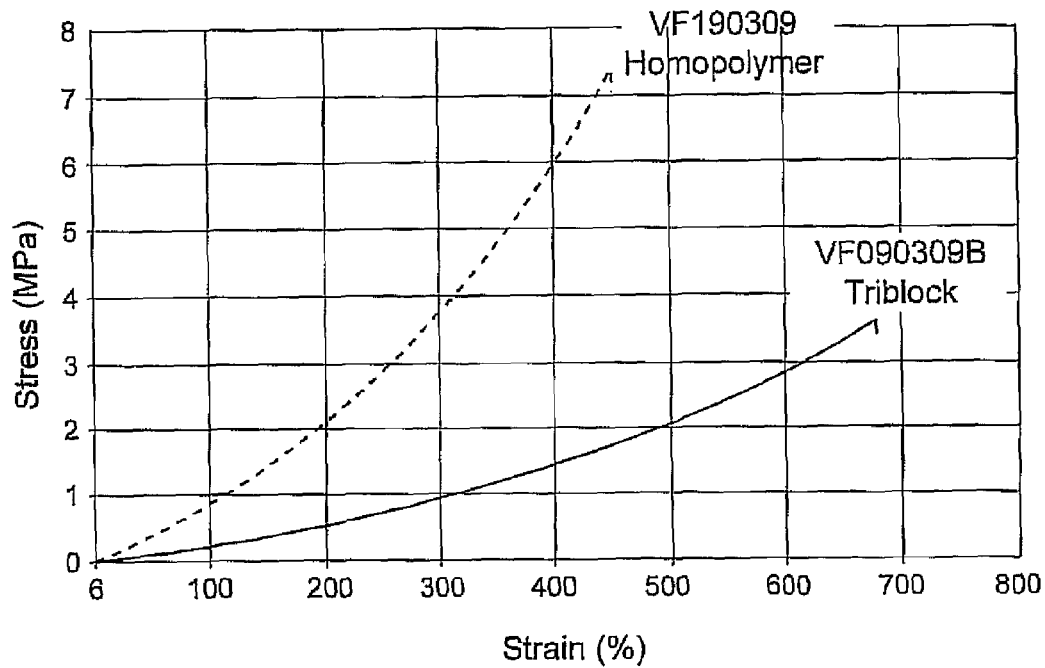
FIG. 101 is a graph of comparative mechanical properties of home (VF190309) and triblock copolymer (VF090309) soft segments.
Figure 102:
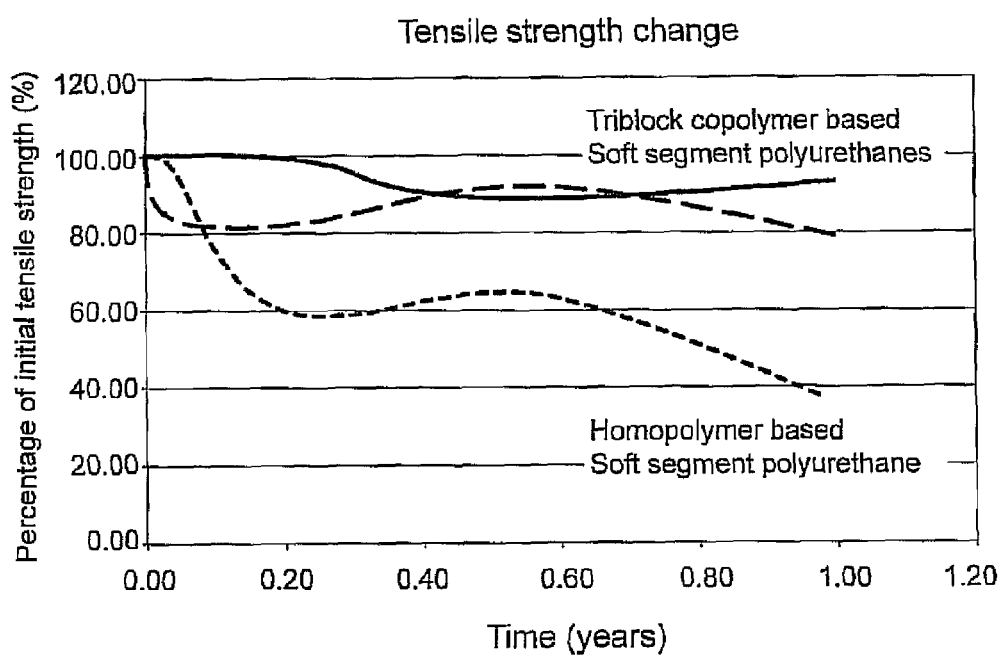
FIG. 102 is a graph illustrating the mechanical performance of triblock copolymer soft segments versus homopolymer soft segment during accelerated aging in simulated gastric fluid.

The foams in this example were made into dumbell shapes for tensile testing. FIGS. 100 and 101 illustrate the difference in mechanical behaviour between the comparative materials indicating a favourable lowering in modulus for the triblock copolymer pre-soft-segments.

Example 7

Comparative Stability of Triblock Copolymer Soft Segment Versus Homopolymer Soft Segment Tensile test specimens were prepared in the same manner to the materials used in Example 4 and were subjected to accelerated aging in simulated gastric fluid (as per United States Pharmacopeia, "USP"). The materials produced with the pre-synthesised triblock copolymer soft segments resulted in substantially improved mechanical stability in gastric fluid as compared to the urethane/urea linked homopolymer equivalent as illustrated in FIG. 90. This facilitates the use of such materials for prolonged periods in digestive and more specifically gastric environments.

Example 8

Preparation of Water Blown Foams

Several water blown polyurethane/urea foams were also produced with varying PO/EO/SiO polymer block ratios. The process for preparing the foam as described above was used.

TABLE 6

Water blown formulations incorporating siloxane containing copolymer pre-soft-segments.

| Polymer block ratio (PO/EO/SiO) m:n:p | DABCO | BICAT | DEOA | H₂O |
|---|---|---|---|---|
| 41.5:8.3:0.5 | 0.114 | 0.022 | 0.22 | 2.72 |
| 40.2:7.8:0.5 | 0.114 | 0.022 | 0.22 | 2.72 |
| 37.5:7:0.5 | 0.114 | 0.022 | 0.22 | 2.72 |
| 33.5:5.7:0.5 | 0.114 | 0.022 | 0.22 | 2.72 |
| 29.6:4.4:0.5 | 0.114 | 0.022 | 0.22 | 2.72 |
| 21.6:1.8:0.5 | 0.114 | 0.022 | 0.22 | 2.72 |
| 19:1:0.5 | 0.114 | 0.022 | 0.22 | 2.72 |
| 29.6:4.5:1.1 | 0.114 | 0.022 | 0.22 | 2.72 |

The results from the formulations described in Table 6 are shown in Table 7.

TABLE 7

Results from mechanical testing of foams from Table 5

| Polymer block ratio (PO/EO/SiO) m:n:p | % Elongation | Tensile Strength (N) |
|---|---|---|
| 41.5:8.3:0.5 | 233 | 0.46 |
| 40.2:7.8:0.5 | 243 | 0.31 |
| 37.5:7:0.5 | 237 | 0.3 |
| 33.5:5.7:0.5 | 260 | 0.23 |
| 29.6:4.4:0.5 | 320 | 0.23 |
| 21.6:1.8:0.5 | 497 | 0.23 |
| 19:1:0.5 | 462 | 0.22 |
| 29.6:4.5:1.1 | 437 | 0.29 |

Example 9

Use Example

Devices for use in the gastrointestinal system have historically not been made from specifically designed materials. Off the shelf materials used for application in the corrosive environment of the stomach have limited biostability and generally lose their functionality after a short time.

The foam of the invention can be used for production of a valve of the type described in our US2007-0198048A, the entire contents of which are incorporated herein by reference. The valve has an open position and a closed position. The valve will have a proximal end and a distal end. The valve material can open from the proximal direction when the action of swallowing (liquid or solid) stretches an orifice by between 100% and 3000% in circumference. The open orifice optionally closes non-elastically over a prolonged period of time, thus mimicking the body's natural response. The duration taken to close may be between 2 and 15 sec. The material can stretch to between 100%-300% from the distal direction when gas, liquid or solids exceeds a pre-determined force of between 25 cm H₂O and 60 cm H₂O. In some embodiments, the material absorbs less than 15% of its own mass of water at equilibrium. In some embodiments, the material loses (leaches) less than 3% of it's own mass at equilibrium in water or alcohol. In some embodiments, the material loses less than 10% of its tensile strength when immersed in a simulated gastric fluid at pH 1.2 for 30 days. In some embodiments, the valve material loses less than 25% of its % elongation when immersed in a simulated gastric fluid at pH 1.2 for 30 days.

Example 10

Valve Functional Testing

The healthy lower esophageal sphincter (LES) remains closed until an individual induces relaxation of the muscle by swallowing and thus allowing food to pass in the antegrade direction. Additionally when an individual belches or vomits they generate enough pressure in the stomach in the retrograde direction to overcome the valve. An anti-reflux valve must enable this functionality when placed in the body, thus a simple functional test is carried out to asses performance.

It has been reported that post fundoplication patients have yield pressures between 22-45 mmHg and that most of the patients with gastric yield pressure above 40 mmHg experienced problems belching. See *Yield pressure, anatomy of the cardia and gastro-oesophageal reflux*. Ismail, J. Bancewicz, J. Barow British Journal of Surgery. Vol: 82, 1995, pages: 943-947. Thus, in order to facilitate belching but prevent reflux, an absolute upper GYP value of 40 mmHg (550 mmH₂O) is reasonable. It was also reported that patients with visible esophagitis all have gastric yield pressure values under 15 mmHg, therefore, there is good reason to selectively target a minimum gastric yield pressure value that exceeds 15 mmHg See Id. An appropriate minimum gastric yield pressure value would be 15 mmHg+25% margin of error thus resulting in a minimum effective valve yield pressure value of 18.75 mmHg or 255 mmH₂O.

Figure 103:
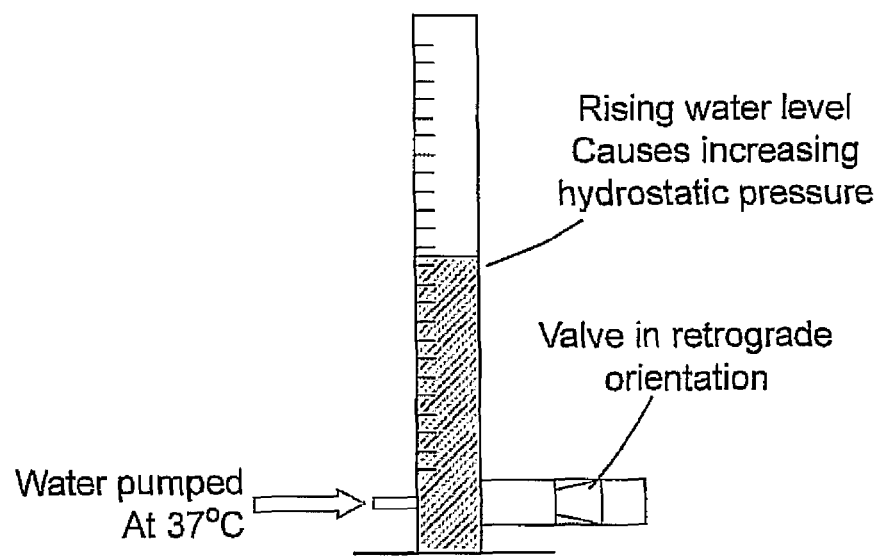
FIG. 103 depicts a gastric yield pressure test apparatus as utilized in Example 10.

The test apparatus consists of a 1 m high vertical tube as shown in FIG. 103, to which is connected a peristaltic pump and a fitting that is designed to house the valve to be tested.

The valve to be tested is placed in a water bath at 37° C. for 30 minutes to allow its temperature to equilibrate. Once the temperature of the valve has equilibrated it is then installed into the housing such that the distal closed end of the valve faces the inside of the test apparatus. The pump is then switched on at a rate of 800 ml/min to begin filling the vertical tube. The rising column of water exerts a pressure that forces the valve shut initially. As the pressure in the column rises the valve reaches a point where it everts and allows the water to flow through. This point, known as the yield pressure, is then recorded and the test repeated four times.

Example 11

Rationale for Accelerated Aging of Material

Clinical Condition being Simulated

The lower oesophagus of a normal patient can be exposed to the acidic contents of the stomach periodically without any adverse side effects. However, patients with gastro esophageal reflux disease experience damage to the mucosa of the lower oesophagus due to increased exposure to the gastric contents. Exposure of the lower oesophagus to acidic gastric contents is routinely measured in the clinic using dedicated pH measurement equipment. A typical procedure involves measuring pH over a 24-hour period. The levels of acid exposure in pathological reflux disease patients is summarised in Table 8 from six clinical references. See DeMeester T R, Johnson L F, Joseph G J, et al. *Patterns of Gastroesophageal Reflux in Health and Disease Ann. Surg.* October 1976 459-469; Pandolfino J E, Richter J E, Ours T, et al. *Ambulatory Esophageal pH Monitoring Using a Wireless System Am. J. Gastro* 2003; 98:4; Mahmood Z, McMahon B P, Arfin Q, et al. *Results of endoscopic gastroplasty for gastroesophageal reflux disease: a one year prospective follow-up Gut* 2003; 52:34-9; Park P O, Kjellin T, Appeyard M N, et al. *Results of endoscopic gastroplasty suturing for treatment of GERD: a multicentre trial Gastrointest endosc* 2001; 53:AB 115; Filipi C J, Lehman G A, Rothstein R I, et al. *Transoral flexible endoscopic suturing for treatment of GERD: a multicenter trial Gastrointest endosc* 2001; 53 416-22; and Arts J, Slootmaekers S Sifrim D, et al. *Endoluminal gastroplication (Endocinch) in GERD patient's refractory to PPI therapy Gastroenterology* 2002; 122:A47.

TABLE 8

Summary of acid exposure in patients with reflux disease

| Investigator | Number of patients | Details | % 24 h <pH 4 |
|---|---|---|---|
| DeMeester | 54 | Combined refluxers | 13.5 |
| Pandolfino | 41 | Gerd | 6.5 |
| Mahmood | 21 | Gerd | 11.11 |
| Park | 142 | Gerd | 8.5 |
| Filipi | 64 | Gerd | 9.6 |
| Arts | 20 | Gerd | 17 |
| Average | | | 11.035 |

Key Clinical Parameters

Considering that the lower oesophagus is exposed to the acidic pH exposure time for an average of 11% of the measurement period, an accelerated aging methodology can easily be conceived. Constant exposure of a test material to the gastric contents (or USP Simulated Gastric Fluid—Reference USP Pharmacopeia) would represent an almost 10-fold increase in the rate of aging. Thus the time required to simulate one year of exposure of the lower oesophagus to the gastric contents is described by equation 1.

$$\left(\frac{11.035}{100}\right) \times 365 \text{ days} = 40.28 \text{ days} \qquad \text{Equation 1}$$

Clinical Rationale

Immersion of test specimens in USP Simulated gastric fluid for 40.27 days at 37° C. will approximate one year's exposure of the lower oesophagus to acidic gastric contents in a GERD patient's scenario.

| Simulated Exposure | Real Time |
|---|---|
| 1 year | 40.28 days |
| 2 years | 80.56 days |
| 3 years | 120.84 days |

Figure 104:
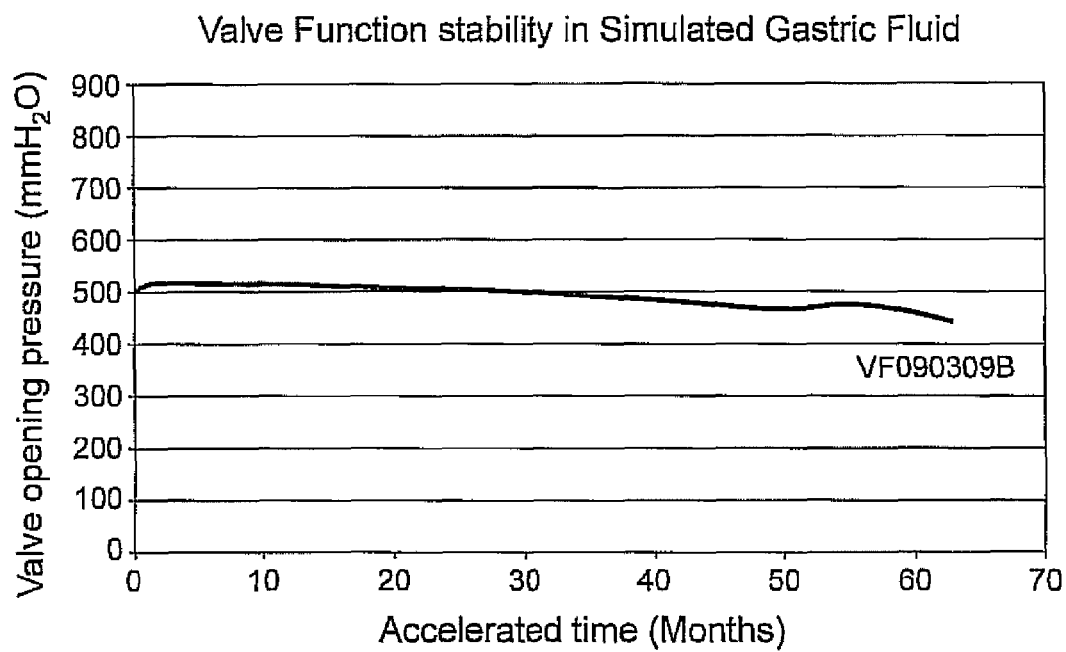
FIG. 104 and FIG. 105 depict results of accelerated stability of a valve prepared from a viscoelastic foam of the present invention.
Figure 105:
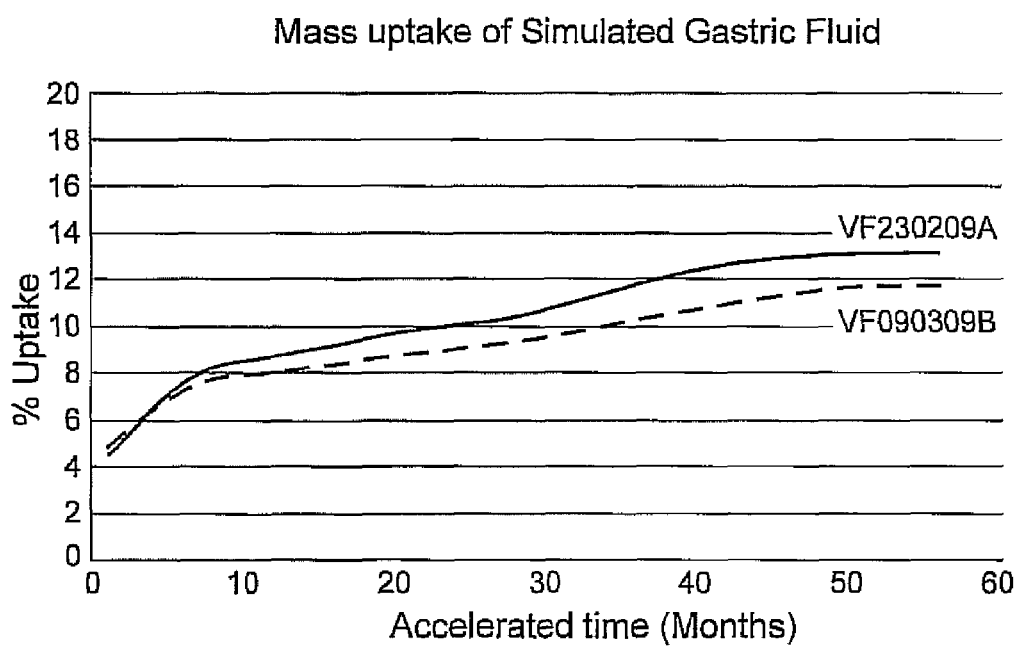

Results of accelerated stability of a valve prepared from a viscoelastic foam of the present invention are depicted in FIGS. 104 and 105.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

Various features of the invention are described in detail and illustrated herein. Appropriate features described with reference to one embodiment may be utilised in addition to and/or as a substitute for features described in other embodiments.

The invention is not limited to the embodiments hereinbefore described which may be varied in detail.

The invention claimed is:

1. A urological device comprising
a urological valve,
a support for the valve, the support being generally tubular and adapted for mounting in a urinary tract,
a bladder retainer for locating the device in a bladder and a urethral retainer to prevent migration of the device,
the valve including a plurality of valve leaflets,
the valve having internally located, stiffening reinforcement members the stiffening reinforcement members defining a fulcrum or hinge region about which the valve leaflets are movable from a normally closed configuration to an open configuration, the stiffening reinforcement members extending vertically,
the valve having a region of co-aption between the valve leaflets, the valve having the normally closed configuration in which the valve leaflets are engaged at the region of co-aption and the open configuration in which the leaflets are separated at the co-aption region for fluid flow through the valve, the valve leaflets being configured to evert automatically on movement between the closed configuration and the open configuration in response to applied urological pressure.

2. The urological device as claimed in claim 1, wherein the valve is of a viscoelastic polymeric foam material.

3. The urological device as claimed in claim 1, wherein the valve is adapted to open in response to a preset pressure applied over a preset time.

4. The urological device as claimed in claim 3, wherein the valve is adapted to open in response to a pressure of at least 750 mm H2O applied for at least 5 seconds.

5. The urological device as claimed in claim 1, wherein the valve is adapted to remain closed in response to a spike pressure applied for a short time as would be generated by a user coughing.

6. The urological device as claimed in claim 5, wherein the spike pressure is 900 mm H2O applied for a period of less than 0.5 seconds.

7. The urological device as claimed in claim 1, wherein the valve remains open as fluid flows therethrough without a requirement for a user to apply urological pressure.

8. The urological device as claimed in claim 7, wherein the valve returns to the closed configuration when flow through the valve has substantially stopped.

9. The urological device as claimed in claim 1, wherein the valve reverts on return from the open to the dosed configuration.

10. The urological device as claimed in claim 1, wherein the valve includes at least three valve leaflets.

11. The urological device as claimed in claim 1, wherein the valve includes a main body having a region which defines a hinge about which a portion of the valve main body is movable between the closed and open configurations.

12. The urological device as claimed in claim 1, wherein the stiffening reinforcement members are of the same material as that of the valve.

13. The urological device as claimed in claim 12, wherein the valve and the stiffening reinforcement members are integrally moulded.

14. The urological device as claimed in claim 1, wherein the support is of the same material as that of the valve.

15. The urological device as claimed in claim 14, wherein the valve and support are integrally moulded.

16. The urological device as claimed in claim 1, wherein the bladder retainer includes a flare extending radially outwardly of the support.

17. The urological device as claimed in claim 1, wherein the bladder retainer is of the same material as that of the support.

18. The urological device as claimed in claim 1, wherein the bladder retainer, the support and the valve are integrally moulded.

19. The urological device as claimed in claim 1, further comprising a stiffener for the bladder retainer.

20. The urological device as claimed in claim 19, wherein the stiffener is made of Nitinol shape memory material.

21. The urological device as claimed in claim 1, wherein the urethral retainer includes a meatal tab.

22. The urological device as claimed in claim 1, wherein the urethral retainer includes a bulbous region of compressive material.

23. The urological device as claimed in claim 1, wherein the device includes an antimicrobial coating.

24. A urological device comprising
a urological valve,
a support for the valve, the support being generally tubular and adapted for mounting in a urinary tract,
a bladder retainer for locating the device in a bladder and a urethral retainer to prevent migration of the device,
the valve including a plurality of valve leaflets,
the valve having internally located, stiffening reinforcement members, the stiffening reinforcement members defining a fulcrum or hinge region about which the valve leaflets are movable from a normally closed configuration to an open configuration, the stiffening reinforcement members being spaced about an internal circumference of the valve,
the valve having a region of co-aption between the valve leaflets, the valve having the normally closed configuration in which the valve leaflets are engaged at the region of co-aption and the open configuration in which the leaflets are separated at the co-aption region for fluid flow through the valve, the valve leaflets being configured to evert automatically on movement between the closed configuration and the open configuration in response to applied urological pressure.

25. The urological device as claimed in claim 24, wherein the valve is of a viscoelastic polymeric foam material.

26. The urological device as claimed in claim 24, wherein the valve is adapted to open in response to a preset pressure applied over a preset time.

27. The urological device as claimed in claim 26, wherein the valve is adapted to open in response a pressure of at least 750 mm H2O applied for at least 5 seconds.

28. The urological device as claimed in claim 24, wherein the valve is adapted to remain closed in response to a spike pressure applied for a short time as would be generated by a user coughing.

29. The urological device as claimed in claim 28, wherein the spike pressure is 900 mm H2O applied for a period of less than 0.5 seconds.

30. The urological device as claimed in claim 24, wherein the valve remains open as fluid flows therethrough without a requirement for a user to apply urological pressure.

31. The urological device as claimed in claim 30, wherein the valve returns to the closed configuration when flow through the valve has substantially stopped.

32. The urological device as claimed in claim 24, wherein the valve reverts on return from the open to the closed configuration.

33. The urological device as claimed in claim 24, wherein the valve includes at least three valve leaflets.

34. The urological device as claimed in claim 24, wherein the valve includes a main body having a region which defines a hinge about which a portion of the valve main body is movable between the closed and open configurations.

35. The urological device as claimed in claim 24, wherein the stiffening reinforcement members are of the same material as that of the valve.

36. The urological device as claimed in claim 35, wherein the valve and the stiffening reinforcement members are integrally moulded.

37. The urological device as claimed in claim 24, wherein the support is of the same material as that of the valve.

38. The urological device as claimed in claim 37, wherein the valve and support are integrally moulded.

39. The urological device as claimed in claim 24, wherein the bladder retainer includes a flare extending radially outwardly of the support.

40. The urological device as claimed in claim 24, wherein the bladder retainer is of the same material as that of the support.

41. The urological device as claimed in claim 24, wherein the bladder retainer, the support and the valve are integrally moulded.

42. The urological device as claimed in claim 24, further comprising a stiffener for the bladder retainer.

43. The urological device as claimed in claim 42, wherein the stiffener is made of Nitinol shape memory material.

44. The urological device as claimed in claim 24, wherein the urethral retainer includes a meatal tab.

45. The urological device as claimed in claim 24, wherein the urethral retainer includes a bulbous region of compressive material.

46. The urological device as claimed in claim 24, wherein the device includes an antimicrobial coating.

* * * * *